United States Patent
Park

(10) Patent No.: US 11,937,501 B2
(45) Date of Patent: Mar. 19, 2024

(54) HETEROCYCLIC COMPOUND AND ORGANIC LIGHT- EMITTING DEVICE INCLUDING HETEROCYCLIC COMPOUND

(71) Applicant: Samsung Display Co., Ltd., Yongin-si (KR)

(72) Inventor: Hyejeong Park, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 290 days.

(21) Appl. No.: 17/121,521

(22) Filed: Dec. 14, 2020

(65) Prior Publication Data

US 2021/0320259 A1     Oct. 14, 2021

(30) Foreign Application Priority Data

Apr. 13, 2020    (KR) .................. 10-2020-0044778

(51) Int. Cl.
*H01L 51/50*       (2006.01)
*C07D 471/04*     (2006.01)
*H10K 85/60*      (2023.01)
*H10K 50/16*      (2023.01)

(52) U.S. Cl.
CPC ......... *H10K 85/654* (2023.02); *C07D 471/04* (2013.01); *H10K 85/6572* (2023.02); *H10K 50/16* (2023.02)

(58) Field of Classification Search
CPC ........ H10K 50/10; H10K 50/15; H10K 50/30; H10K 50/113; H10K 50/622; H10K 50/631
See application file for complete search history.

(56) References Cited

U.S. PATENT DOCUMENTS

| | | | |
|---|---|---|---|
| 9,093,650 B2 | 7/2015 | Kim et al. | |
| 9,624,193 B2 | 4/2017 | Aihara et al. | |
| 10,326,111 B2 | 6/2019 | Yoo et al. | |
| 2009/0096357 A1* | 4/2009 | Lee | H01L 51/5092 313/504 |
| 2014/0330013 A1* | 11/2014 | Aihara | C07D 251/24 544/180 |
| 2017/0018600 A1 | 1/2017 | Ito et al. | |
| 2017/0186964 A1 | 6/2017 | Cho et al. | |
| 2017/0200899 A1 | 7/2017 | Kim et al. | |
| 2018/0114940 A1 | 4/2018 | Pavicic et al. | |
| 2019/0088896 A1* | 3/2019 | Kim | H01L 51/506 |
| 2020/0095226 A1* | 3/2020 | Pan | H10K 85/654 |
| 2020/0203650 A1 | 6/2020 | Kim et al. | |

FOREIGN PATENT DOCUMENTS

| | | | |
|---|---|---|---|
| CN | 108409730 | 8/2018 | |
| CN | 109705148 | * 5/2019 | ............ H01L 51/50 |
| JP | 5812583 | 11/2015 | |
| KR | 10-2017-0116500 | 10/2017 | |

(Continued)

*Primary Examiner* — Gregory D Clark
(74) *Attorney, Agent, or Firm* — H.C. Park & Associates, PLC

(57) ABSTRACT

An organic light-emitting device includes: a first electrode; a second electrode facing the first electrode; an organic layer disposed between the first electrode and the second electrode and including an emission layer; and at least one of heterocyclic compounds represented by Formulae 1-1 to 1-3, as defined herein.

17 Claims, 6 Drawing Sheets

(56) References Cited

FOREIGN PATENT DOCUMENTS

| KR | 10-2018-0044823 | 5/2018 | | |
|----|----|----|----|----|
| KR | 10-1926769 | 12/2018 | | |
| KR | 10-2019-0053562 | 5/2019 | | |
| KR | 2017149589 B1 * | 5/2019 | ............ | H01L 51/50 |
| KR | 10-2019-0076487 | 7/2019 | | |

* cited by examiner

| 190 |
|---|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

| 190 |
|---|
| 150-2 |
| 155-1 |
| 150-1 |
| 110 |

| 190 |
| 150-3 |
| 155-2 |
| 150-2 |
| 155-1 |
| 150-1 |
| 110 |

HETEROCYCLIC COMPOUND AND ORGANIC LIGHT-EMITTING DEVICE INCLUDING HETEROCYCLIC COMPOUND

CROSS-REFERENCE TO RELATED APPLICATION

This application claims priority from and the benefit of Korean Patent Application No. 10-2020-0044778, filed on Apr. 13, 2020, which is hereby incorporated by reference for all purposes as if fully set forth herein.

BACKGROUND

Field

Exemplary embodiments of the invention relate generally to a heterocyclic compound, and more particularly, an organic light-emitting device including the heterocyclic compound.

Discussion of the Background

Organic light-emitting devices (OLEDs) are self-emission devices that, as compared with related devices, have wide viewing angles, high contrast ratios, short response times, and excellent characteristics in terms of brightness, driving voltage, and/or response speed, and can produce full-color images.

OLEDs may include a first electrode on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

The above information disclosed in this Background section is only for understanding of the background of the inventive concepts, and, therefore, it may contain information that does not constitute prior art.

SUMMARY

One or more exemplary embodiments include at least one of a heterocyclic compound and an organic light emitting device including the same. As an example, organic light-emitting devices including heterocyclic compounds constructed according to the principles and exemplary implementations of the invention have excellent driving voltage, external quantum efficiency, and long lifespan.

Additional features of the inventive concepts will be set forth in the description which follows, and in part will be apparent from the description, or may be learned by practice of the inventive concepts.

According to one aspect of the invention, an organic light-emitting device includes: a first electrode; a second electrode facing the first electrode; an organic layer disposed between the first electrode and the second electrode and including an emission layer; and at least one of heterocyclic compounds is represented by Formulae 1-1 to 1-3:

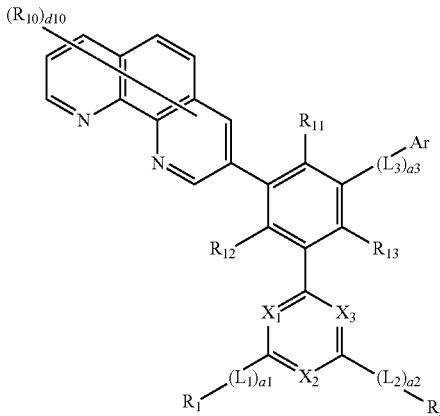

Formula 1-1

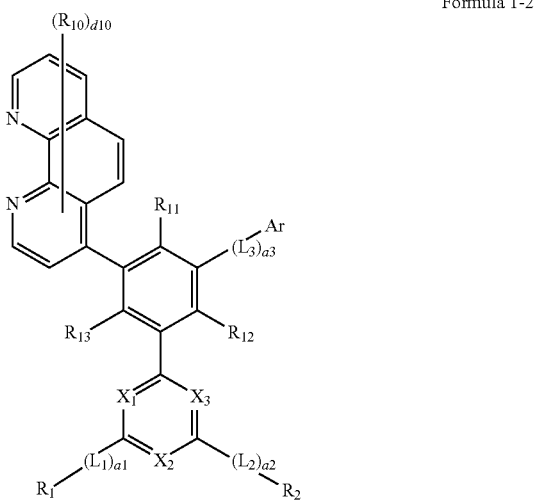

Formula 1-2

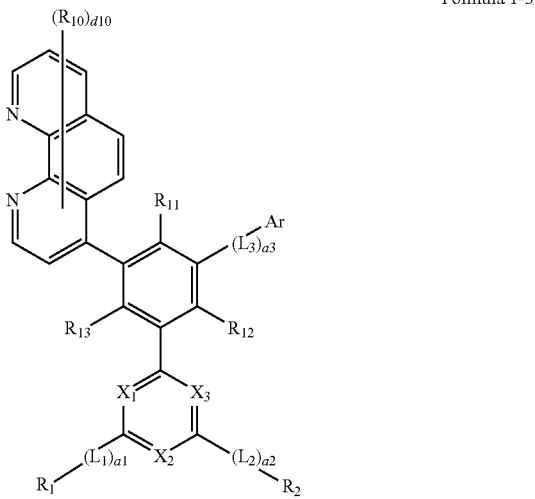

Formula 1-3 wherein, in Formulae 1-1 to 1-3, ring Ar is a π electron-depleted nitrogen-containing $C_1$-$C_{60}$ cyclic group unsubstituted or substituted with at least one $R_{10a}$;

$X_1$ is $C(R_{21})$ or N;

$X_2$ is $C(R_{22})$ or N;

$X_3$ is $C(R_{23})$ or N;

$L_1$ to $L_3$ are each, independently from one another, a single bond, a $C_5$-$C_{30}$ carbocyclic group unsubstituted or substituted with at least one $R_{20a}$, or a $C_2$-$C_{30}$ heterocyclic group unsubstituted or substituted with at least one $R_{20a}$;

a1 to a3 are each, independently from one another, an integer from 1 to 5;

$R_1$ and $R_2$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, a π electron-rich $C_3$-$C_{60}$ cyclic group unsubstituted or substituted with at least one $R_{30a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);

$R_{10}$ to $R_{13}$, $R_{10a}$, $R_{20a}$, $R_{30a}$, and $R_{21}$ to $R_{23}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);

d10 is an integer from 0 to 7; and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group is:

deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, a hydroxyl group, a cyano group, a nitro group, an amidino group, a hydrazine group, a hydrazone group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic fused polycyclic group; a monovalent non-aromatic fused heteropolycyclic group; a $C_1$-$C_{60}$ alkyl group substituted with at least one of deuterium, —F, and a cyano group; a $C_6$-$C_{60}$ aryl group substituted with at least one of deuterium, —F, and a cyano group; a biphenyl group; or a terphenyl group.

The first electrode may be an anode, the second electrode may be a cathode, and the organic layer may include the at least one of the heterocyclic compounds represented by Formulae 1-1 to 1-3, and the organic layer may further include a hole transport region disposed between the first electrode and the emission layer and an electron transport region disposed between the emission layer and the second electrode.

The hole transport region may include a hole injection layer, a hole transport layer, an emission auxiliary layer, an electron blocking layer, or any combination thereof, the electron transport region may include a hole blocking layer, an electron transport layer, an electron injection layer, or any combination thereof, and the electron transport region may include the at least one of the heterocyclic compounds.

The hole transport region may include a compound represented by Formula 201 or Formula 202:

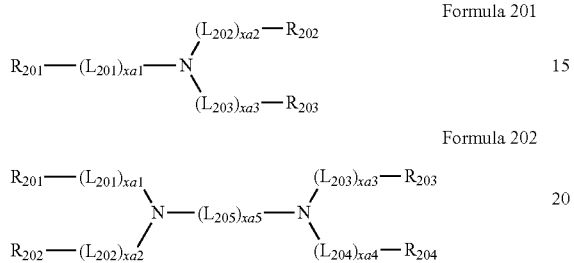

Formula 201

Formula 202 wherein, in Formulae 201 and 202, the variables are defined herein.

The electron transport region may include the electron injection layer; and the electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The emission layer may include an anthracene-based compound.

According to another aspect of the invention, an organic light-emitting device includes: a first electrode; a second electrode facing the first electrode; m emission units disposed between the first electrode and the second electrode, each including at least one emission layer; and m−1 charge generating layers, each between two adjacent emission units from among the m emission units, wherein m is an integer of 2 or greater, and at least one of the m−1 charge generating layers includes at least one of the heterocyclic compounds represented by Formulae 1-1 to 1-3:

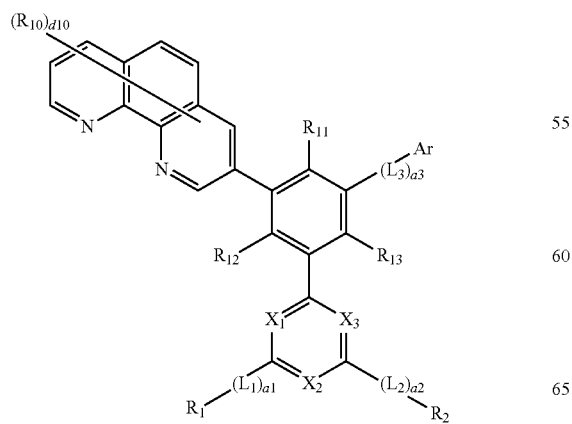

Formula 1-1

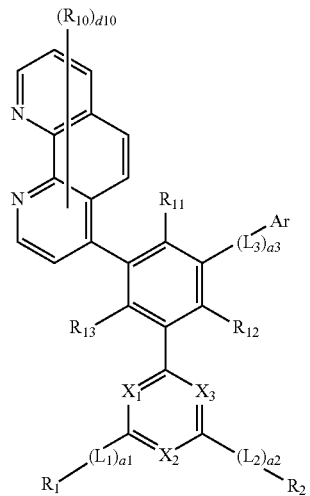

Formula 1-2

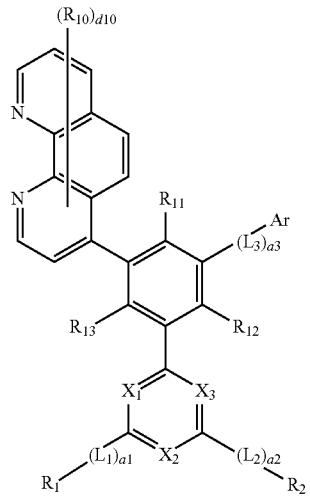

Formula 1-3 wherein, in Formulae 1-1 to 1-3,
ring Ar is a π electron-depleted nitrogen-including $C_1$-$C_{60}$ cyclic group unsubstituted or substituted with at least one $R_{10a}$;
$X_1$ is $C(R_{21})$ or N;
$X_2$ is $C(R_{22})$ or N;
$X_3$ is $C(R_{23})$ or N;
$L_1$ to $L_3$ are each, independently from one another, a single bond, a $C_5$-$C_{30}$ carbocyclic group unsubstituted or substituted with at least one $R_{20a}$, or a $C_2$-$C_{30}$ heterocyclic group unsubstituted or substituted with at least one $R_{20a}$;
a1 to a3 are each, independently from one another, an integer from 1 to 5;
$R_1$ and $R_2$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, a π electron-rich $C_3$-$C_{60}$ cyclic group unsubstituted or substituted with at least one $R_{30a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);

$R_{10}$ to $R_{13}$, $R_{10a}$, $R_{20a}$, $R_{30a}$, and $R_{21}$ to $R_{23}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);

d10 is an integer from 0 to 7; and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group is:

deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, a hydroxyl group, a cyano group, a nitro group, an amidino group, a hydrazine group, a hydrazone group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic fused polycyclic group; a monovalent non-aromatic fused heteropolycyclic group; a $C_1$-$C_{60}$ alkyl group substituted with at least one of deuterium, —F, and a cyano group; a $C_6$-$C_{60}$ aryl group substituted with at least one of deuterium, —F, and a cyano group; a biphenyl group; or a terphenyl group.

According to a further aspect of the invention, a heterocyclic compound represented by one of Formulae 1-1 to 1-3:

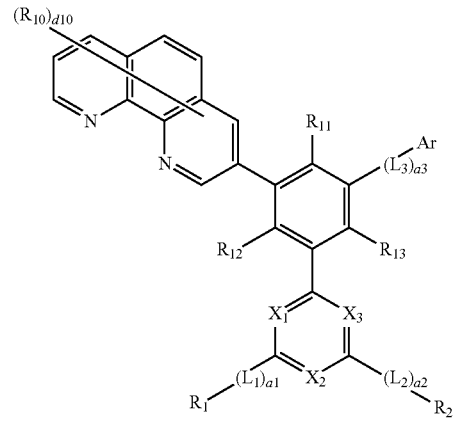

Formula 1-1

-continued

Formula 1-2

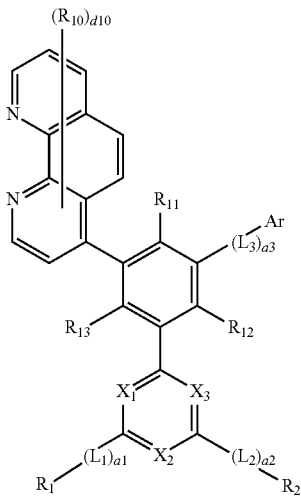

Formula 1-3

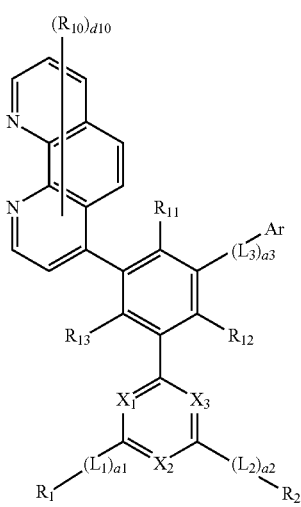

wherein, in Formulae 1-1 to 1-3,
ring Ar is a π electron-depleted nitrogen-containing $C_1$-$C_{60}$ cyclic group unsubstituted or substituted with at least one $R_{10a}$;
$X_1$ is $C(R_{21})$ or N;
$X_2$ is $C(R_{22})$ or N;
$X_3$ is $C(R_{23})$ or N;
$L_1$ to $L_3$ are each, independently from one another, a single bond, a $C_5$-$C_{30}$ carbocyclic group unsubstituted or substituted with at least one $R_{20a}$, or a $C_2$-$C_{30}$ heterocyclic group unsubstituted or substituted with at least one $R_{20a}$;
a1 to a3 are each, independently from one another, an integer from 1 to 5;
$R_1$ and $R_2$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, a π electron-rich $C_3$-$C_{60}$ cyclic group unsubstituted or substituted with at least one $R_{30a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);
$R_{10}$ to $R_{13}$, $R_{10a}$, $R_{20a}$, $R_{30a}$, and $R_{21}$ to $R_{23}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);
d10 is an integer from 0 to 7; and
a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group is:
deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, a hydroxyl group, a cyano group, a nitro group, an amidino group, a hydrazine group, a hydrazone group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic fused polycyclic group; a monovalent non-aromatic fused heteropolycyclic group; a $C_1$-$C_{60}$ alkyl group substituted with at least one of deuterium, —F, and a cyano group; a $C_6$-$C_{60}$ aryl group substituted with at least one of deuterium, —F, and a cyano group; a biphenyl group; or a terphenyl group.

The π electron-depleted nitrogen-containing $C_1$-$C_{60}$ cyclic group may be a) a first ring, b) a fused ring in which at least two first rings may be fused, or c) a fused ring in which at least one first ring and at least one second ring may be fused; the π electron-rich $C_3$-$C_{60}$ cyclic group may be a) a second ring or b) a fused ring in which at least two second rings may be fused; the first ring may be an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, a tetrazine group, a pentazine group, a hexazine group, or a thiadiazole group, and the second ring may be a benzene group, a cyclopentadiene group, a pyrrole group, a furan group, a thiophene group, or a silole group.

The π electron-depleted nitrogen-containing $C_1$-$C_{60}$ cyclic group may be a group as defined herein.

The π electron-depleted nitrogen-containing $C_1$-$C_{60}$ cyclic group may be a group as further defined herein.

The variables defined for the heterocyclic compound, may be as follows:

$X_1$ may be C($R_{21}$), $X_2$ may be C($R_{22}$), and $X_3$ may be N;
$X_1$ may be C($R_{21}$), $X_3$ may be C($R_{23}$), and $X_2$ may be N;
$X_2$ may be C($R_{22}$), $X_3$ may be C($R_{23}$), and $X_1$ may be N;
$X_1$ and $X_2$ may be each N, and $X_3$ may be C($R_{23}$);
$X_1$ and $X_3$ may be each N, and $X_2$ may be C($R_{22}$);
$X_2$ and $X_3$ may be each N, and $X_1$ may be C($R_{21}$); or
$X_1$, $X_2$, and $X_3$ may be each N;
wherein $R_{21}$ to $R_{23}$ are each, independently from one another, have the same meaning as defined above.

The variables $L_1$ to $L_3$ may be defined herein.
The variables $L_1$ to $L_3$ may be further defined herein.
The variables $R_{10}$ to $R_{13}$, $R_{10a}$, $R_{20a}$, $R_{30a}$, and $R_{21}$ to $R_{23}$ may each, independently from one another, be defined herein.
The variables $R_{10}$ to $R_{13}$ may each, independently from one another, be defined herein.
The variables $R_1$ and $R_2$ may each, independently from one another, be defined herein.
The Formulae 1-1 to 1-3 may each satisfy at least one of Conditions 1 to 3 as defined herein.
In Formulae 1-1 to 1-3, a group represented by *-($L_1$)$_{a1}$-$R_1$ and a group represented by *-($L_2$)$_{a2}$-$R_2$ satisfy at least one of Conditions 1a to 3a, as defined herein.
The π electron-rich $C_3$-$C_{60}$ cyclic group may be a group as defined herein.
The heterocyclic compound may be one of Compounds 1 to 32, as defined herein.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIG. 1 is a schematic cross-sectional diagram of an exemplary embodiment of an organic light-emitting device constructed according to principles of the invention.

FIG. 2 is a schematic cross-sectional diagram of another exemplary embodiment of an organic light-emitting device constructed according to principles of the invention.

FIG. 3 is a schematic cross-sectional diagram of a further exemplary embodiment of an organic light-emitting device constructed according to principles of the invention.

FIG. 4 is a schematic cross-sectional diagram of yet another exemplary embodiment of an organic light-emitting device constructed according to principles of the invention.

FIG. 5 is a schematic cross-sectional diagram of still another exemplary embodiment of an organic light-emitting device constructed according to principles of the invention.

FIG. 6 is a schematic cross-sectional diagram of a still further exemplary embodiment of an organic light-emitting device constructed according to principles of the invention.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

A heterocyclic compound may be represented by one of Formulae 1-1 to 1-3:

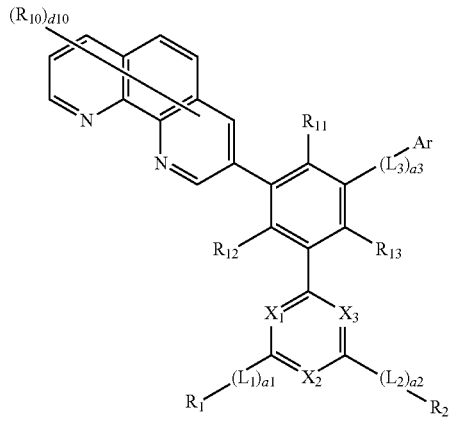

Formula 1-1

-continued

Formula 1-2

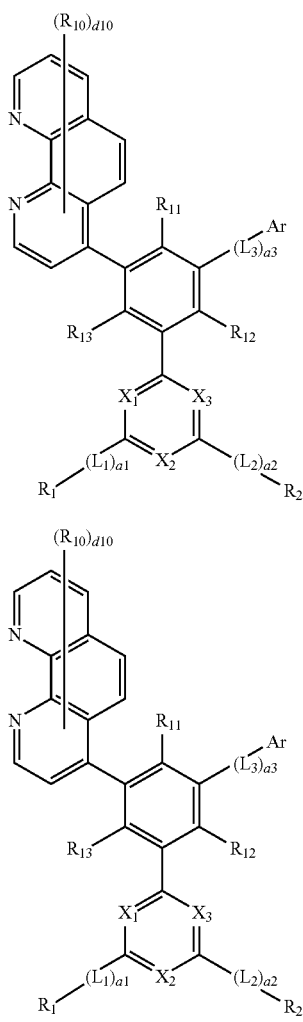

Formula 1-3 wherein, in Formulae 1-1 to 1-3,
ring Ar may be a π electron-depleted nitrogen-containing $C_1$-$C_{60}$ cyclic group unsubstituted or substituted with at least one $R_{10a}$, In some exemplary embodiments, the π electron-depleted nitrogen-containing $C_1$-$C_{60}$ cyclic group may be a) a first ring, b) a condensed ring in which at least two first rings are condensed, or c) a condensed ring in which at least one first ring and at least one second ring are condensed, the first ring may be an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, a tetrazine group, a pentazine group, a hexazine group, or a thiadiazole group, and the second ring may be a benzene group, a cyclopentadiene group, a pyrrole group, a furan group, a thiophene group, or a silole group.

In some exemplary embodiments, the π electron-depleted nitrogen-containing $C_1$-$C_{60}$ cyclic group may be one of an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, an acridine group, a pyridopyrazine group, and groups represented by Formulae 2-1 to 2-17:

2-1
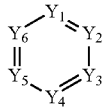

2-2
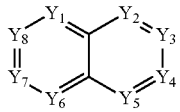

2-3
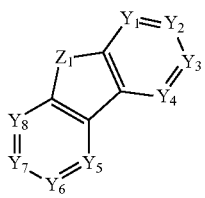

2-4
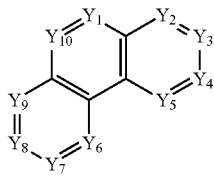

2-5
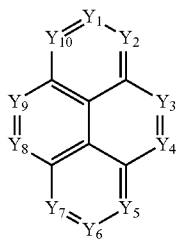

2-6
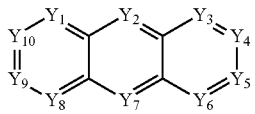

2-7
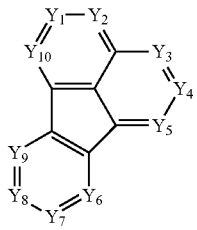

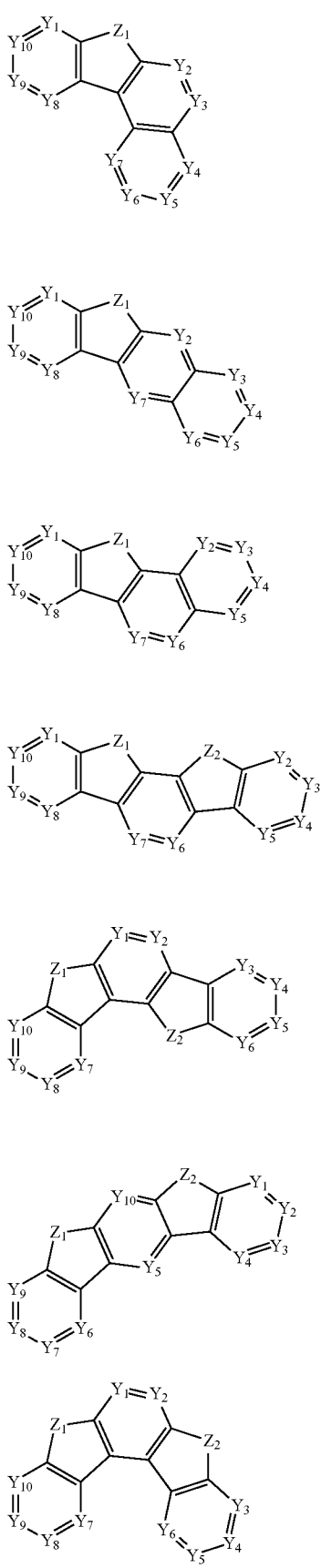

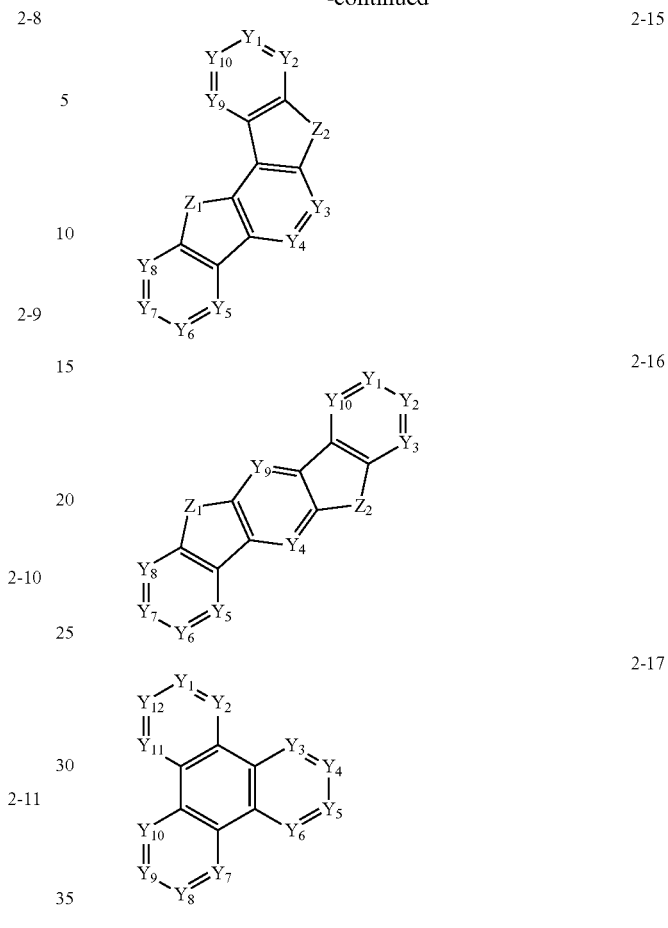

wherein, in Formulae 2-1 to 2-17,
$Z_1$ may be O, S, $N(R_{1a})$, $C(R_{1a})(R_{1b})$, or $Si(R_{1a})(R_{1b})$,
$Z_2$ may be O, S, $N(R_{2a})$, $C(R_{2a})(R_{2b})$, or $Si(R_{2a})(R_{2b})$,
$Y_1$ may be $C(R_{31})$ or N,
$Y_2$ may be $C(R_{32})$ or N,
$Y_3$ may be $C(R_{33})$ or N,
$Y_4$ may be $C(R_{34})$ or N,
$Y_5$ may be $C(R_{35})$ or N,
$Y_6$ may be $C(R_{36})$ or N,
$Y_7$ may be $C(R_{37})$ or N,
$Y_8$ may be $C(R_{38})$ or N,
$Y_9$ may be $C(R_{39})$ or N,
$Y_{10}$ may be $C(R_{40})$ or N,
$Y_{11}$ may be $C(R_{41})$ or N,
$Y_{12}$ may be $C(R_{42})$ or N,
in Formula 2-1, at least one of $Y_1$ to $Y_6$ may be N,
in Formulae 2-2 and 2-3, at least one of $Y_1$ to $Y_8$ may be N,
in Formulae 2-4 to 2-16, at least one of $Y_1$ to $Y_{10}$ may be N,
in Formula 2-17, at least one of $Y_1$ to $Y_{12}$ may be N, and
$R_{1a}$, $R_{1b}$, $R_{2a}$, $R_{2b}$, and $R_{31}$ to $R_{42}$ may respectively be understood by referring to the descriptions of $R_{10a}$ provided herein.

In Formulae 1-1 to 1-3, $X_1$ may be $C(R_{21})$ or N, $X_2$ may be $C(R_{22})$ or N, and $X_3$ may be $C(R_{23})$ or N.

In some exemplary embodiments, $X_1$ may be $C(R_{21})$, $X_2$ may be $C(R_{22})$, and $X_3$ may be N;
$X_1$ may be $C(R_{21})$, $X_3$ may be $C(R_{23})$, and $X_2$ may be N;
$X_2$ may be $C(R_{22})$, $X_3$ may be $C(R_{23})$, and $X_1$ may be N;

$X_1$ and $X_2$ may each be N, and $X_3$ may be $C(R_{23})$;
$X_1$ and $X_3$ may each be N, and $X_2$ may be $C(R_{22})$;
$X_2$ and $X_3$ may each be N, and $X_1$ may be $C(R_{21})$; or
$X_1$, $X_2$, and $X_3$ may each be N.

In some exemplary embodiments, $X_1$ and $X_2$ may each be N, and $X_3$ may be $C(R_{23})$;
$X_1$ and $X_3$ may each be N, and $X_2$ may be $C(R_{22})$;
$X_2$ and $X_3$ may each be N, and $X_1$ may be $C(R_{21})$; or
$X_1$, $X_2$, and $X_3$ may each be N.

In one or more exemplary embodiments, $X_1$, $X_2$, and $X_3$ may each be N.

In Formulae 2-1 to 2-17, at least one of $R_{1a}$, $R_{1b}$, $R_{2a}$, $R_{2b}$, and $R_{31}$ to $R_{42}$ may be a binding site to an adjacent atom.

In Formulae 1-1 to 1-3, $L_1$ to $L_3$ may each independently be a single bond, a $C_5$-$C_{30}$ carbocyclic group unsubstituted or substituted with at least one $R_{20a}$, or a $C_2$-$C_{30}$ heterocyclic group unsubstituted or substituted with at least one $R_{20a}$.

In some exemplary embodiments, $L_1$ to $L_3$ may each independently be selected from:
a single bond; and
a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group, each unsubstituted or substituted with at least one $R_{20a}$.

In one or more exemplary embodiments, $L_1$ to $L_3$ may each independently be selected from:
a single bond; and
a benzene group, a naphthalene group, a carbazole group, an anthracene group, a phenanthrene group, a triphenylene group, a pyrene group, a fluorene group, a dibenzothiophene group, and a dibenzofuran group, each unsubstituted or substituted with at least one $R_{20a}$.

In Formulae 1-1 to 1-3, a1 to a3 may each independently be an integer from 1 to 5.

In some exemplary embodiments, a1 and a2 may each be 1.

In one or more exemplary embodiments, a3 may be 1.

In Formulae 1-1 to 1-3, $R_1$ and $R_2$ may each independently be selected from hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, a π electron-rich $C_3$-$C_{60}$ cyclic group unsubstituted or substituted with at least one $R_{30a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), In some exemplary embodiments, $R_1$ and $R_2$ may each independently be hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a n electron-rich $C_3$-$C_{60}$ cyclic group unsubstituted or substituted with at least one $R_{30a}$.

In some exemplary embodiments, Formulae 1-1 to 1-3 may satisfy at least one of Conditions 1 to 3:
Condition 1
wherein $R_1$ may be a π electron-rich $C_3$-$C_{60}$ cyclic group unsubstituted or substituted with at least one $R_{30a}$,
Condition 2
wherein $R_2$ may be a π electron-rich $C_3$-$C_{60}$ cyclic group unsubstituted or substituted with at least one $R_{30a}$, and
Condition 3
wherein $R_1$ and $R_2$ may each independently be a π electron-rich $C_3$-$C_{60}$ cyclic group unsubstituted or substituted with at least one $R_{30a}$.

In some exemplary embodiments, in Formulae 1-1 to 1-3, a group represented by *-$(L_1)_{a1}$-$R_1$ and a group represented by *-$(L_2)_{a2}$-$R_2$ may satisfy at least one of Conditions 1a to 3a:
Condition 1a
wherein the group represented by *-$(L_1)_{a1}$-$R_1$ may be selected from: a π electron-rich $C_3$-$C_{60}$ cyclic group unsubstituted or substituted with at least one $R_{30a}$; and groups represented by Formulae 3-1 to 3-10,
Condition 2a
wherein the group represented by *-$(L_2)_{a2}$-$R_2$ may be selected from: a R electron-rich $C_3$-$C_{60}$ cyclic group unsubstituted or substituted with at least one $R_{30a}$; and groups represented by Formulae 3-1 to 3-10,
Condition 3a
wherein the group represented by *-$(L_1)_{a1}$-$R_1$ and the group represented by *-$(L_2)_{a2}$-$R_2$ may each independently be selected from: a π electron-rich $C_3$-$C_{60}$ cyclic group unsubstituted or substituted with at least one $R_{30a}$; and groups represented by Formulae 3-1 to 3-10,

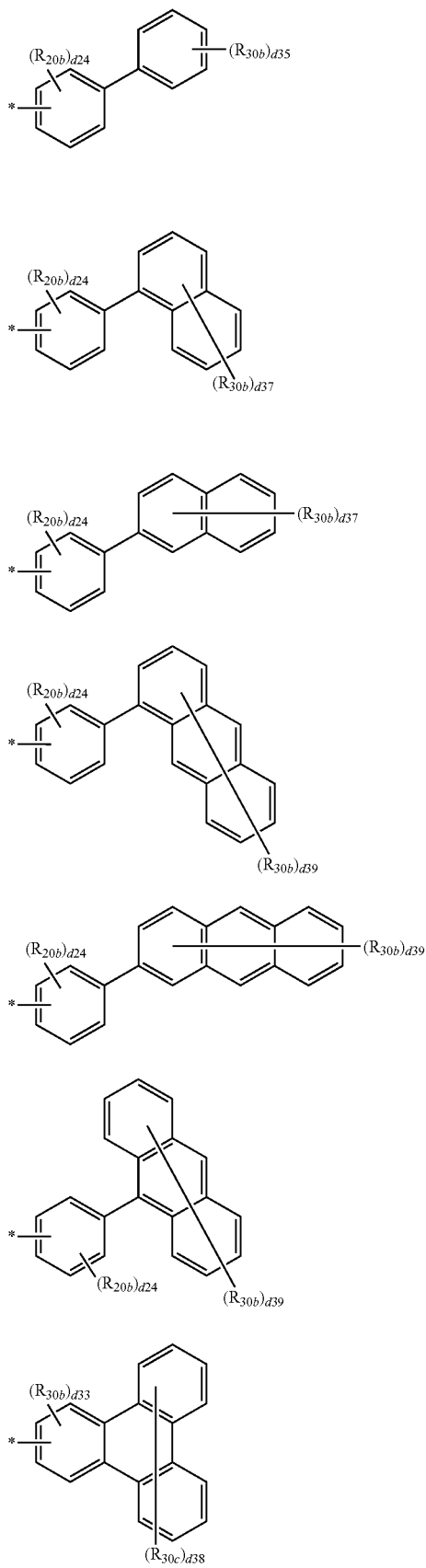
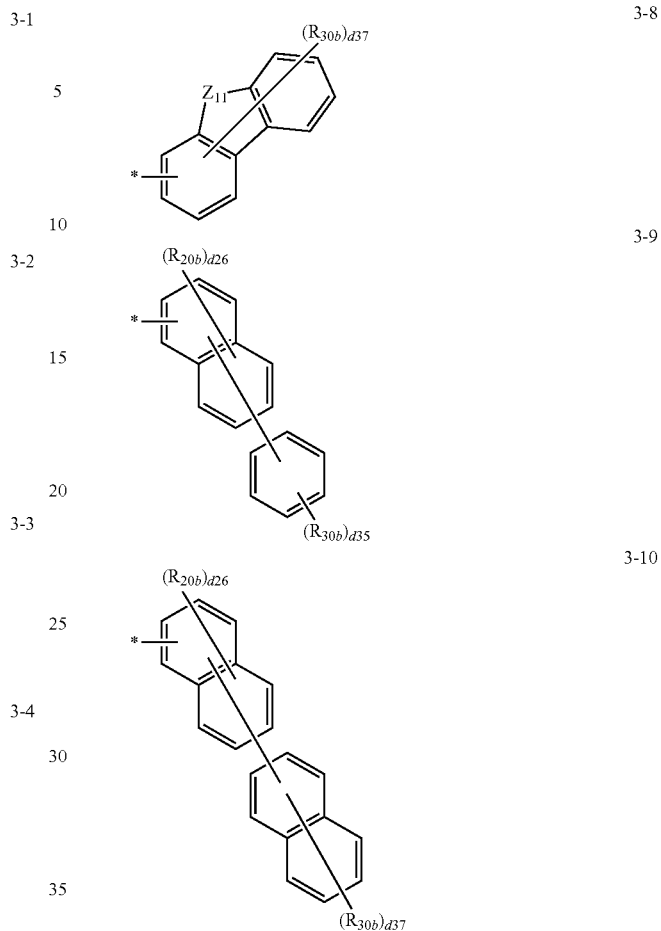

wherein, in Formulae 3-1 to 3-10, $Z_1$ may be O, S, $N(R_{11a})$, $C(R_{11a})(R_{11b})$, or $Si(R_{11a})(R_{11b})$, $R_{20b}$ may be understood by referring to the description of $R_{20a}$ provided herein, $R_{30b}$ and $R_{30c}$ may each be understood by referring to the description of $R_{30a}$ provided herein, d24 may be an integer from 0 to 4,
d26 may be an integer from 0 to 6,
d33 may be an integer from 0 to 3,
d35 may be an integer from 0 to 5,
d37 may be an integer from 0 to 7,
d38 may be an integer from 0 to 8,
* indicates a binding site to an adjacent atom, and
$R_{11a}$ and $R_{11b}$ may each be understood by referring to the description of $R_{30a}$ provided herein, In some exemplary embodiments, the π electron-rich $C_3$-$C_{60}$ cyclic group may be a) a second ring or b) a condensed ring in which at least two second rings are condensed, and the second ring may be a benzene group, a cyclopentadiene group, a pyrrole group, a furan group, a thiophene group, or a silole group.

In one or more exemplary embodiments, the π electron-rich $C_3$-$C_{60}$ cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonapthothiophene group, (an indolo)phenanthrene group, a (benzofurano)phenanthrene group, or a (benzothieno)phenanthrene group.

In Formulae 1-1 to 1-3, $R_{10}$ to $R_{13}$, $R_{10a}$, $R_{20a}$, $R_{30a}$, and $R_{21}$ to $R_{23}$ may each independently be selected from hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium (-D), —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazine group, a hydrazone group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each unsubstituted or substituted with at least one selected from deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be selected from: hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic condensed polycyclic group; a monovalent non-aromatic condensed heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

In some exemplary embodiments, $R_{10}$ to $R_{13}$, $R_{10a}$, $R_{20a}$, $R_{30a}$, and $R_{21}$ to $R_{23}$ may each independently be selected from:

hydrogen, deuterium, —F, —Cl, —Br, —I, a hydroxyl group, a cyano group, a nitro group, an amidino group, a hydrazine group, a hydrazone group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, and an azadibenzosilolyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —$Si(Q_{31})(Q_{32})(Q_{33})$, —$N(Q_{31})(Q_{32})$, —$B(Q_{31})(Q_{32})$, —$P(Q_{31})(Q_{32})$, —$C(=O)(Q_{31})$, —$S(=O)_2(Q_{31})$, and —$P(=O)(Q_{31})(Q_{32})$; and —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, wherein $Q_1$ to $Q_3$ and $Q_{31}$ to $Q_{33}$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, and a triazinyl group, each unsubstituted or substituted with at least one selected from deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

In some exemplary embodiments, $R_{10}$ to $R_{13}$, $R_{10a}$, $R_{20a}$, $R_{30a}$, and $R_{21}$ to $R_{23}$ may each independently be selected from:
hydrogen, deuterium, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —$CD_3$, —$CD_2H$, —$CDH_2$, $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, and a naphthyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a carbazolyl group, a benzofuranyl group, a benzothiophenyl group, a dibenzofuranyl group, a dibenzothiophenyl group, a benzocarbazolyl group, and a dibenzocarbazolyl group, each unsubstituted or substituted with at least one selected from deuterium, —$CD_3$, —$CD_2H$, —$CDH_2$, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an isoindolyl group, an indolyl group, an indazolyl group, a purinyl group, a carbazolyl group, a benzofuranyl group, a benzothiophenyl group, a dibenzofuranyl group, a dibenzothiophenyl group, a benzocarbazolyl group, a dibenzocarbazolyl group, —$Si(Q_{31})(Q_{32})(Q_{33})$, and —$N(Q_{31})(Q_{32})$, —$B(Q_{31})(Q_{32})$; and —$Si(Q_1)(Q_2)(Q_3)$, —$N(Q_1)(Q_2)$ and —$B(Q_1)(Q_2)$, wherein $Q_1$ to $Q_3$ and $Q_{31}$ to $Q_{33}$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each unsubstituted or substituted with at least one selected from deuterium, a C$_1$-C$_{10}$ alkyl group, a phenyl group, and a biphenyl group.

In some exemplary embodiments, R$_{10}$ to R$_{13}$ may each independently be selected from:

hydrogen, deuterium, —F, —Cl, —Br, —I, a hydroxyl group, a cyano group, a nitro group, an amidino group, a hydrazine group, a hydrazone group, a C$_1$-C$_{10}$ alkyl group, a C$_2$-C$_{10}$ alkenyl group, a C$_2$-C$_{10}$ alkynyl group, and a C$_1$-C$_{10}$ alkoxy group;

a C$_1$-C$_{10}$ alkyl group, a C$_2$-C$_{10}$ alkenyl group, a C$_2$-C$_{10}$ alkynyl group, and a C$_1$-C$_{10}$ alkoxy group, each substituted with at least one of deuterium, —F, —Cl, —Br, —I, —CD$_3$, —CD$_2$H, —CDH$_2$, C$_1$-C$_{10}$ alkyl group, a phenyl group, a biphenyl group, and a naphthyl group; and —Si(Q$_1$)(Q$_2$)(Q$_3$), —N(Q$_1$)(Q$_2$), —B(Q$_1$)(Q$_2$), —C(=O)(Q$_1$), —S(=O)$_2$(Q$_1$), and —P(=O)(Q$_1$)(Q$_2$), wherein Q$_1$ to Q$_3$ may each independently be selected from:

hydrogen; deuterium; —F; —Cl; —Br; —I; a hydroxyl group; a cyano group; a nitro group; an amidino group; a hydrazine group; a hydrazone group; a C$_1$-C$_{20}$ alkyl group; a C$_2$-C$_{20}$ alkenyl group; a C$_2$-C$_{20}$ alkynyl group; a C$_1$-C$_{20}$ alkoxy group; a C$_3$-C$_{10}$ cycloalkyl group; a C$_1$-C$_{10}$ heterocycloalkyl group; a C$_3$-C$_{10}$ cycloalkenyl group; a C$_1$-C$_{10}$ heterocycloalkenyl group; a C$_6$-C$_{30}$ aryl group; a C$_1$-C$_{30}$ heteroaryl group; a monovalent non-aromatic condensed polycyclic group; a monovalent non-aromatic condensed heteropolycyclic group; a C$_1$-C$_{20}$ alkyl group substituted with at least one selected from deuterium, —F, and a cyano group; a C$_6$-C$_{30}$ aryl group substituted with at least one selected from deuterium, —F, and a cyano group; a biphenyl group; and a terphenyl group.

In Formulae 1-1 to 1-3, d10 may be an integer from 0 to 7.

In some exemplary embodiments, the heterocyclic compound may be selected from Compounds 1 to 32, but the exemplary embodiments are not limited thereto:

1

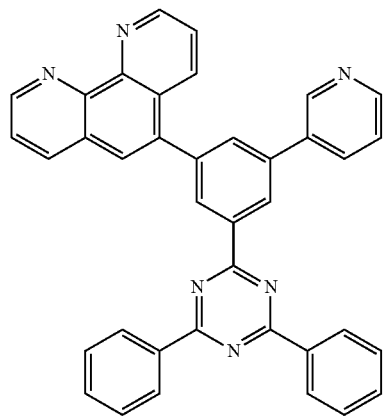

2

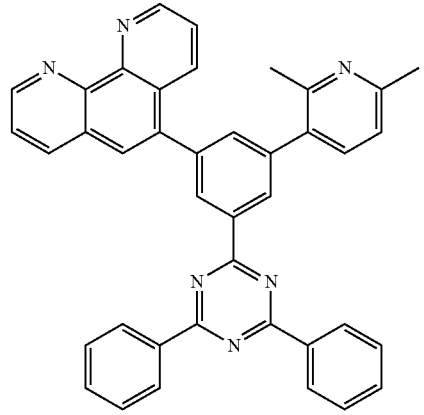

3

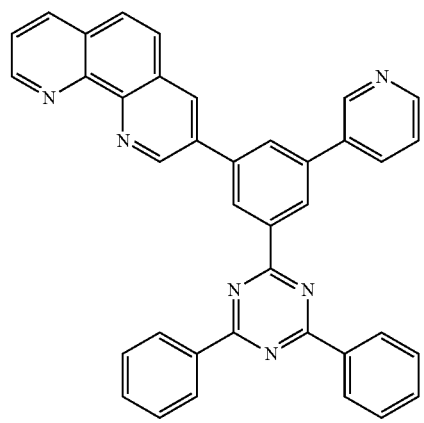

4

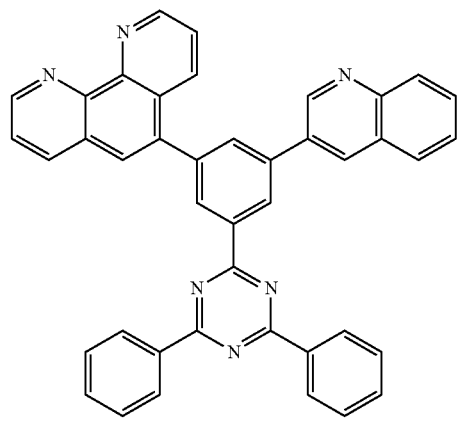

5
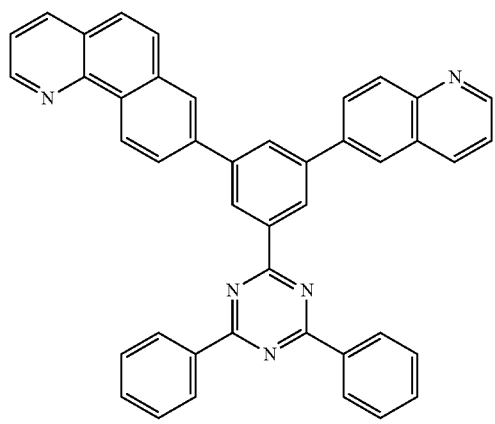
6
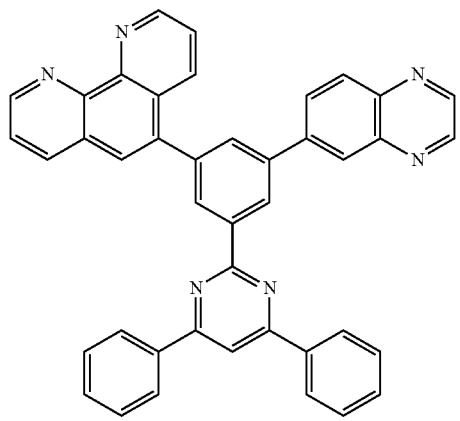
7
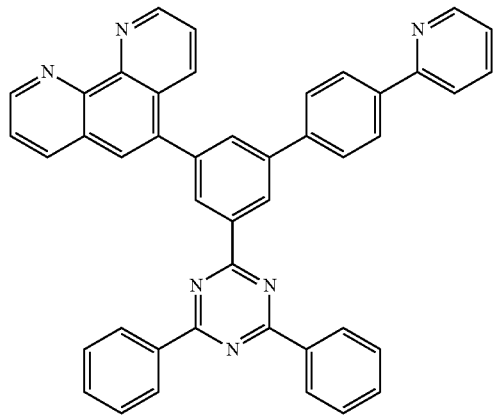
8
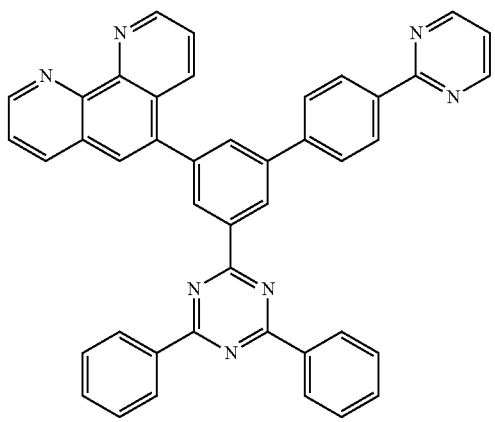
9
10
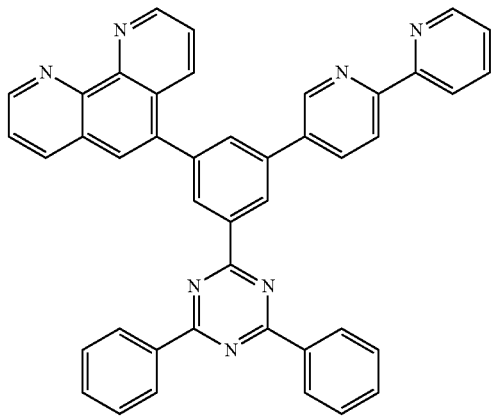

-continued
11
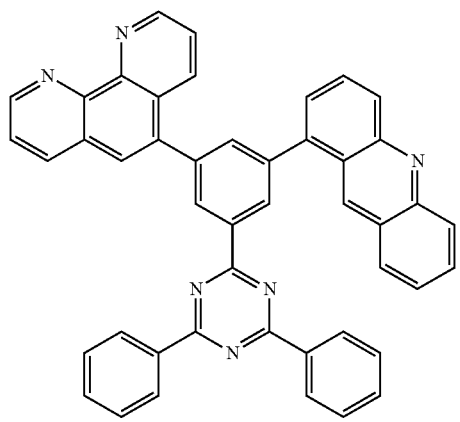
12
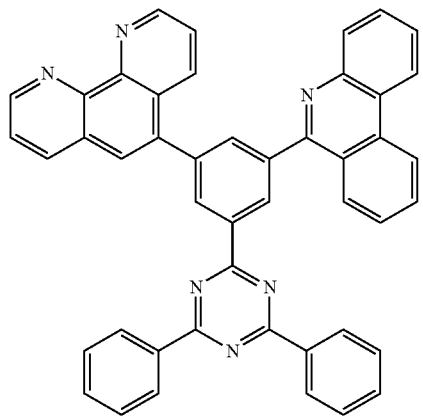
13
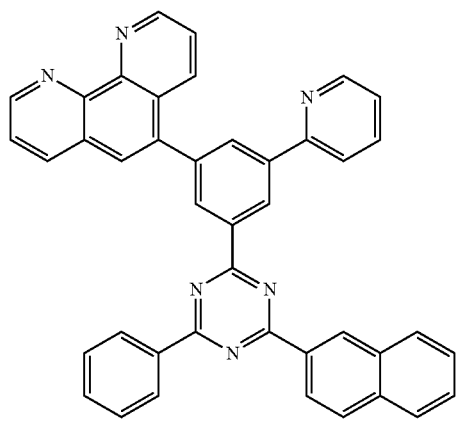
-continued
14
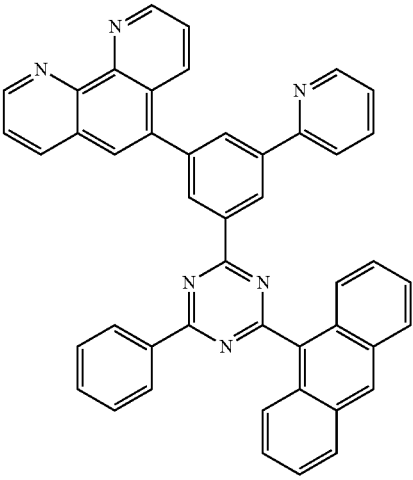
15
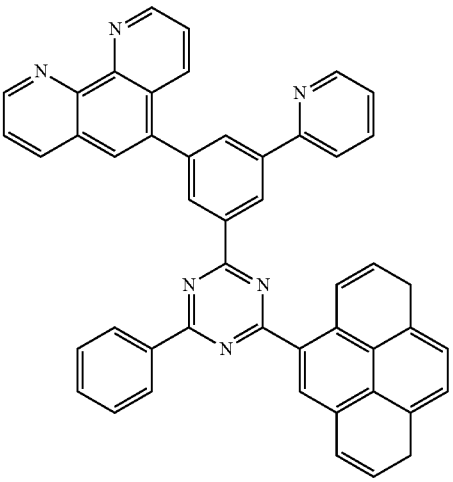
16
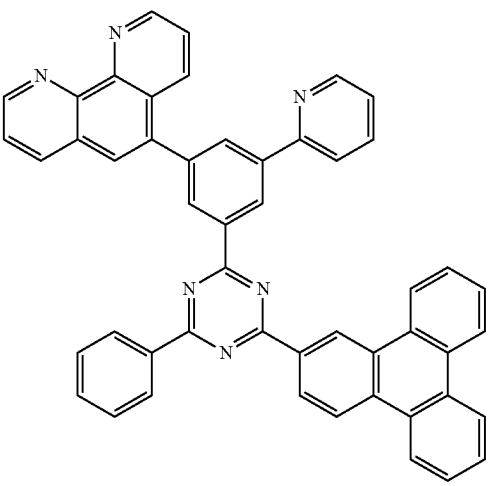

17
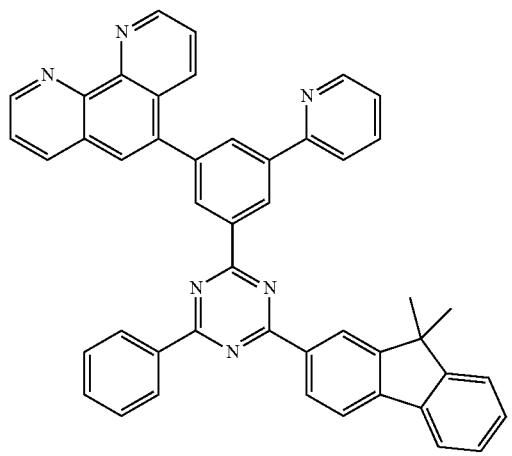
18
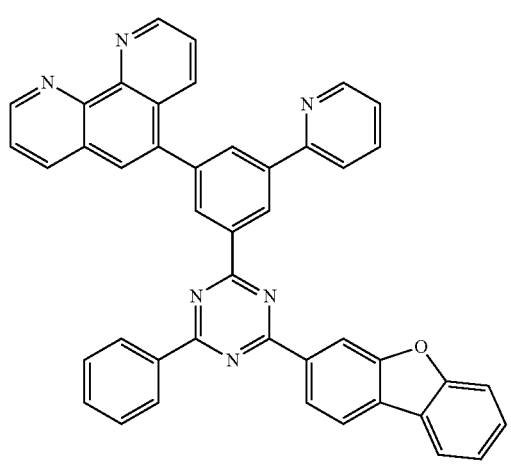
19
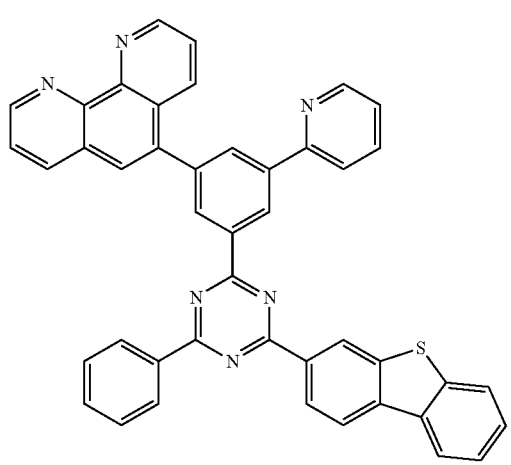
20
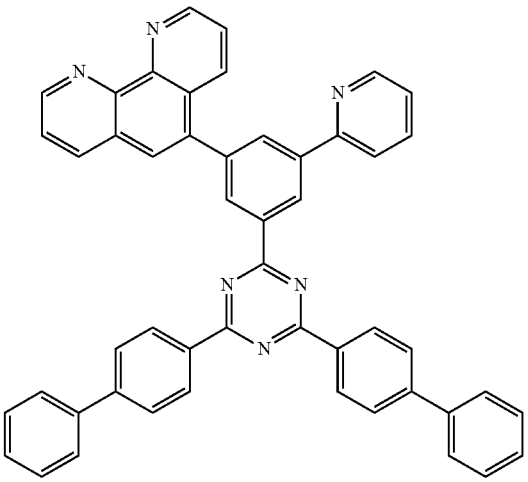
21
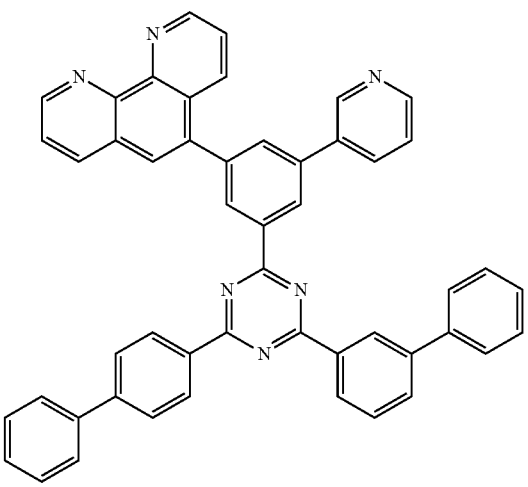
22
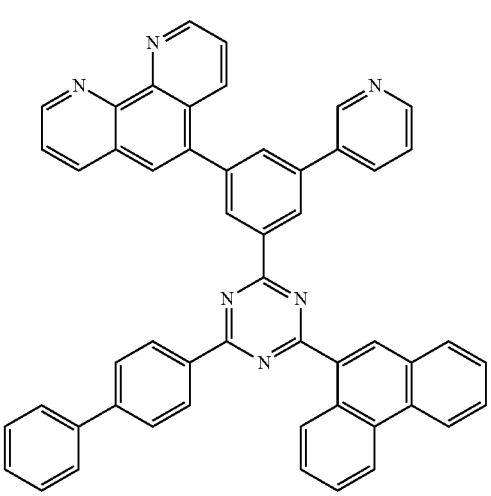

-continued
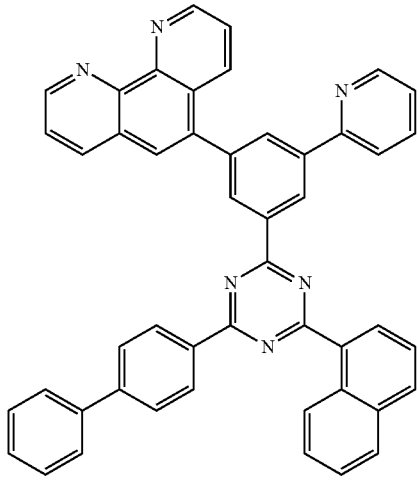
23
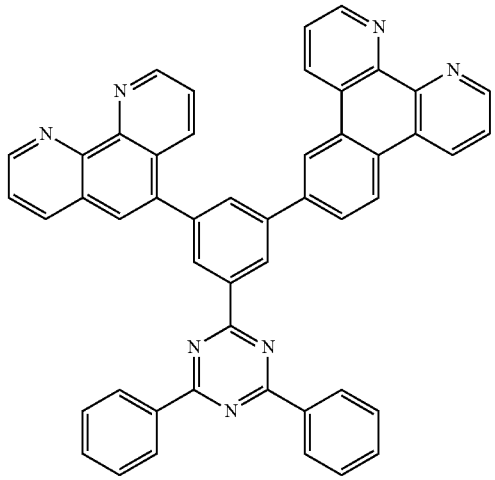
26
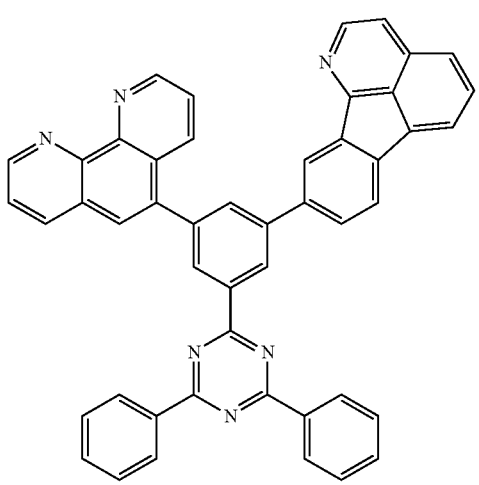
24
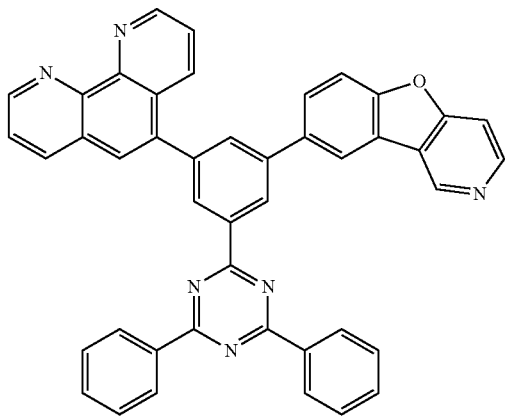
27
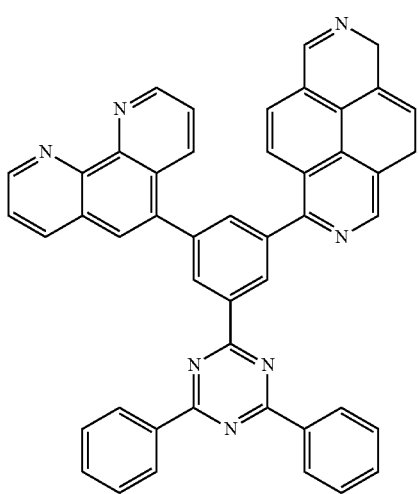
25
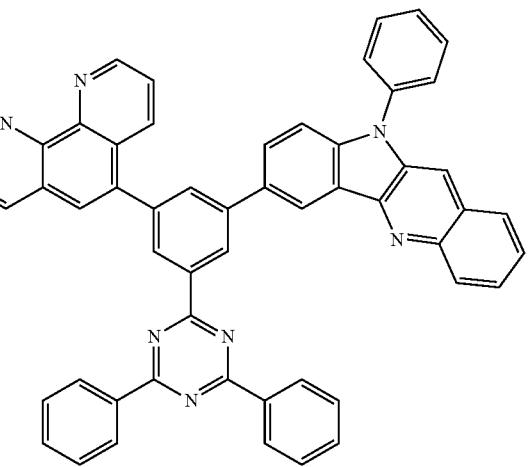
28

-continued

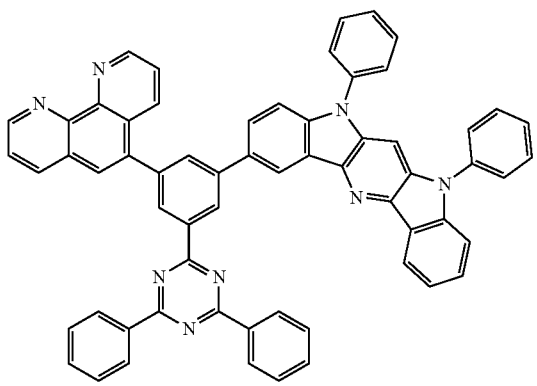

29

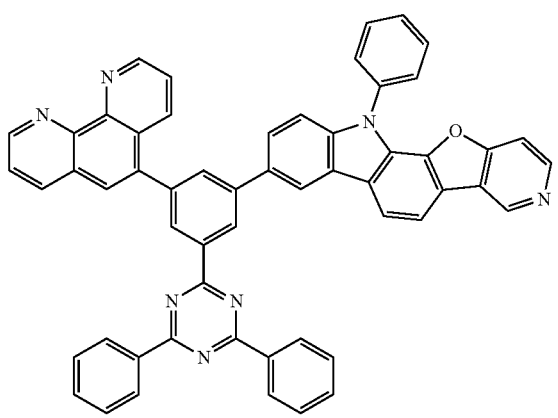

30

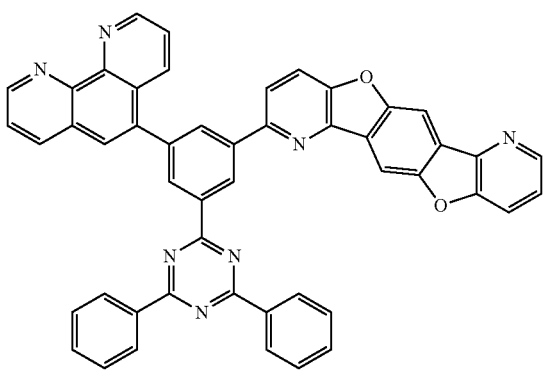

31

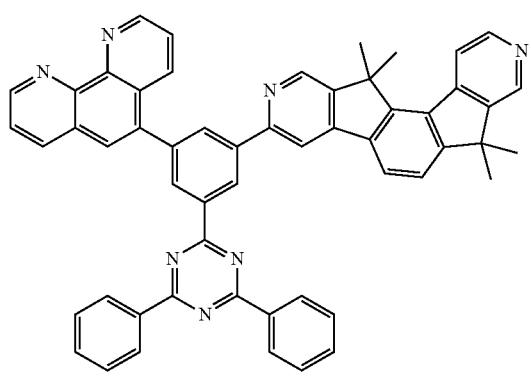

32

The heterocyclic compounds represented by Formulae 1-1 to 1-3 may have a structure in which a phenyl linker is linked to C-2 to C-7 in a phenanthroline group, and the phenyl linker with a phenanthroline group and a π electron-depleted nitrogen-containing $C_1$-$C_{60}$ cyclic group in a meta position is included:

In Formulae 1-1 to 1-3, as a phenyl linker is linked to C-2 to C-7 in a phenanthroline group, a greater dipole moment may be obtained. Thus, intermolecular interaction may be increased, thus facilitating intermolecular stacking.

As Formulae 1-1 to 1-3 include the phenyl linker with a phenanthroline group and a π electron-depleted nitrogen-containing $C_1$-$C_{60}$ cyclic group in a meta position, electron accepting ability may be increased, and electron transportability may be improved. That is, electron mobility may be improved to improve the efficiency and lower the driving voltage.

Therefore, an electronic device, e.g., an organic light-emitting device, employing the heterocyclic compound represented by one of Formulae 1-1 to 1-3 may have a low driving voltage, high maximum quantum yield, and long lifespan.

Methods of synthesizing the heterocyclic compound represented by one of Formulae 1-1 to 1-3 should be readily apparent to those of ordinary skill in the art by referring to Examples described herein.

At least one of the heterocyclic compounds represented by Formulae 1-1 to 1-3 may be included between a pair of electrodes in an organic light-emitting device. In some exemplary embodiments, the heterocyclic compound may be included in an emission layer. In some exemplary embodiments, the heterocyclic compound represented by one of Formulae 1-1 to 1-3 may be used as a material for forming a capping layer, which is disposed on outer sides of a pair of electrodes in an organic light-emitting device.

According to one or more exemplary embodiments, an organic light-emitting device may include: a first electrode; a second electrode facing the first electrode; an organic layer between the first electrode and the second electrode and including an emission layer; and at least one of the heterocyclic compounds represented by Formulae 1-1 to 1-3.

For example, the organic layer may include only Compound 1 as the heterocyclic compound. In some exemplary embodiments, Compound 1 may be included in the emission layer of the organic light-emitting device. In some exemplary embodiments, the organic layer may include Compounds 1 and 2 as the heterocyclic compounds. In some exemplary embodiments, Compounds 1 and 2 may be included in the same layer (for example, both Compounds 1 and 2 may be included in an emission layer) or in different layers (for example, Compound 1 may be included in an emission layer, and Compound 2 may be included in an electron transport layer).

In some exemplary embodiments, the first electrode may be an anode, the second electrode may be a cathode, and the organic layer may include the heterocyclic compound, and the organic layer may further include a hole transport region between the first electrode and the emission layer and an electron transport region between the emission layer and the second electrode.

In some exemplary embodiments, the hole transport region may include a hole injection layer, a hole transport layer, an emission auxiliary layer, an electron blocking layer, or a combination thereof, and the electron transport region may include a hole blocking layer, an electron transport layer, an electron injection layer, or a combination thereof.

In some exemplary embodiments, the electron transport region may be included in the heterocyclic compound. In some exemplary embodiments, the electron transport region may include an electron transport layer, and the heterocyclic compound may be included in the electron transport layer.

In some exemplary embodiments, the electron transport region may include a hole blocking layer, and the hole blocking layer may include the heterocyclic compound. In some exemplary embodiments, the electron transport region may further include an electron injection layer, and the heterocyclic compound may be included in the electron injection layer.

In some exemplary embodiments, the hole transport region may include a compound represented by Formula 201 or Formula 202:

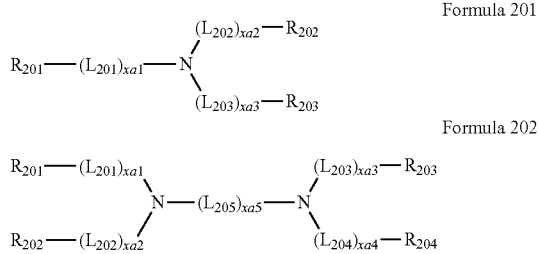

Formula 201

Formula 202 wherein, in Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some exemplary embodiments, the electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof. In some exemplary embodiments, the emission layer may include an antracence-based compound.

In some exemplary embodiments, the emission layer may include the heterocyclic compound. In some exemplary embodiments, the emission layer may include a host and a dopant, the host may be different from the dopant, a content of the host may be greater than a content of the dopant, and the dopant may include the heterocyclic compound. In some exemplary embodiments, the emission layer may include a host and a dopant, the host may be different from the dopant, a content of the host may be greater than a content of the dopant, and the host may include the heterocyclic compound.

In some exemplary embodiments, a second capping layer may be further included on the second electrode, and the second capping layer may include an organic matter, an inorganic matter, or any combination thereof.

In some exemplary embodiments, the second capping layer may include at least one selected from a carbocyclic compound, a heterocyclic compound, an amine group-containing compound, a porphine derivative, a phthalocyanine derivative, a naphthalocyanine derivative, an alkali metal complex, an alkaline earth metal complex, a silicon-based inorganic matter, a silicon-based organic matter, an acrylic compound, and an epoxy compound.

In some exemplary embodiments, an organic light-emitting device may include: a first electrode; a second electrode facing the first electrode; m emission units stacked between the first electrode and the second electrode, each including at least one emission layer; and m−1 charge generating layers, each between two adjacent emission units from among the m emission units, wherein m may be an integer of 2 or greater, and at least one of the m−1 charge generating layers may include at least one of the heterocyclic compounds described above.

In the organic light-emitting device, m may be 2 or 3, but the exemplary embodiments are not limited thereto. As discussed hereinafter, FIG. 5 may be referred to some exemplary embodiments of an organic light-emitting device, when m is 2, and FIG. 6 may be referred to some exemplary embodiments of an organic light-emitting device, when m is 3.

In some exemplary embodiments, the organic light-emitting device may have i) a first electrode/organic layer/second electrode/second capping layer structure, ii) a first capping layer/first electrode/organic layer/second electrode structure, or iii) a first capping layer/first electrode/organic layer/second electrode/second capping layer structure, wherein layers of each structure are sequentially stacked in each stated order. At least one of the first capping layer and the second capping layer may include the heterocyclic compound.

Description of FIG. 1

Figure 1:
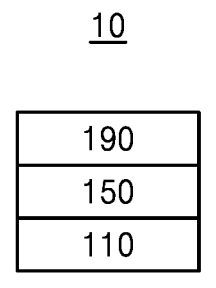

FIG. 1 is a schematic cross-sectional diagram of an exemplary embodiment of an organic light-emitting device constructed according to principles of the invention.

The organic light-emitting device 10 may include a first electrode 110, an organic layer 150, and a second electrode 190. Hereinafter, the structure of the organic light-emitting device 10 according to some exemplary embodiments and a method of manufacturing an organic light-emitting device according to some exemplary embodiments will be described in connection with FIG. 1.

First Electrode 110

In FIG. 1, a substrate may be additionally located under the first electrode 110 or above the second electrode 190. The substrate may be a glass substrate or a plastic substrate, each having excellent mechanical strength, thermal stability, transparency, surface smoothness, ease of handling, and water resistance. The first electrode 110 may be formed by depositing or sputtering, onto the substrate, a material for forming the first electrode 110. When the first electrode 110 is an anode, the material for forming the first electrode 110 may be selected from materials with a high work function that facilitate hole injection.

The first electrode 110 may be a reflective electrode, a semi-transmissive electrode, or a transmissive electrode. When the first electrode 110 is a transmissive electrode, a material for forming the first electrode 110 may be selected from an indium tin oxide (ITO), an indium zinc oxide (IZO), a tin oxide ($SnO_2$), a zinc oxide (ZnO), and any combinations thereof, but the exemplary embodiments are not limited thereto. In some exemplary embodiments, when the first electrode 110 is a semi-transmissive electrode or a reflective electrode, as a material for forming the first electrode 110, at least one of magnesium (Mg), silver (Ag), aluminum (Al), aluminum-lithium (Al—Li), calcium (Ca), magnesium-indium (Mg—In), magnesium-silver (Mg—Ag), and any combination thereof may be used, but the exemplary embodiments are not limited thereto. The first electrode 110 may have a single-layered structure, or a multi-layered structure including two or more layers. In some exemplary embodiments, the first electrode 110 may have a triple-layered structure of ITO/Ag/ITO, but the exemplary embodiments are not limited thereto.

Organic Layer 150

The organic layer 150 may be on the first electrode 110. The organic layer 150 may include an emission layer. The organic layer 150 may further include a hole transport region between the first electrode 110 and the emission layer and an electron transport region between the emission layer and the second electrode 190.

Hole Transport Region in Organic Layer 150

The hole transport region may have i) a single-layered structure consisting of a single layer consisting of a single material, ii) a single-layered structure consisting of a single layer including a plurality of different materials, or iii) a multi-layered structure having a plurality of layers including a plurality of different materials. The hole transport region may include at least one selected from a hole injection layer, a hole transport layer, an emission auxiliary layer, and an electron blocking layer.

For example, the hole transport region may have a single-layered structure including a single layer including a plurality of different materials or a multi-layered structure, e.g., a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/ electron blocking layer structure, wherein layers of each structure are sequentially stacked on the first electrode 110 in each stated order, but the exemplary embodiments are not limited thereto.

The hole transport region may include at least one selected from 4,4',4"-tris[phenyl(m-tolyl)amino]triphenylamine (m-MTDATA), 1-N,1-N-bis[4-(diphenylamino)phenyl]-4-N,4-N-diphenylbenzene-1,4-diamine (TDATA), 4,4',4"-tris[2-naphthyl(phenyl)amino]triphenylamine (2-TNATA), N,N'-di(1-naphthyl)-N,N'-diphenyl-(1,1'-biphenyl)-4,4'-diamine (NPB or NPD), N4,N4'-di(naphthalen-2-yl)-N4,N4'-diphenyl-[1,1'-biphenyl]-4,4'-diamine (P—NPB), N,N'-bis(3-methylphenyl)-N,N'-diphenylbenzidine (TPD), N,N'-bis(3-methylphenyl)-N,N'-diphenyl-9,9-spirobifluorene-2,7-diamine (spiro-TPD), N2,N7-di-1-naphthalenyl-N2,N7-diphenyl-9,9'-spirobi[9H-fluorene]-2,7-diamine (spiro-NPB), N, N,N'-di(1-naphthyl)-N,N'-2,2'dimethyldiphenyl-(1,1'-biphenyl)-4,4'-diamine (methylated-NPB), 4,4'-cyclohexylidene bis[N,N-bis(4-methylphenyl)benzenamine] (TAPC), N,N,N',N'-tetrakis(3-methylphenyl)-3,3'-dimethylbenzidine (HMTPD), 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (PANI/PSS), a compound represented by Formula 201, and a compound represented by Formula 202:

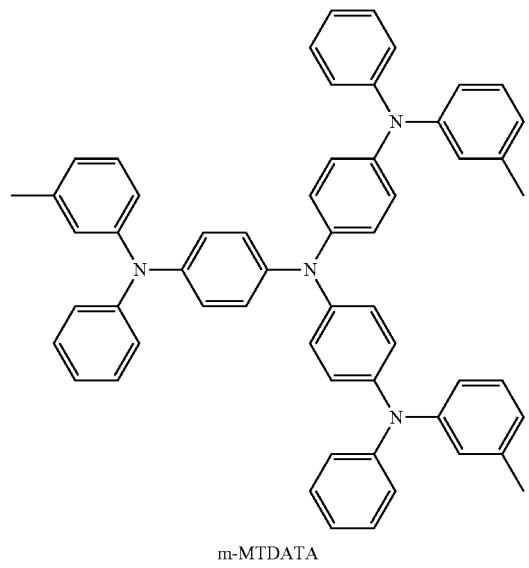

m-MTDATA

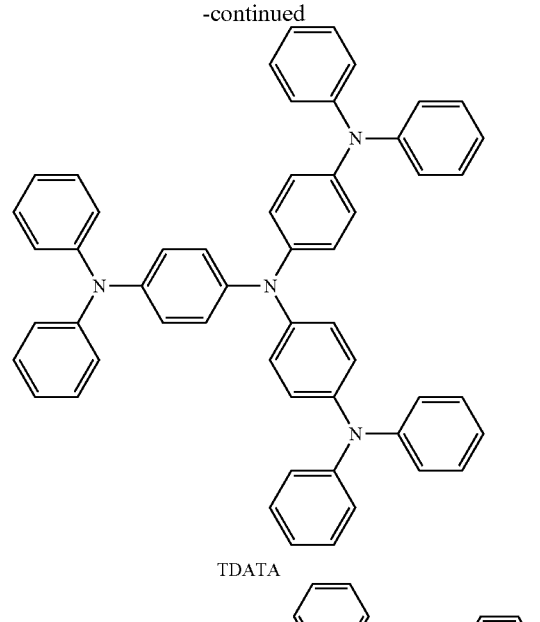
TDATA
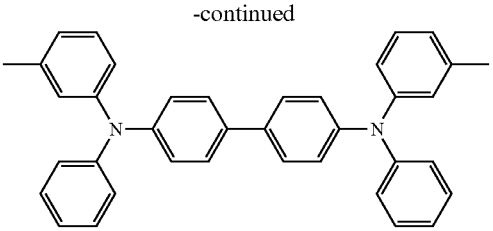
TPD
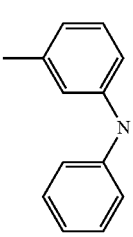
2-TNATA
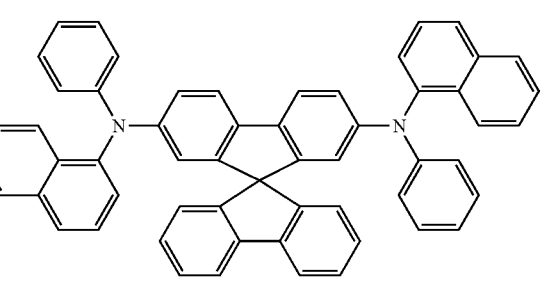
Spiro-TPD
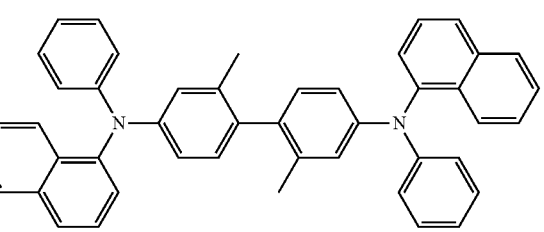
Spiro-NPB
NPB
methylated NPB
β-NPB
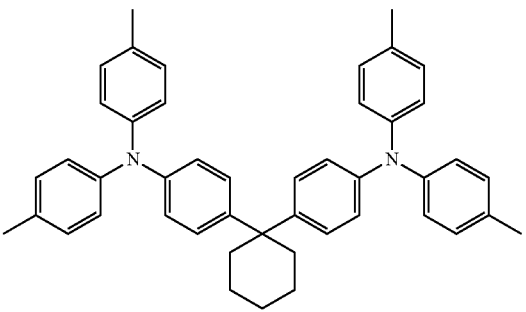
TAPC

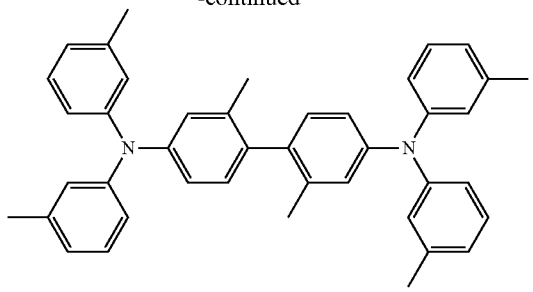

HMTPD

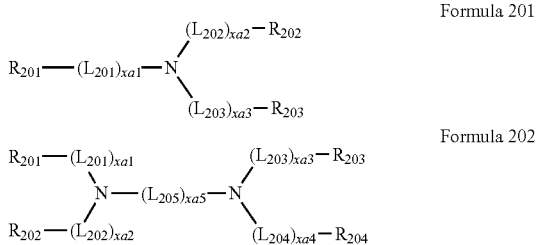

wherein, in Formulae 201 and 202,

L$_{201}$ to L$_{204}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, L$_{205}$ may be selected from *—O—*', *—S—*', *—N(Q$_{201}$)-*', a substituted or unsubstituted C$_1$-C$_{20}$ alkylene group, a substituted or unsubstituted C$_2$-C$_{20}$ alkenylene group, a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and R$_{201}$ to R$_{204}$ and Q$_{201}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

In some exemplary embodiments, in Formula 202, R$_{201}$ and R$_{202}$ may optionally be bound via a single bond, a dimethyl-methylene group, or a diphenyl-methylene group, and R$_{203}$ and R$_{204}$ may optionally be bound via a single bond, a dimethyl-methylene group, or a diphenyl-methylene group.

In some exemplary embodiments, in Formulae 201 and 202, L$_{201}$ to L$_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a C$_1$-C$_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more exemplary embodiments, xa1 to xa4 may each independently be 0, 1, or 2. In one or more exemplary embodiments, xa5 may be 1, 2, 3, or 4.

In one or more exemplary embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may respectively be understood by referring to the descriptions of $Q_{31}$ to $Q_{33}$ provided herein.

In one or more exemplary embodiments, in Formula 201, at least one of $R_{201}$ to $R_{203}$ may be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but the exemplary embodiments are not limited thereto.

In one or more exemplary embodiments, in Formula 202, i) $R_{201}$ and $R_{202}$ may be bound via a single bond, and/or ii) $R_{203}$ and $R_{204}$ may be bound via a single bond. In one or more exemplary embodiments, in Formula 202, at least one of $R_{201}$ to $R_{204}$ may be selected from: a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but the exemplary embodiments are not limited thereto.

The compound represented by Formula 201 may be represented by Formula 201-1:

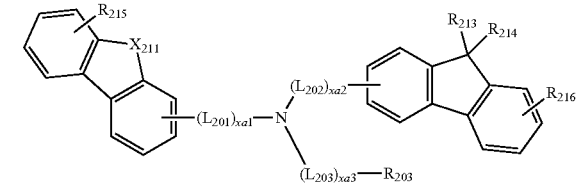

Formula 201-1

In some exemplary embodiments, the compound represented by Formula 201 may be represented by Formula 201-2, but the exemplary embodiments are not limited thereto:

Formula 201-2

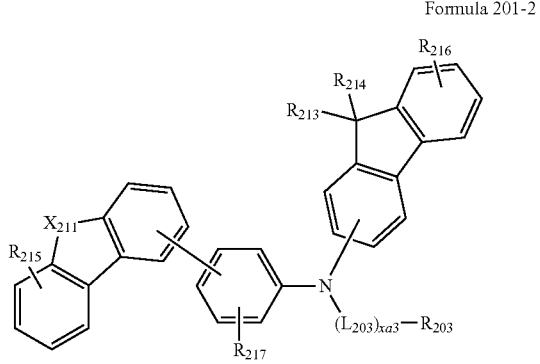

In some exemplary embodiments, the compound represented by Formula 201 may be represented by Formula 201-2(1), but the exemplary embodiments are not limited thereto:

Formula 201-2(1)

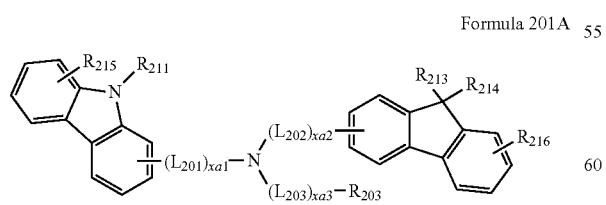

The compound represented by Formula 201 may be represented by Formula 201A:

Formula 201A

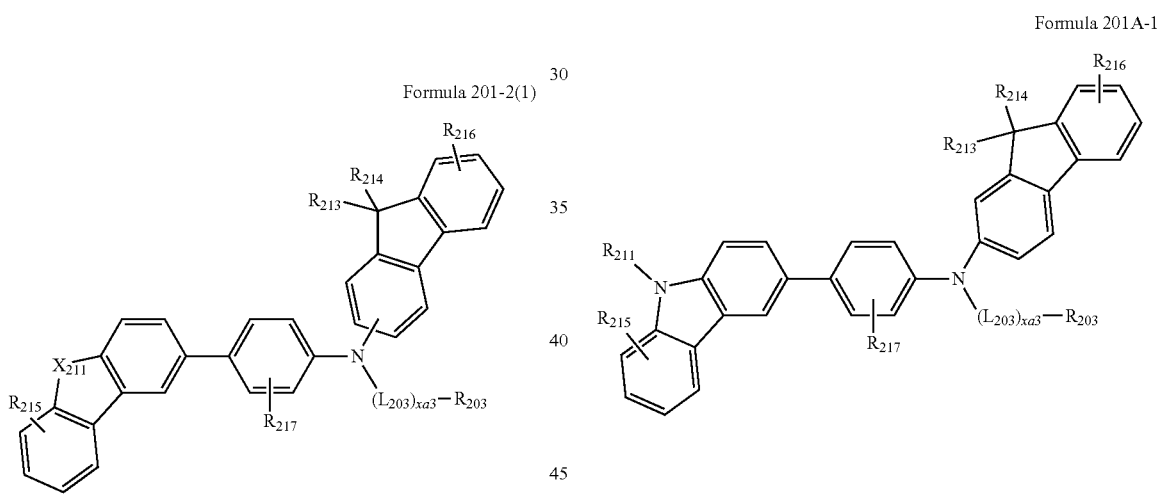

In some exemplary embodiments, the compound represented by Formula 201 may be represented by Formula 201A(1), but the exemplary embodiments are not limited thereto:

Formula 201A(1)

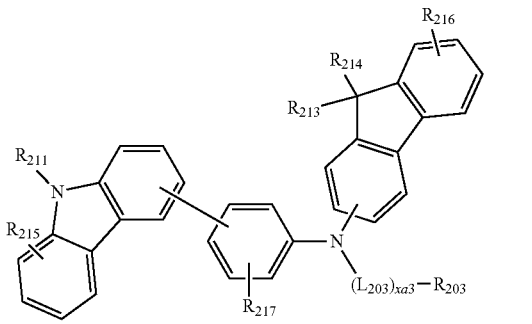

In some exemplary embodiments, the compound represented by Formula 201 may be represented by Formula 201A-1, but the exemplary embodiments are not limited thereto:

Formula 201A-1

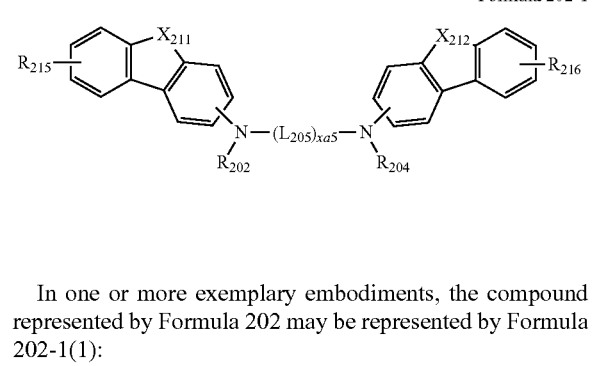

In some exemplary embodiments, the compound represented by Formula 202 may be represented by Formula 202-1:

Formula 202-1

In one or more exemplary embodiments, the compound represented by Formula 202 may be represented by Formula 202-1(1):

Formula 202-1(1)

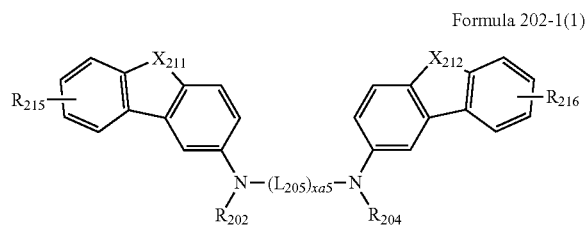

In some exemplary embodiments, the compound represented by Formula 202 may be represented by Formula 202A:

Formula 202A

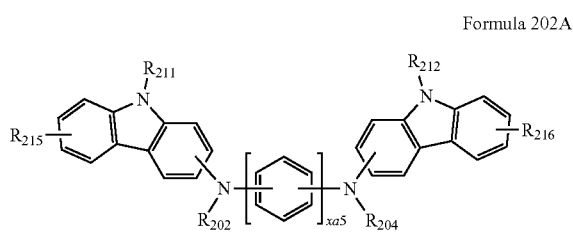

In some exemplary embodiments, the compound represented by Formula 202 may be represented by Formula 202A-1:

Formula 202A-1

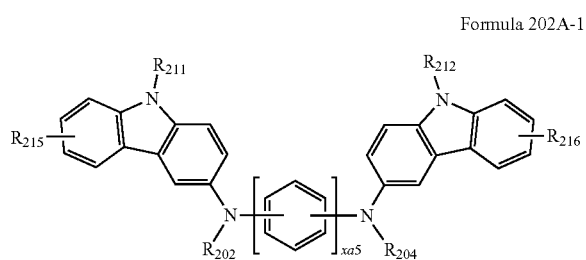

In Formulae 201-1, 201-2, 201-2(1), 201A, 201A(1), 201A-1, 202-1, 202-1(1), 202A, and 202A-1, $L_{201}$ to $L_{203}$, xa1 to xa3, xa5, and $R_{202}$ to $R_{204}$ may respectively be understood by referring to the descriptions of $L_{201}$ to $L_{203}$, xa1 to xa3, xa5, and $R_{202}$ to $R_{204}$ provided herein, $L_{205}$ may be selected from a phenylene group and a fluorenylene group, $X_{211}$ may be selected from O, S, and $N(R_{211})$, $X_{212}$ may be selected from O, S, and $N(R_{212})$, $R_{211}$ and $R_{212}$ may each be understood by referring to the description of $R_{203}$ provided herein, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT48, but the exemplary embodiments are not limited thereto:

HT1

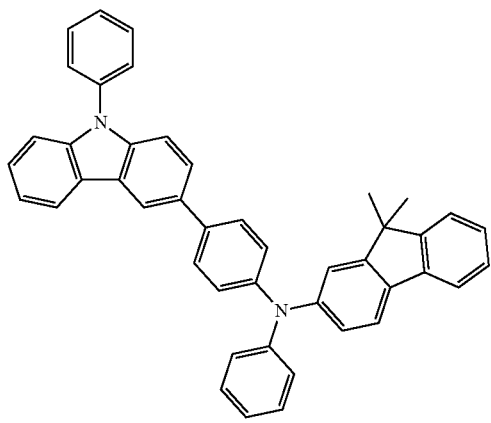

HT2

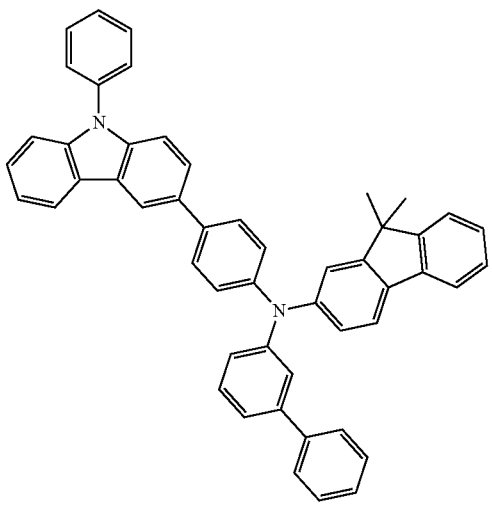

-continued
HT3
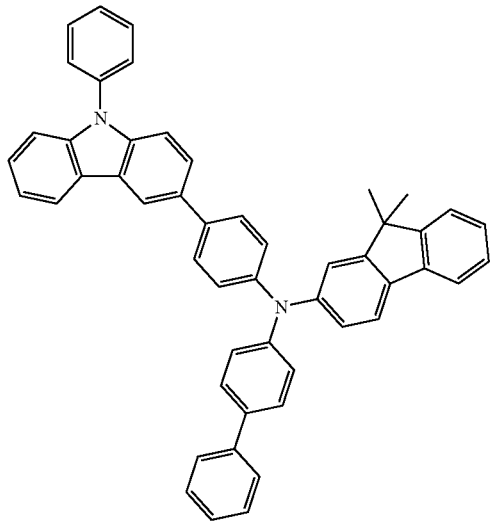
HT4
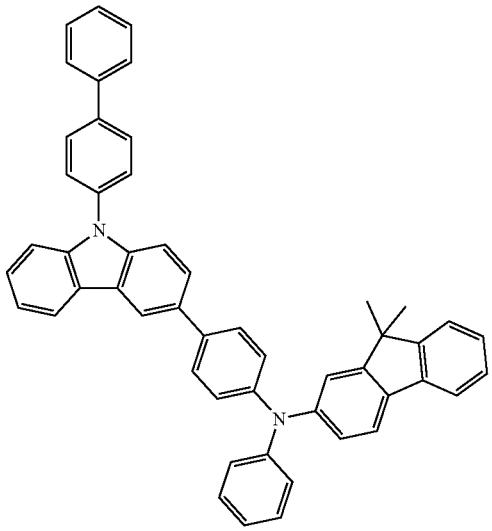
HT5
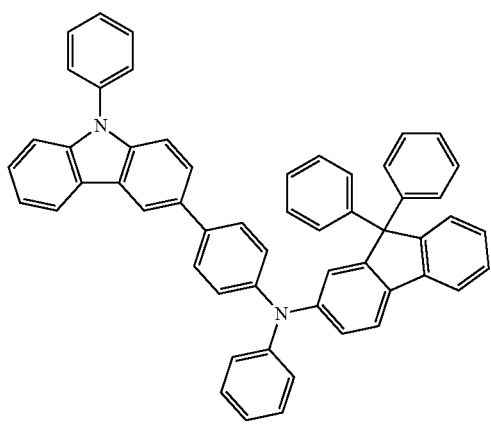
HT6
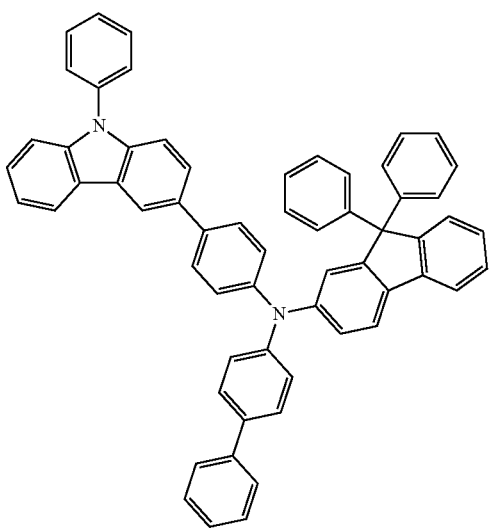
HT7
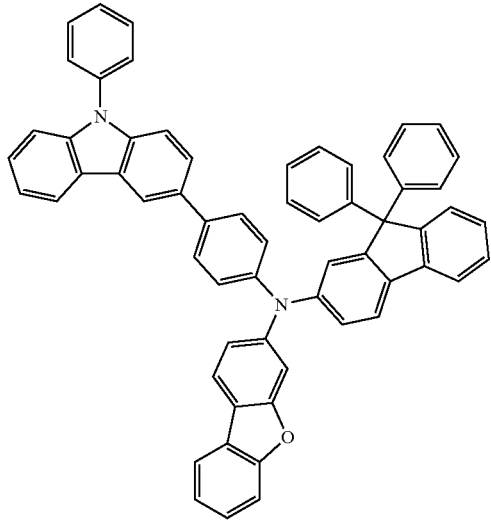
HT8
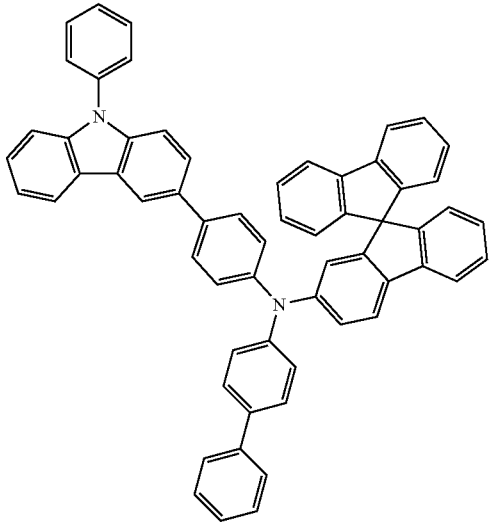

-continued
HT9
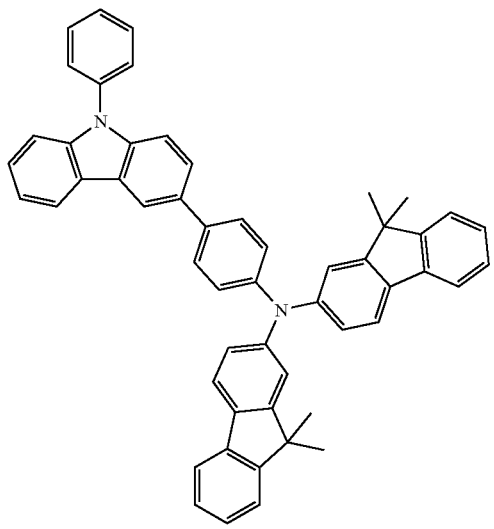
HT10
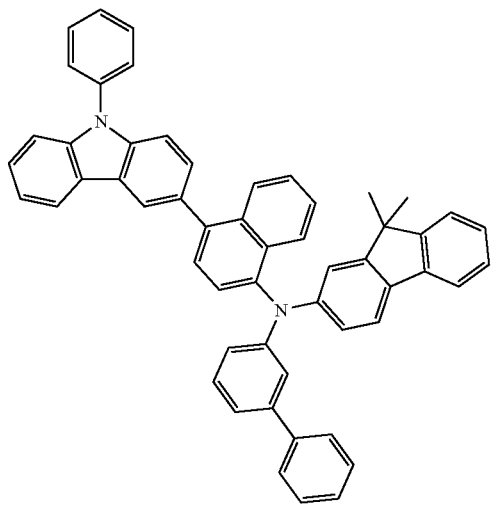
HT11
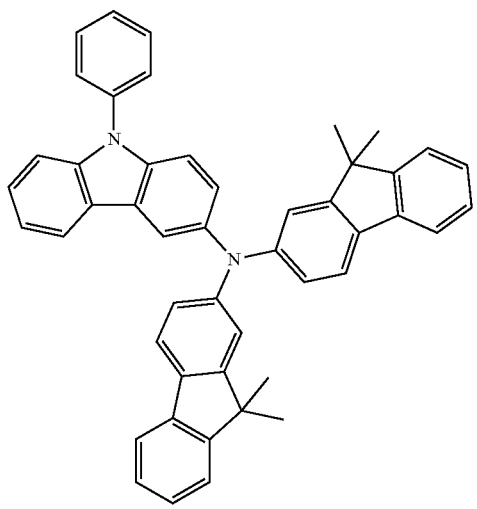
HT12
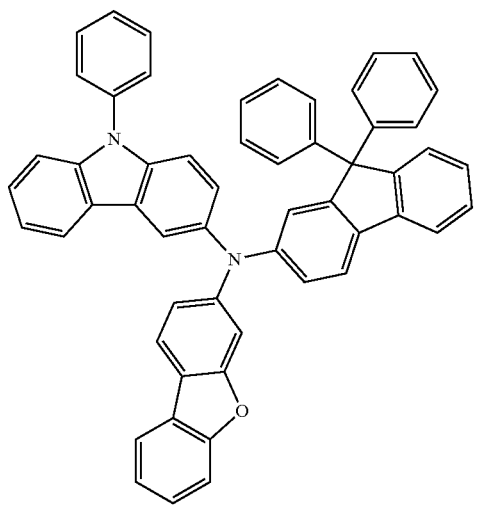
HT13
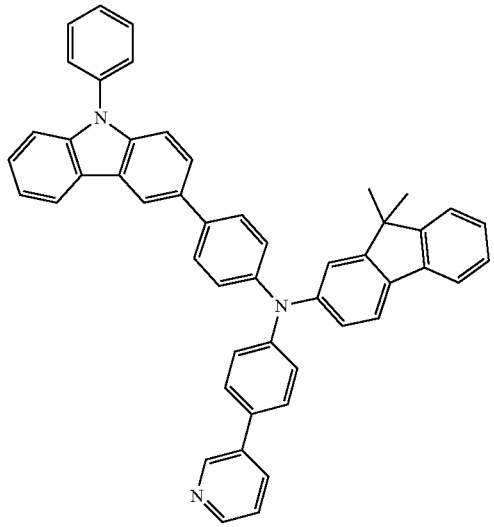
HT14
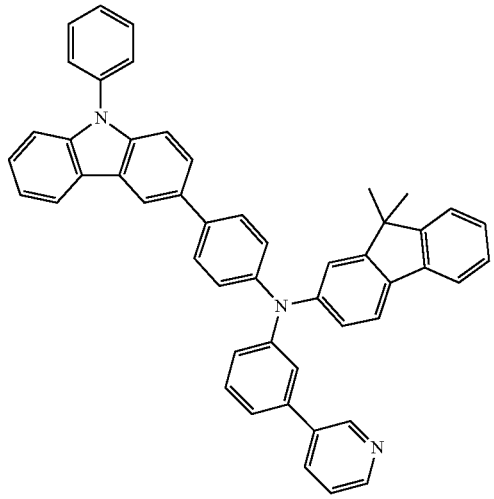

-continued
HT15
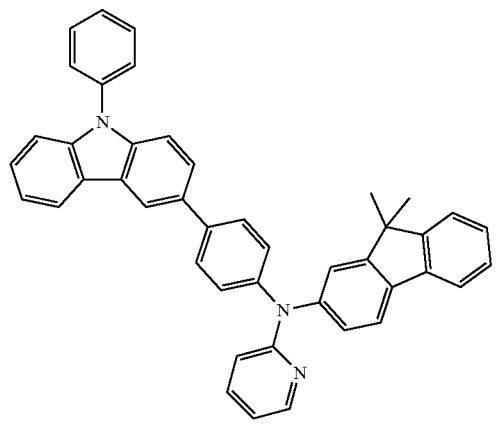
HT16
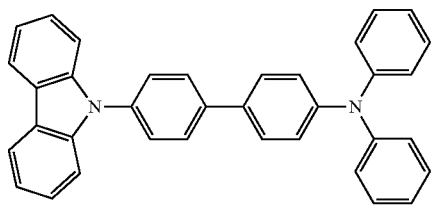
HT17
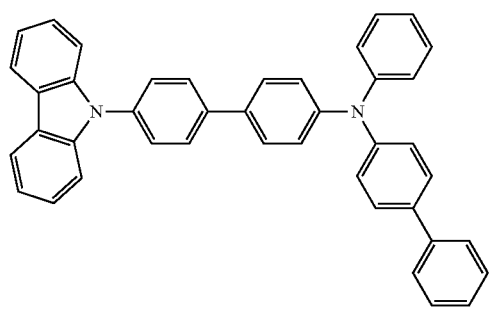
HT18
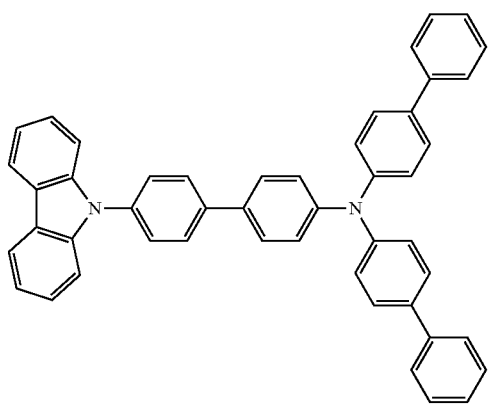
HT19
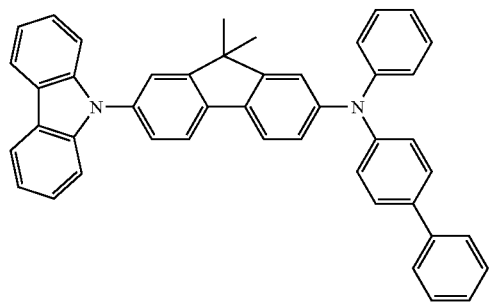
HT20
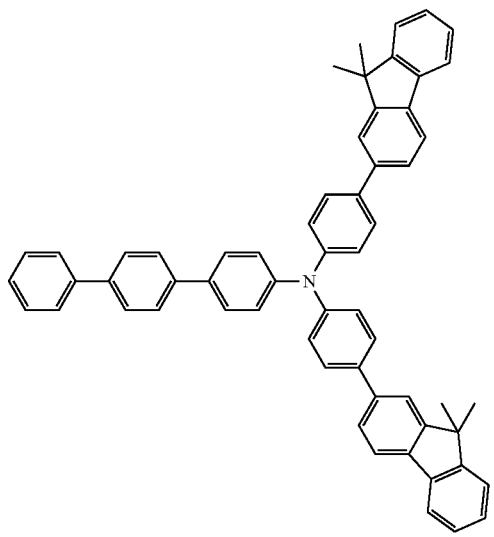

-continued
HT21
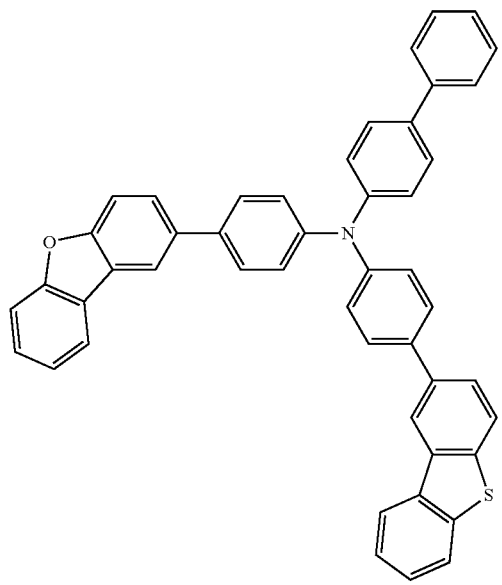
HT22
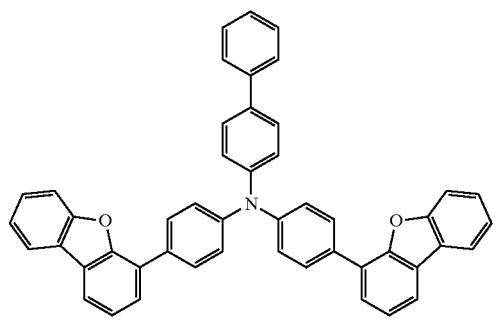
HT23
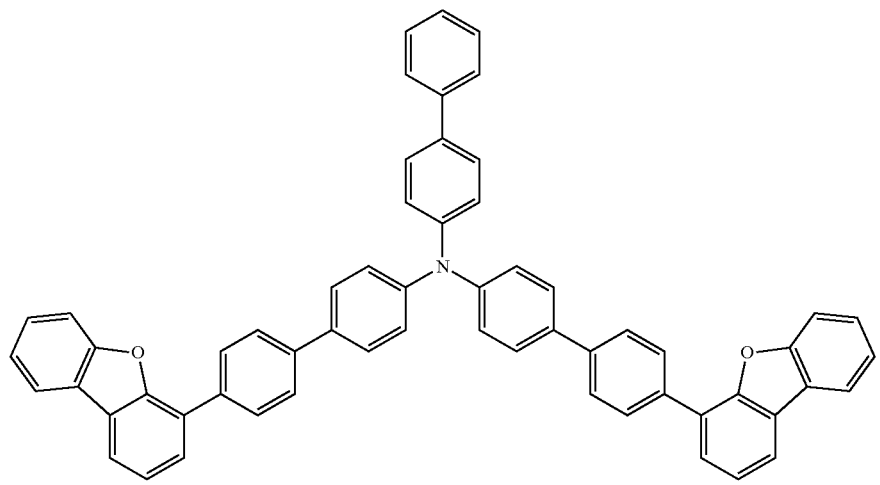
HT24
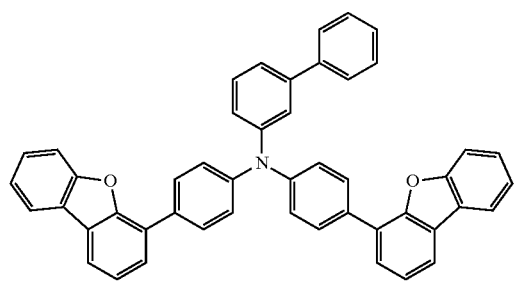
HT25
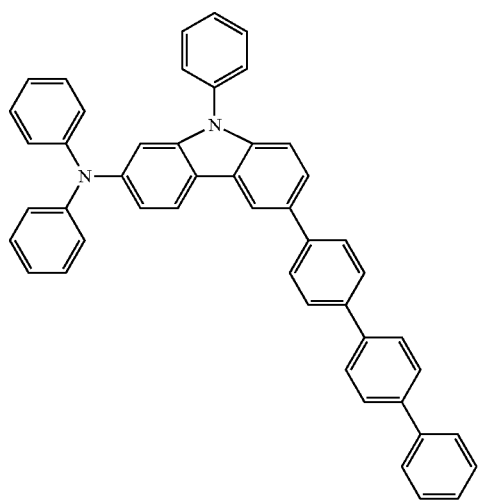

HT26
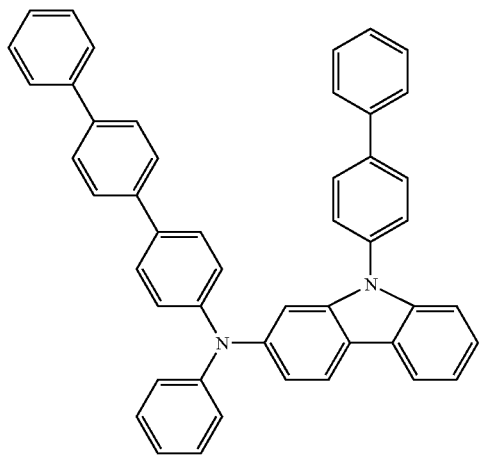
HT27
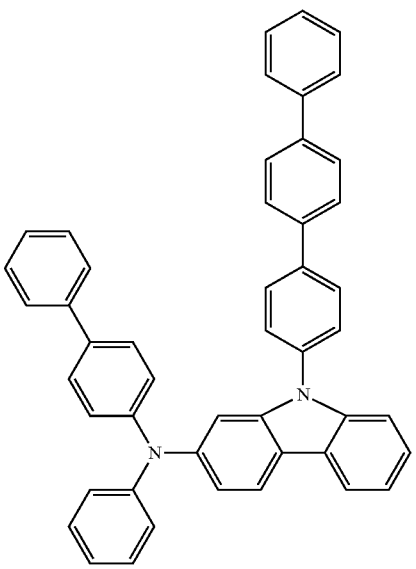
HT28
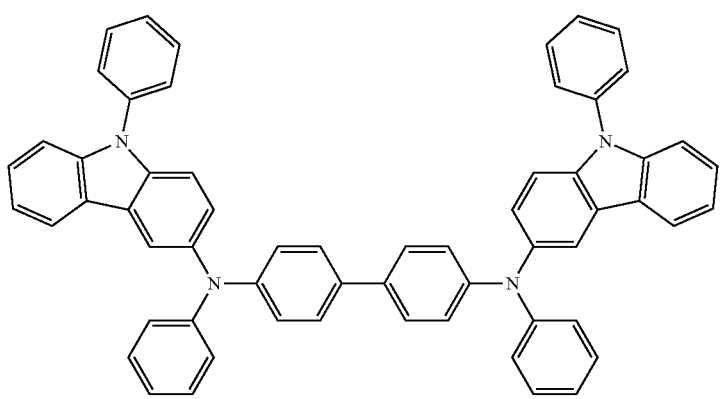
HT29
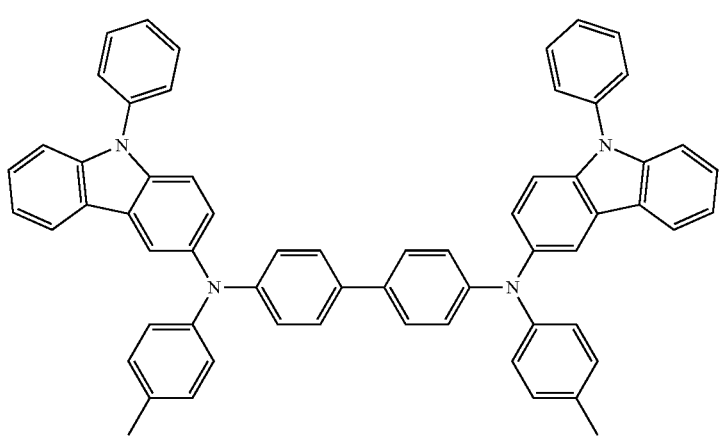

-continued
HT30
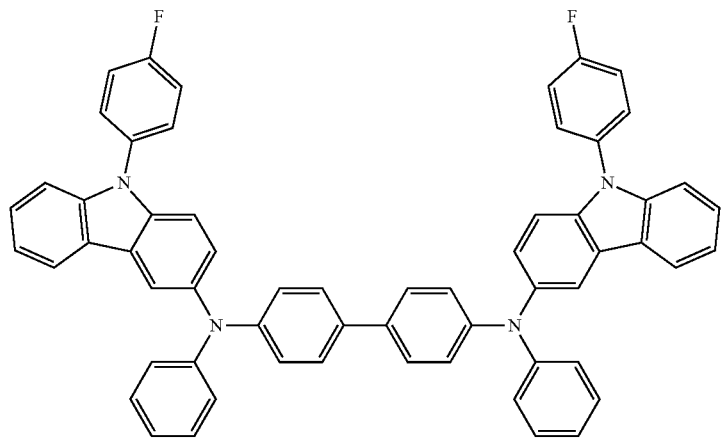
HT31
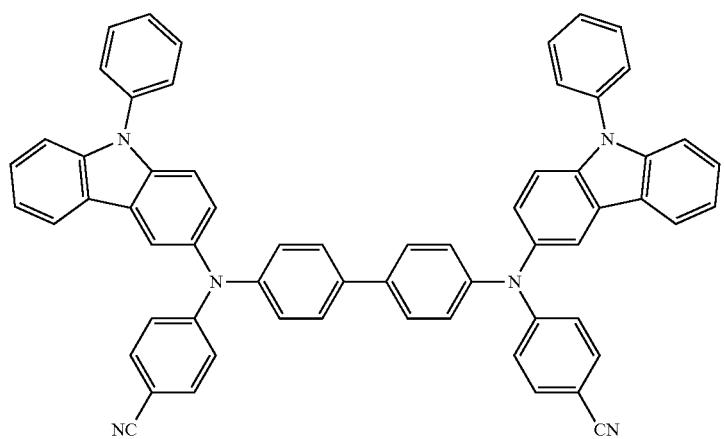
HT32
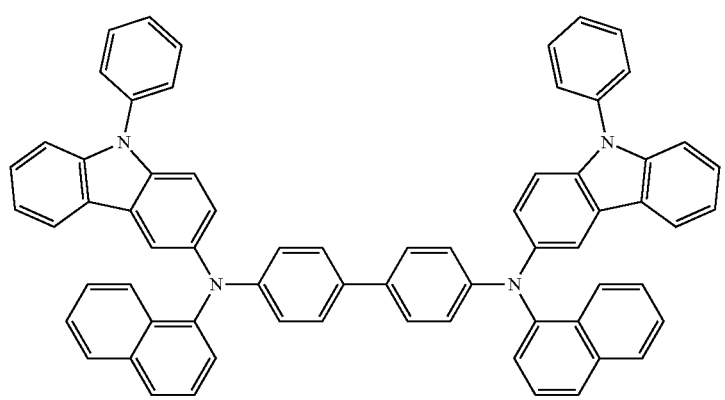

-continued
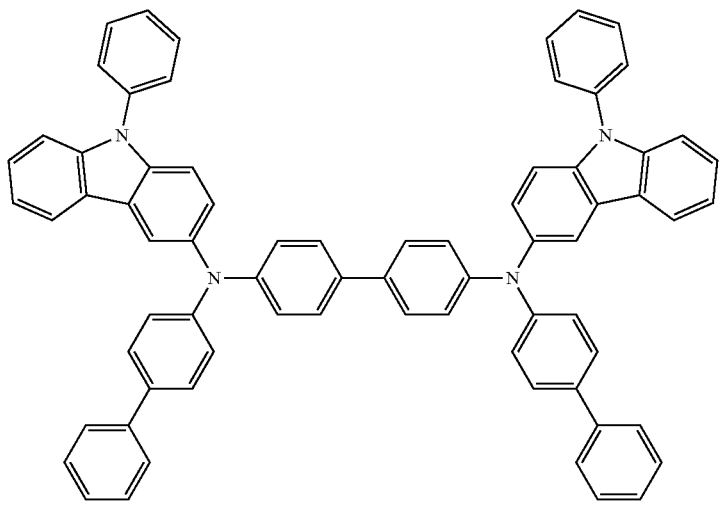
HT33
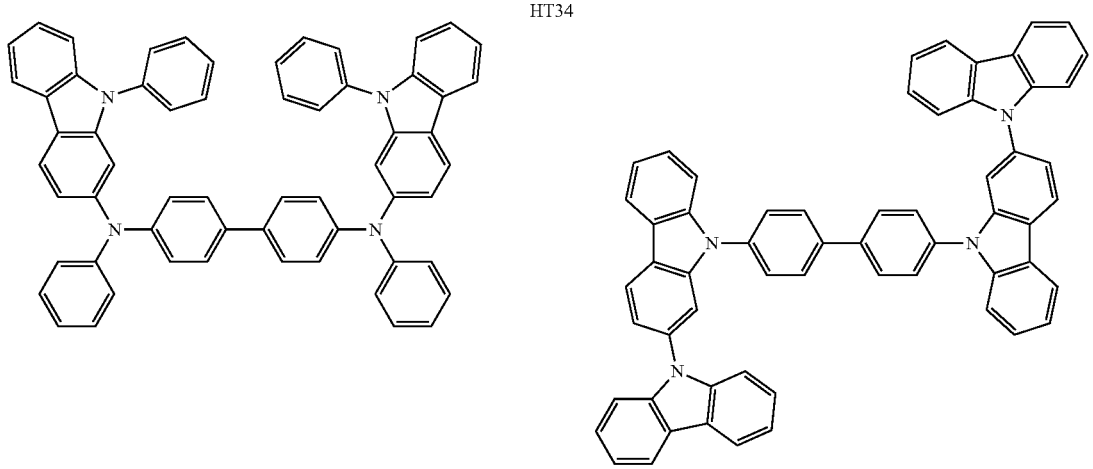
HT34
HT35
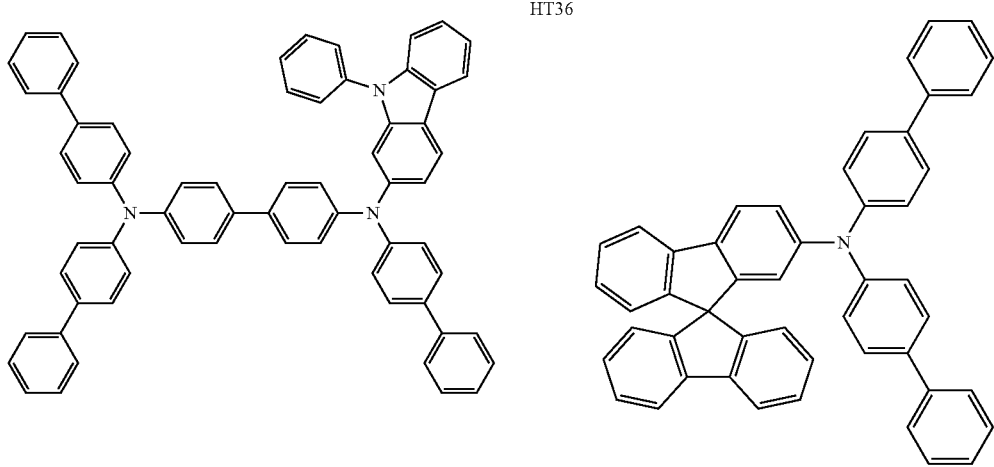
HT36
HT37

-continued
HT38
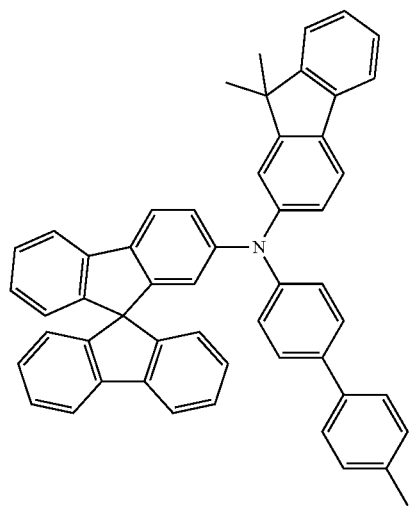
HT39
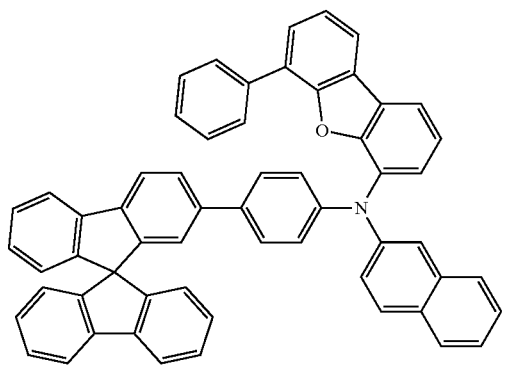
HT40
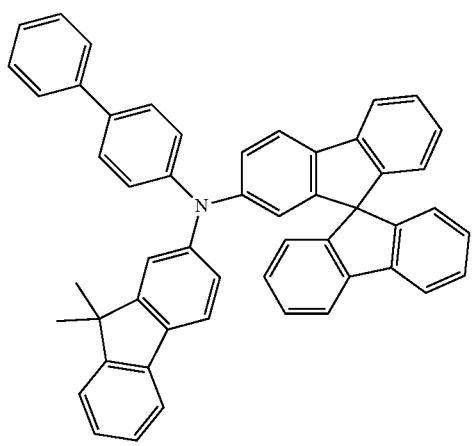
-continued
HT42
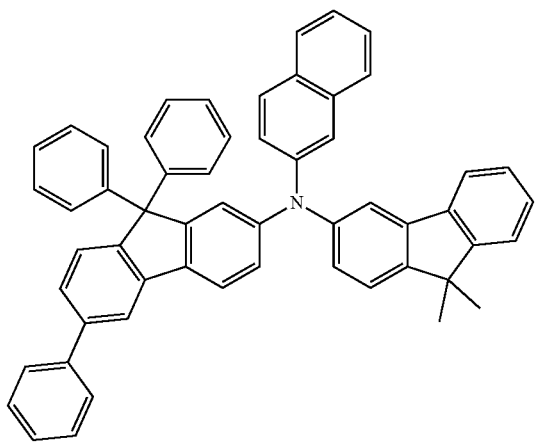
HT41
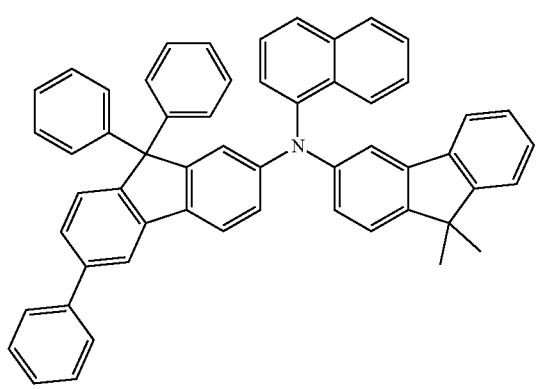
HT43
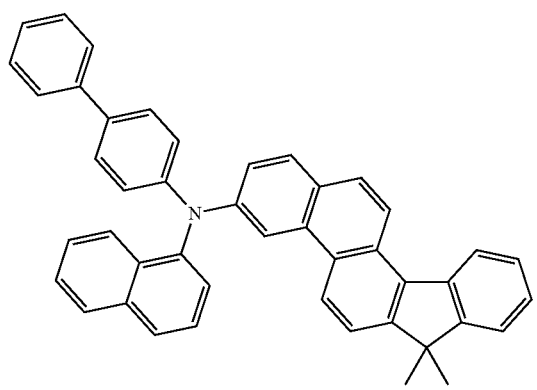

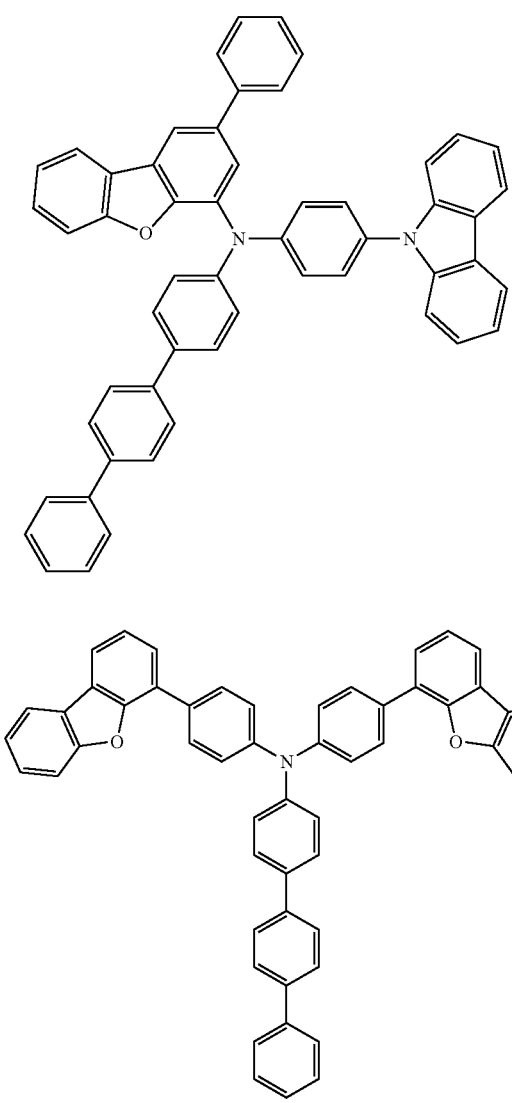

HT44

HT45

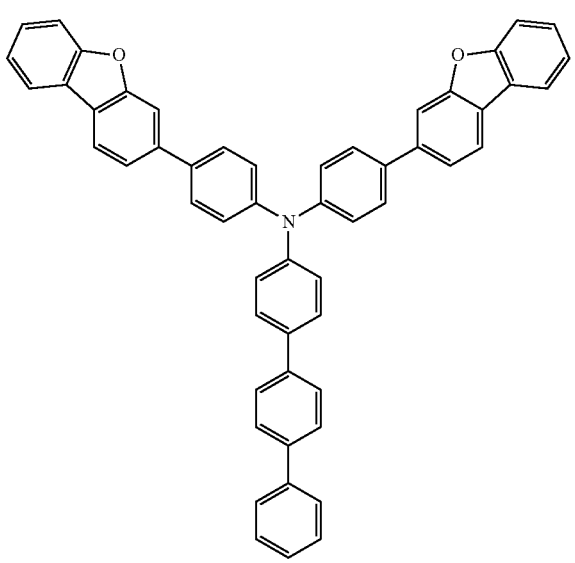

HT46

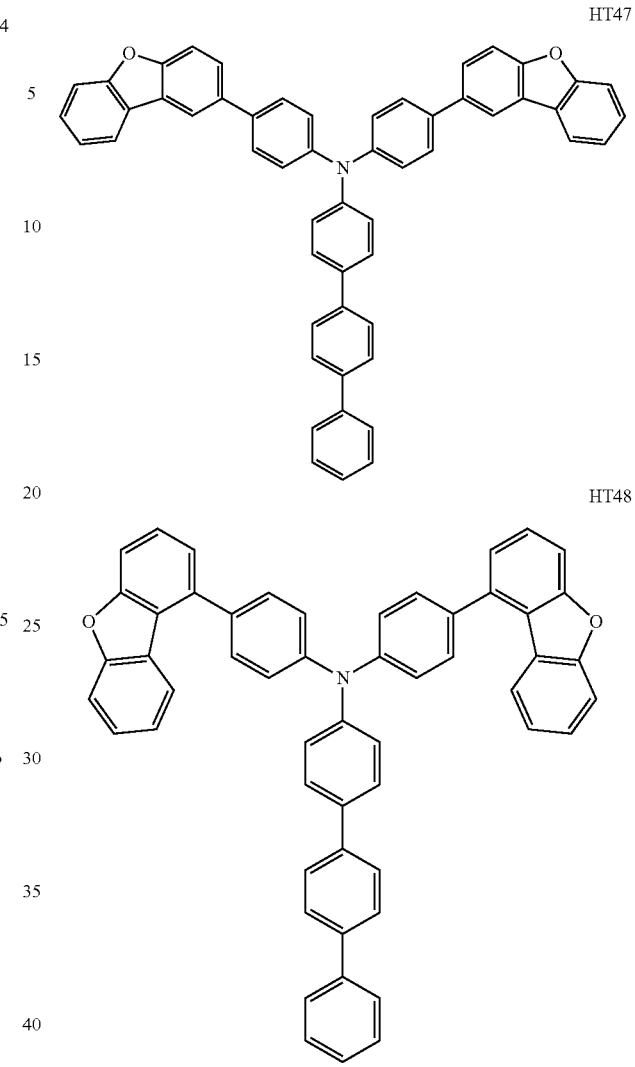

HT47

HT48

The thickness of the hole transport region may be in a range of about 100 (Angstroms) Å to about 10,000 Å, and in some exemplary embodiments, about 100 Å to about 1,000 Å. When the hole transport region includes at least one selected from a hole injection layer and a hole transport layer, the thickness of the hole injection layer may be in a range of about 100 Å to about 9,000 Å, and in some exemplary embodiments, about 100 Å to about 1,000 Å, and the thickness of the hole transport layer may be in a range of about 50 Å to about 2,000 Å, and in some exemplary embodiments, about 100 Å to about 1,500 Å. When the thicknesses of the hole transport region, the hole injection layer, and the hole transport layer are within any of these ranges, excellent hole transport characteristics may be obtained without a substantial increase in driving voltage.

The emission auxiliary layer may increase light emission efficiency by compensating for an optical resonance distance according to the wavelength of light emitted by an emission layer. The electron blocking layer may reduce or eliminate the flow of electrons from an electron transport region. The emission auxiliary layer and the electron blocking layer may include the aforementioned materials.

P-Dopant

The hole transport region may include a charge generating material as well as the aforementioned materials, to improve conductive properties of the hole transport region. The charge generating material may be substantially homogeneously or non-homogeneously dispersed in the hole transport region. The charge generating material may include, for example, a p-dopant. In some exemplary embodiments, the lowest unoccupied molecular orbital (LUMO) energy level of the p-dopant may be about −3.5 eV or less.

The p-dopant may include at least one selected from a quinone derivative, a metal oxide, and a cyano group-containing compound, but the exemplary embodiments are not limited thereto. In some exemplary embodiments, the p-dopant may include: a quinone derivative, such as tetracyanoquinodimethane (TCNQ) or 2,3,5,6-tetrafluoro-7,7,8,8-tetracyanoquinodimethane (F4-TCNQ); a metal oxide, such as tungsten oxide or molybdenum oxide; 1,4,5,8,9,12-hexaazatriphenylene-hexacarbonitrile (HAT-CN); and a compound represented by Formula 221, but the exemplary embodiments are not limited thereto:

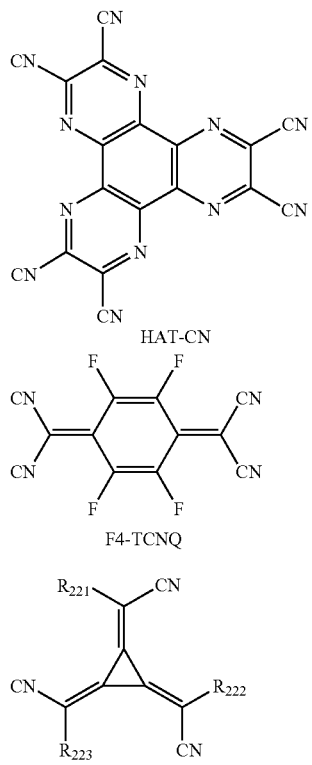

wherein, in Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_1$-$C_{10}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full color organic light-emitting device, the emission layer may be patterned into a red emission layer, a green emission layer, or a blue emission layer, according to a sub-pixel. In one or more exemplary embodiments, the emission layer may have a stacked structure. The stacked structure may include two or more layers selected from a red emission layer, a green emission layer, and a blue emission layer. The two or more layers may be in direct contact with each other. In some exemplary embodiments, the two or more layers may be separated from each other. In one or more exemplary embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light.

The emission layer may include a host and a luminescent material. The luminescent material may include at least one of a phosphorescent dopant, a fluorescent dopant, and a quantum dot. The amount of the dopant in the emission layer may be, in general, in a range of about 0.01 parts to about 15 parts by weight based on 100 parts by weight of the host, but the exemplary embodiments are not limited thereto. In some exemplary embodiments, the emission layer may emit blue light or blue-green light. In some exemplary embodiments, the heterocyclic compound emits blue light or blue-green light having a maximum emission wavelength in a range of about 400 nm to about 500 nm.

The thickness of the emission layer may be in a range of about 100 Å to about 1,000 Å, and in some exemplary embodiments, about 200 Å to about 600 Å. When the thickness of the emission layer is within any of these ranges, improved luminescence characteristics may be obtained without a substantial increase in driving voltage.

Host in Emission Layer

The host may be different from the dopant, and a content of the host may be greater than a content of the dopant, and the host may include the heterocyclic compound represented by one of Formulae 1-1 to 1-3.

The host may further include a compound represented by Formula 301:

$$[Ar_{301}]_{xb11}\text{-}[(L_{301})_{xb1}\text{-}R_{301}]_{xb21} \qquad \text{Formula 301}$$

wherein, in Formula 301, $Ar_{301}$ may be selected from a substituted or unsubstituted $C_5$-$C_{60}$ carbocyclic group and a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but the exemplary embodiments are not limited thereto.

In some exemplary embodiments, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but the exemplary embodiments are not limited thereto.

When xb11 in Formula 301 is 2 or greater, at least two $Ar_{301}$(s) may be bound via a single bond. In one or more exemplary embodiments, the compound represented by Formula 301 may be represented by Formula 301-1 or 301-2:

Formula 301-1

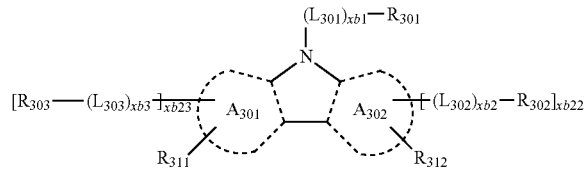

Formula 301-2

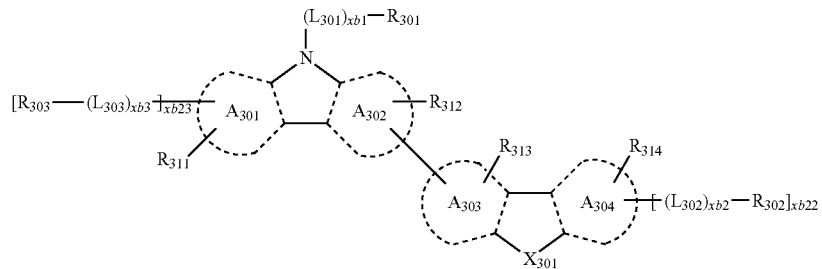

wherein, in Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonapthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may respectively be understood by referring to the descriptions of $L_{301}$, xb1, $R_{301}$, and $Q_{31}$ to $Q_{33}$ provided herein, $L_{302}$ to $L_{304}$ may each be understood by referring to the description of $L_{301}$ provided herein, xb2 to xb4 may each be understood by referring to the description of xb1 provided herein, and $R_{302}$ to $R_{304}$ may each be understood by referring to the description of $R_{301}$ provided herein.

In some exemplary embodiments, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may respectively be understood by referring to the descriptions of $Q_{31}$ to $Q_{33}$ provided herein.

In some exemplary embodiments, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may respectively be understood by referring to the descriptions of $Q_{31}$ to $Q_{33}$ provided herein.

In some exemplary embodiments, the host may include an alkaline earth metal complex. For example, the host may include a beryllium (Be) complex, e.g., Compound H55, a magnesium (Mg) complex, or a zinc (Zn) complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but the exemplary embodiments are not limited thereto:

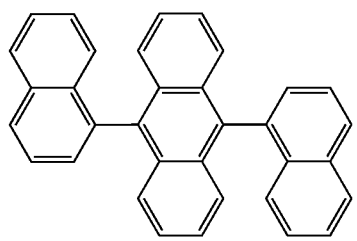

H1

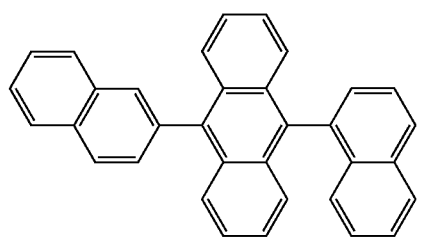

H2

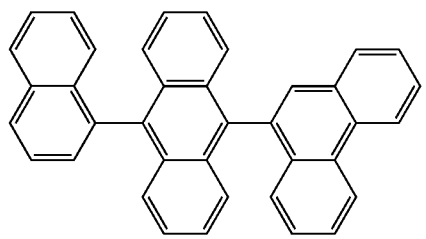

H3

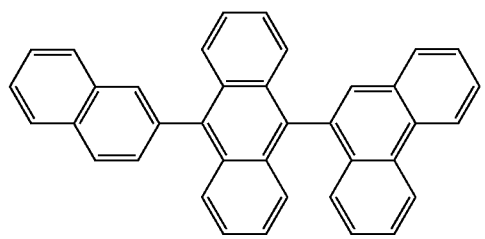

H4

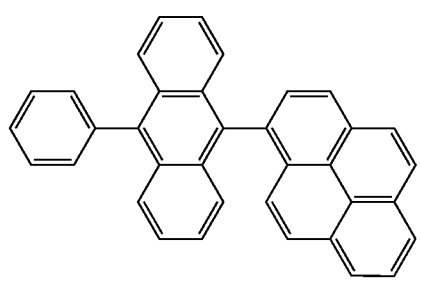

H5

H6
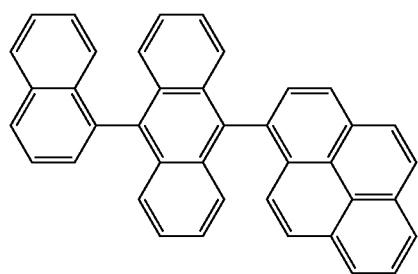
H7
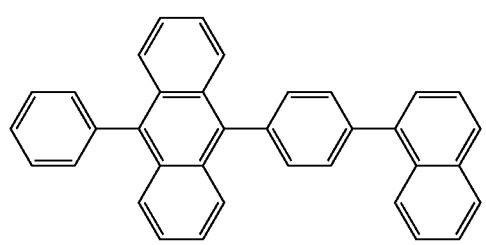
H8
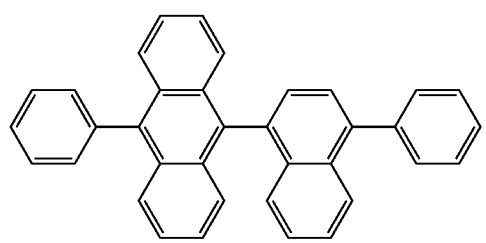
H9
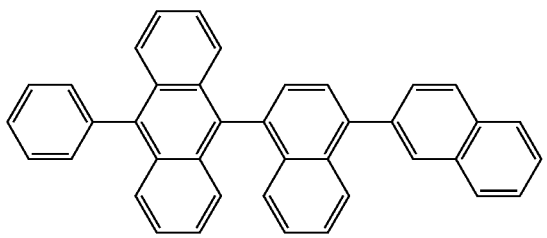
H10
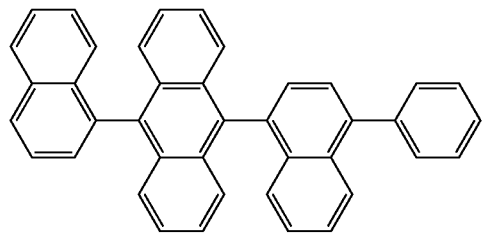
H11
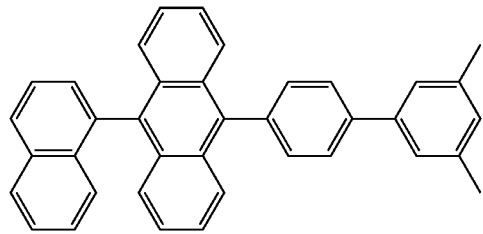
H12
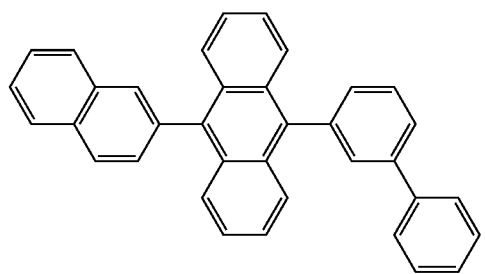
H13
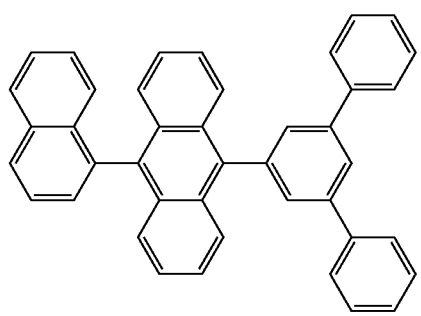
H14
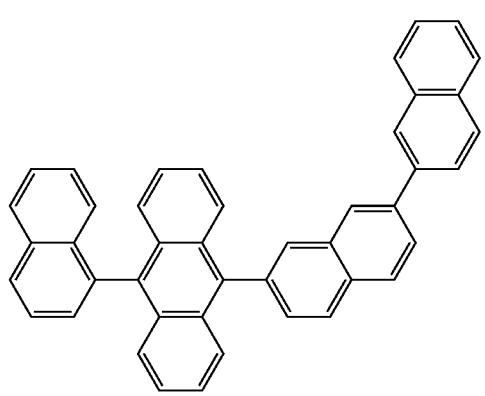
H15
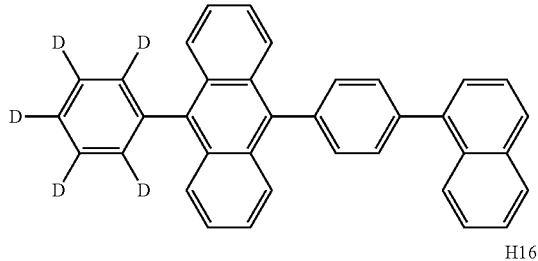
H16
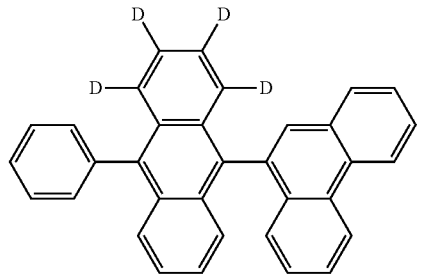

H17
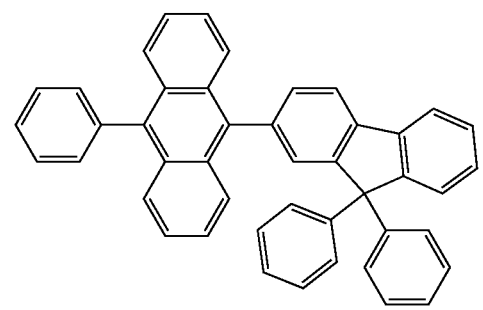
H18
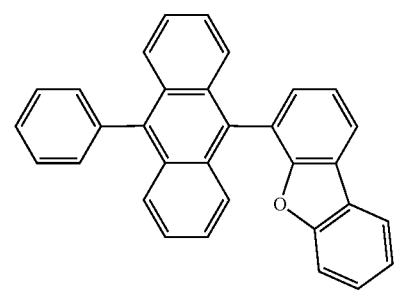
H19
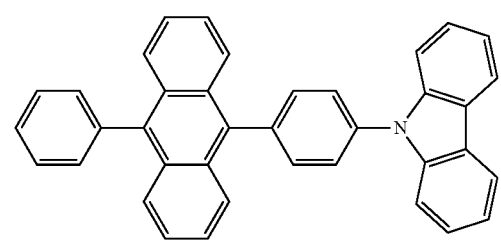
H20
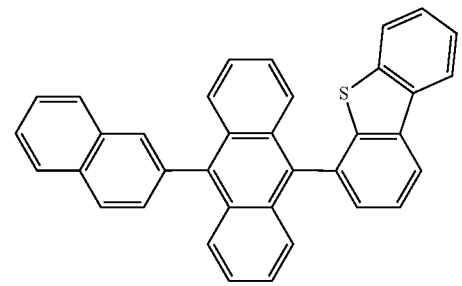
H21
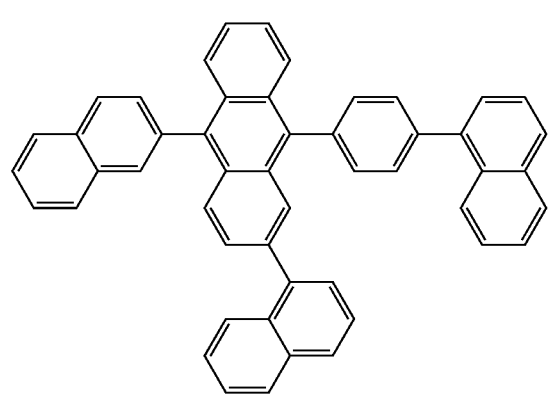
H22
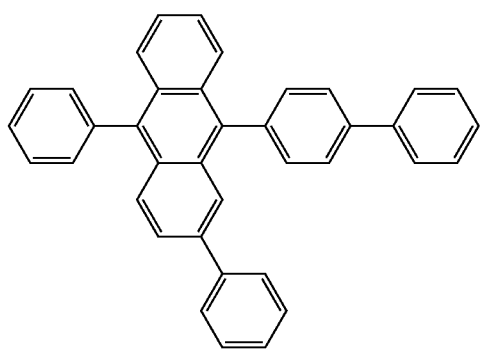
H23
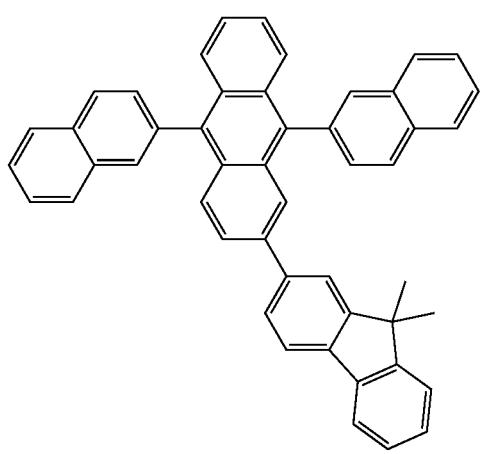
H24
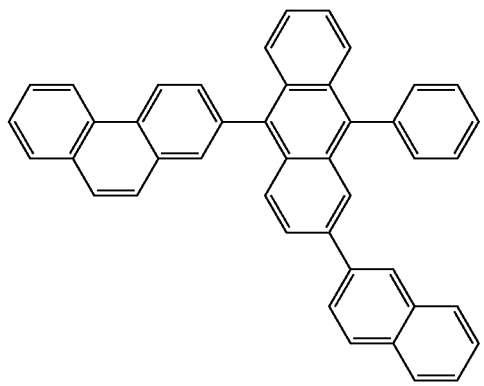

83
-continued
H25
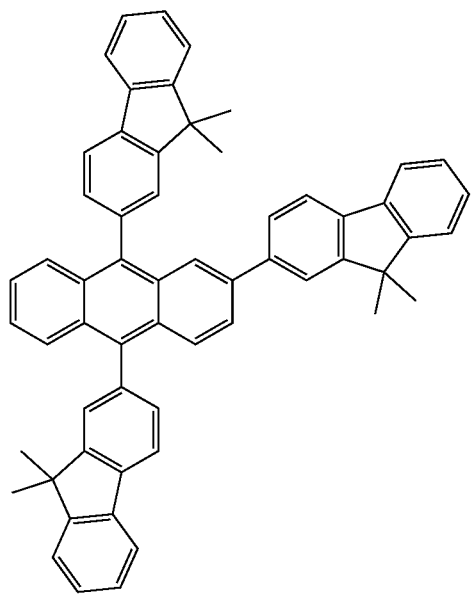
H26
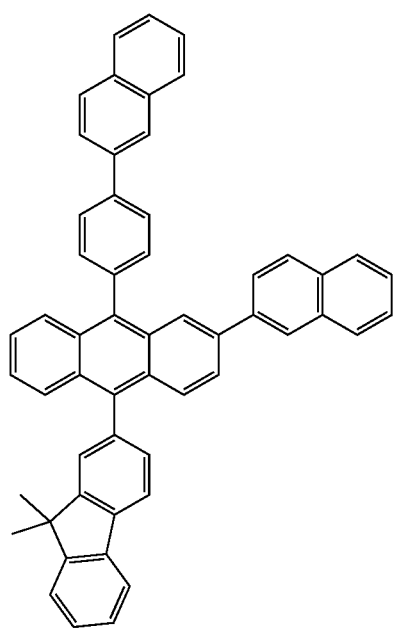
84
-continued
H27
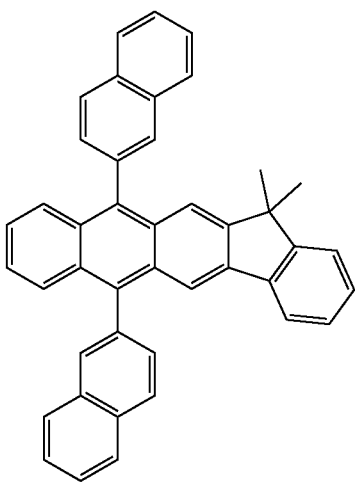
H28
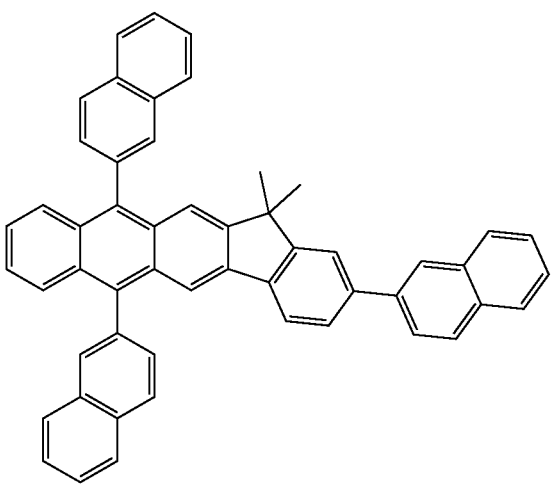
H29

H30
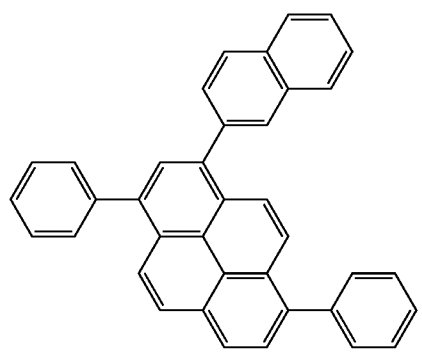
H35
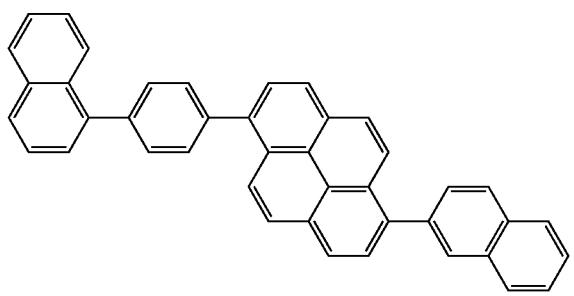
H31
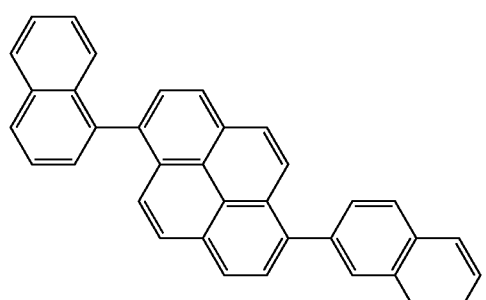
H36
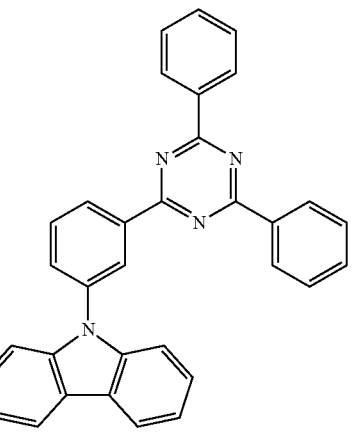
H32
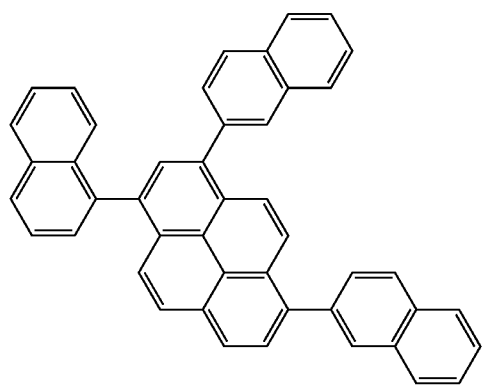
H37
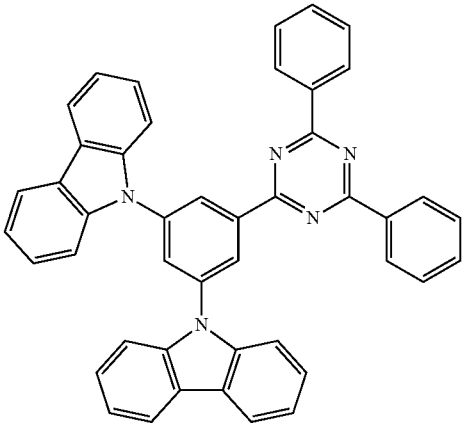
H33
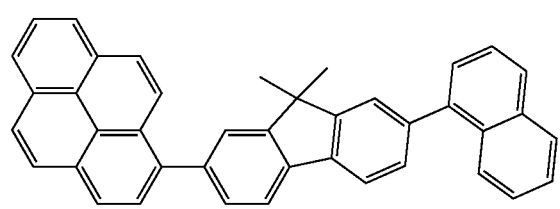
H34
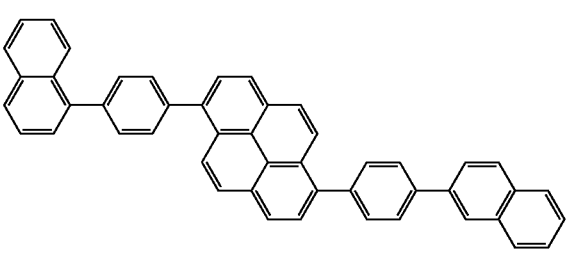
H38
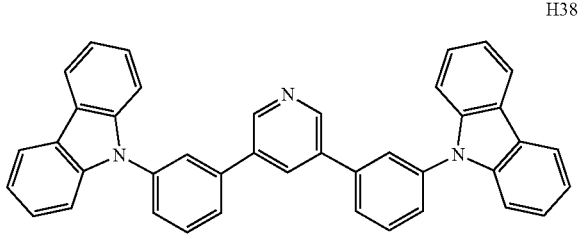

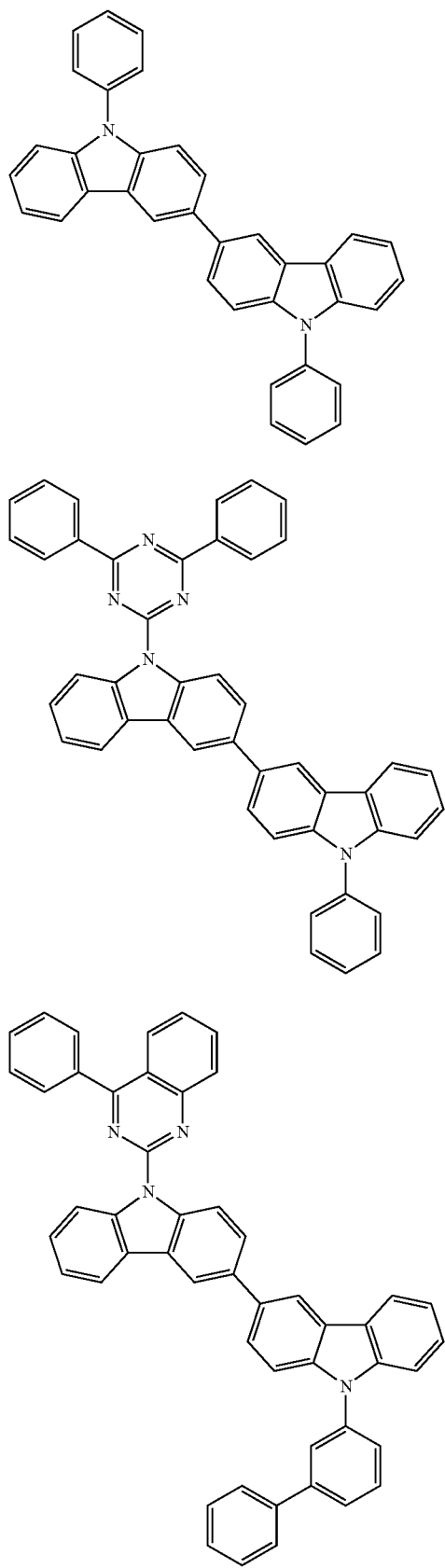
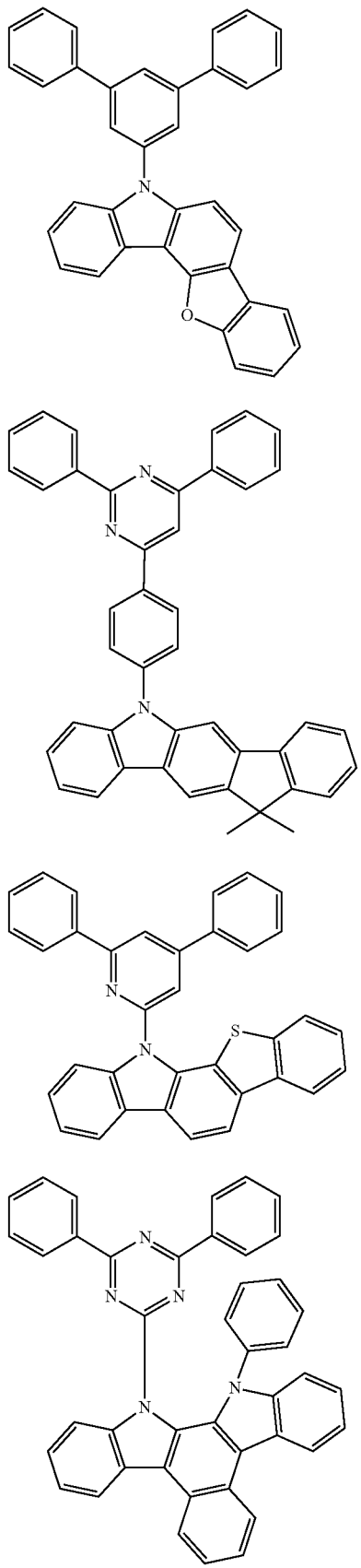

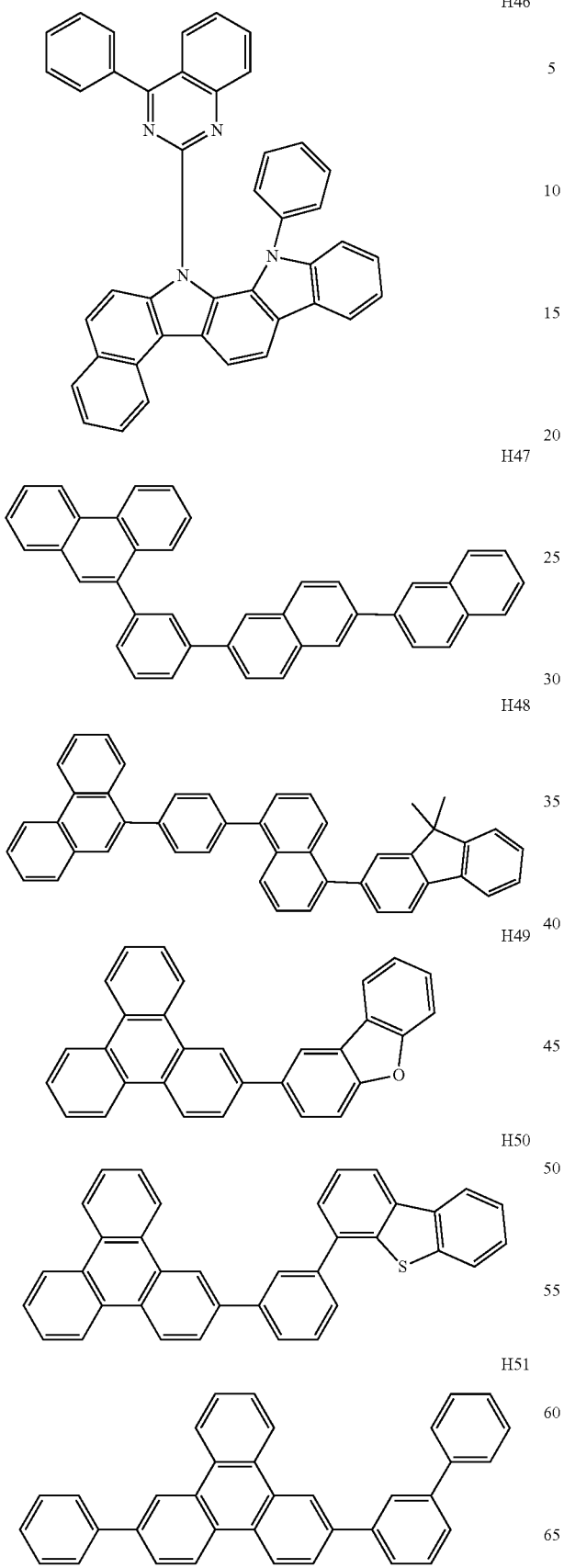
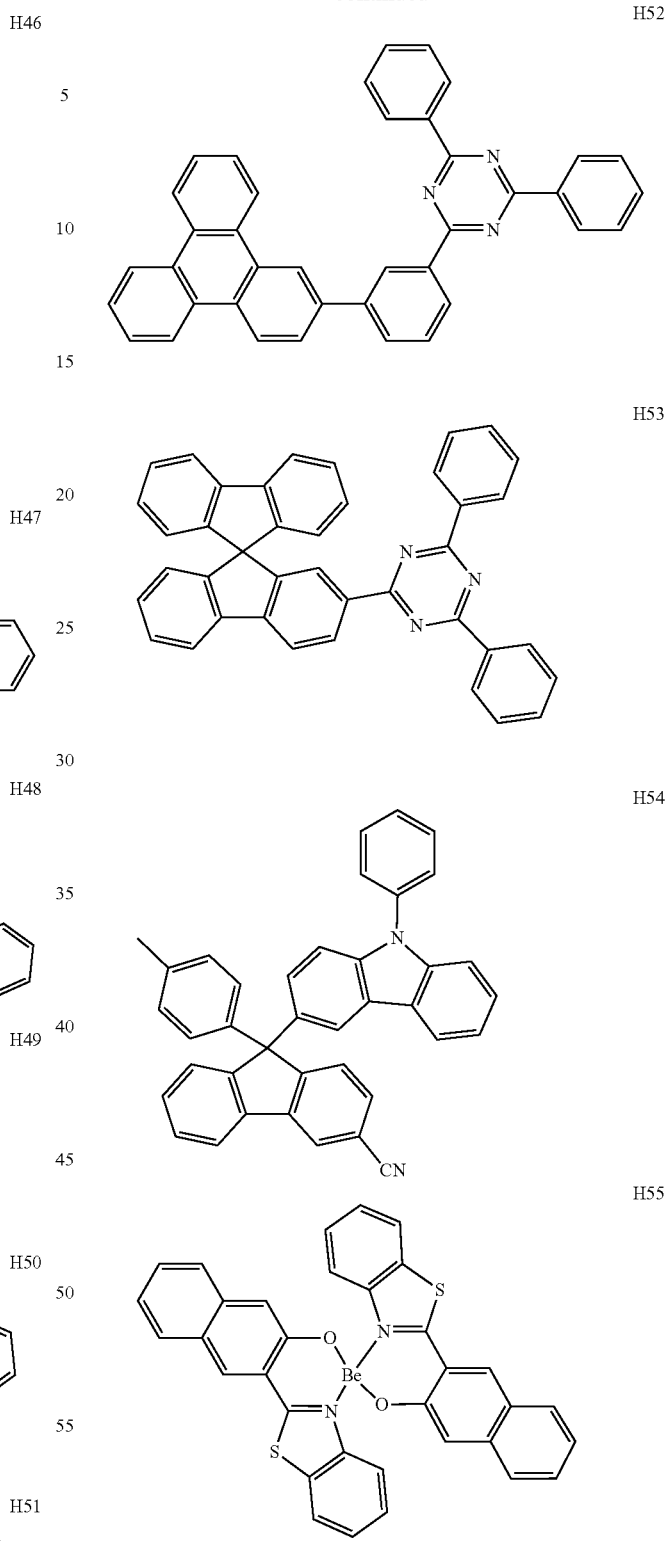
Phosphorescent Dopant Included in Emission Layer of Organic Layer 150
The phosphorescent dopant may include an organometallic complex represented by Formula 401:
$$M(L_{401})_{xc1}(L_{402})_{xc2} \qquad \text{Formula 401}$$

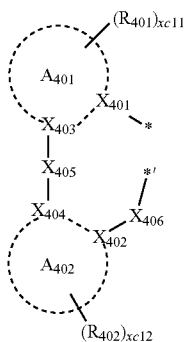

Formula 402 wherein, in Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, and when xc1 is 2 or greater, at least two $L_{401}(s)$ may be identical to or different from each other, $L_{402}$ may be an organic ligand, and xc2 may be an integer selected from 0 to 4, and when xc2 is 2 or greater, at least two $L_{402}(s)$ may be identical to or different from each other, $X_{401}$ to $X_{404}$ may each independently be a nitrogen or a carbon, $X_{401}$ and $X_{403}$ may be bound to each other via a single bond or a double bond, $X_{402}$ and $X_{404}$ may be bound to each other via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)—*', *—C($Q_{411}$)($Q_{412}$)—*', *—C($Q_{411}$)=C($Q_{412}$)-*', *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In some exemplary embodiments, in Formula 402, $A_{401}$ and $A_{402}$ may each independently be selected from a benzene group, a naphthalene group, a fluorene group, a spirobifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more exemplary embodiments, in Formula 402, i) $X_{401}$ may be nitrogen, and $X_{402}$ may be carbon, or ii) $X_{401}$ and $X_{402}$ may each be nitrogen. In some exemplary embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantyl group, a norbornanyl group, and a norbornenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but the exemplary embodiments are not limited thereto.

In one or more exemplary embodiments, when xc1 in Formula 401 is 2 or greater, two $A_{401}$(s) of at least two $L_{401}$(s) may optionally be linked via $X_{407}$ as a linking group; or two $A_{402}$(s) may optionally be linked via $X_{408}$ as a linking group (see Compounds PD1 to PD4 and PD7). $X_{407}$ and $X_{408}$ may each independently be selected from a single bond, *—O—*', *—S—*', *—C(=O)—*', *—N($Q_{413}$)-*', *—C($Q_{413}$)($Q_{414}$)-*', and *—C($Q_{413}$)=C($Q_{414}$)-*', wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, but the exemplary embodiments are not limited thereto.

$L_{402}$ in Formula 401 may be any suitable monovalent, divalent, or trivalent organic ligand. For example, $L_{402}$ may be selected from halogen, diketone (e.g., acetylacetonate), a carboxylic acid (e.g., picolinate), —C(=O), isonitrile, —CN, and phosphorus (e.g., phosphine or phosphite), but the exemplary embodiments are not limited thereto.

In some exemplary embodiments, the phosphorescent dopant may include, for example, at least one selected from Compounds PD1 to PD25, but the exemplary embodiments are not limited thereto:

PD1

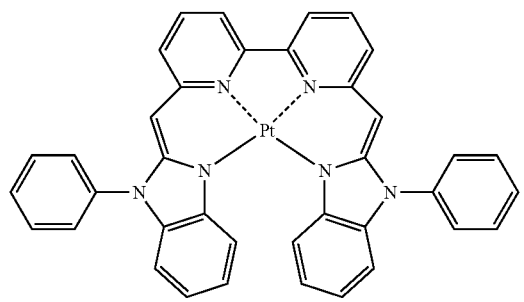

PD2

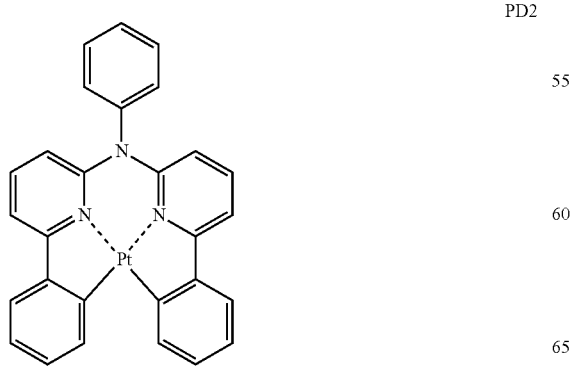

PD3

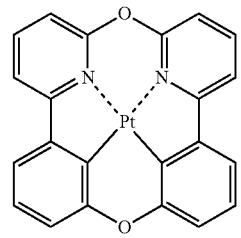

PD4

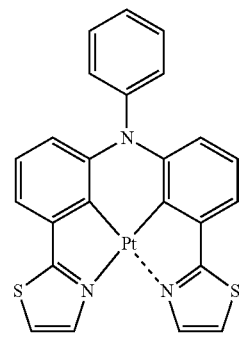

PD5

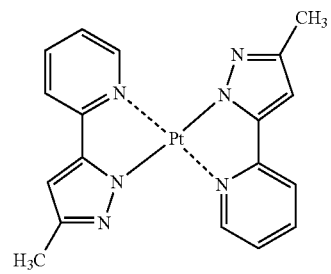

PD6

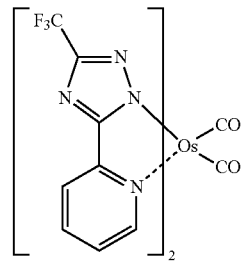

PD7

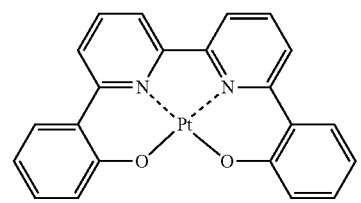

PD8

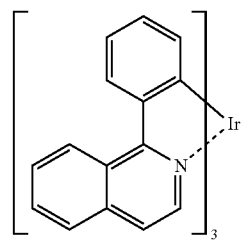

-continued
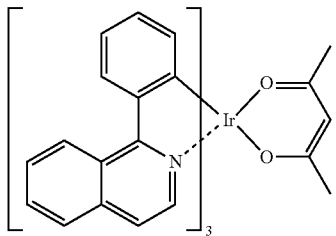
PD9
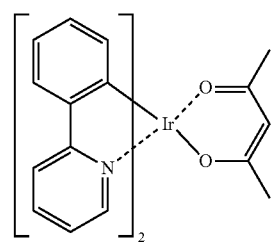
PD14
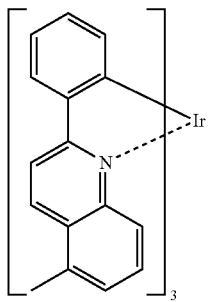
PD10
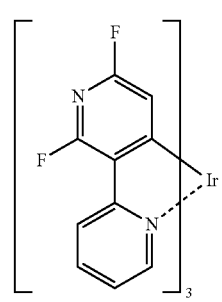
PD15
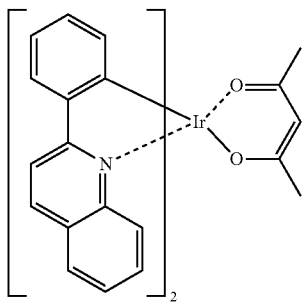
PD11
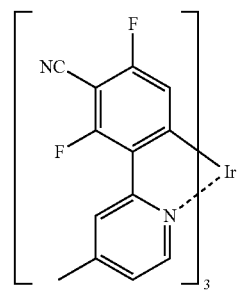
PD16
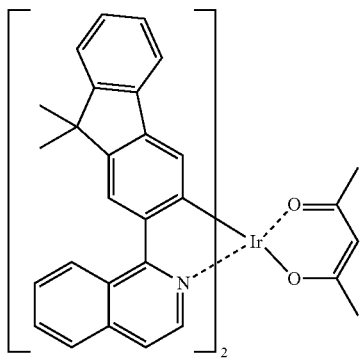
PD12
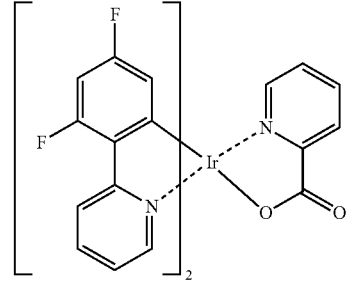
PD17
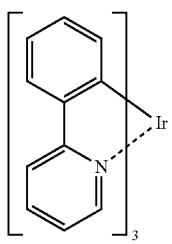
PD13
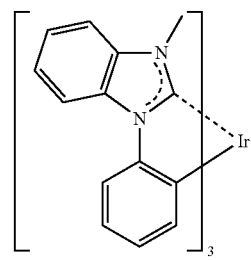
PD18

-continued

PD19 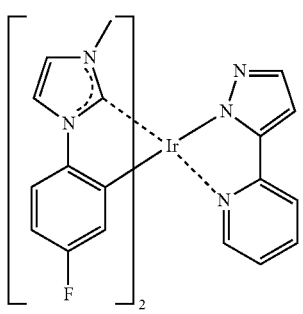

PD20 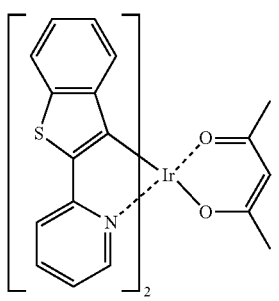

PD21 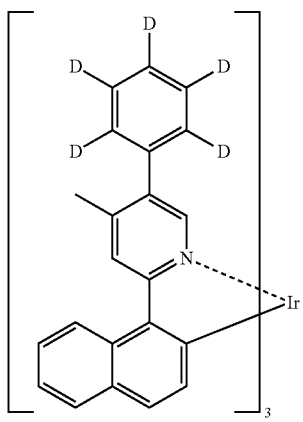

PD22 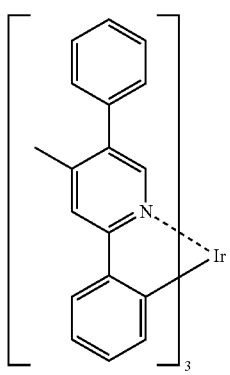

-continued

PD23 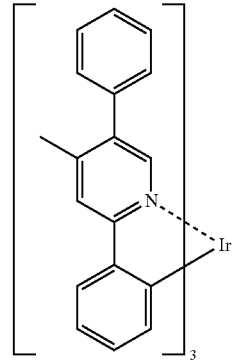

PD24 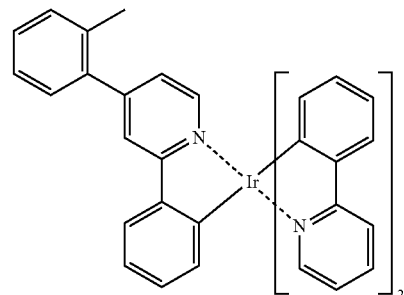

PD25 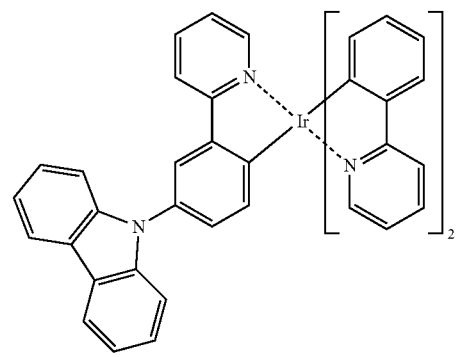

Fluorescent Dopant in Emission Layer

In some exemplary embodiments, the fluorescent dopant may include the heterocyclic compound represented by one of Formulae 1-1 to 1-3. The fluorescent dopant may further include an arylamine compound or a styrylamine compound.

In some exemplary embodiments, the fluorescent dopant may further include a compound represented by Formula 501:

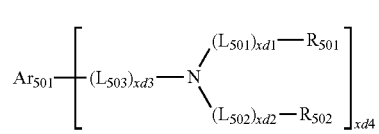

Formula 501 wherein, in Formula 501,

Ar$_{501}$ may be selected from a substituted or unsubstituted C$_5$-C$_{60}$ carbocyclic group and a substituted or unsubstituted C$_1$-C$_{60}$ heterocyclic group, L$_{501}$ to L$_{503}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In some exemplary embodiments, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some exemplary embodiments, in Formula 501, $L_{501}$ and $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In some exemplary embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may be selected from a $C_1$-$C_{10}$ alkyl group, a $C_1$-$C_{10}$ alkoxy group, a phenyl group, a biphenyl group, a terphenyl group, and a naphthyl group.

In one or more exemplary embodiments, xd4 in Formula 501 may be 2, but the exemplary embodiments are not limited thereto. In some exemplary embodiments, the fluorescent dopant may be selected from Compounds FD1 to FD22:

FD1

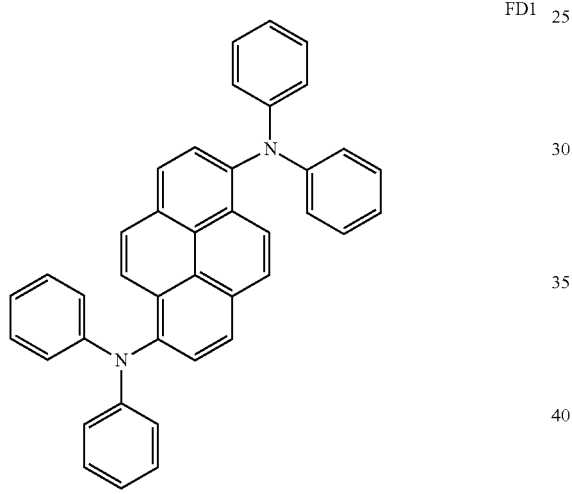

FD2

FD3

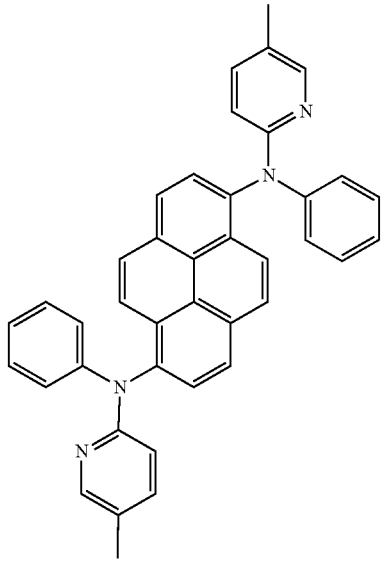

FD4

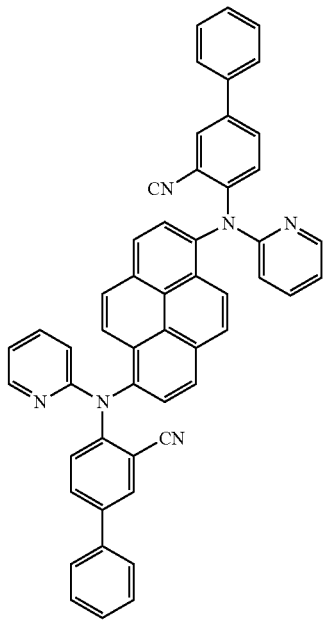

FD5
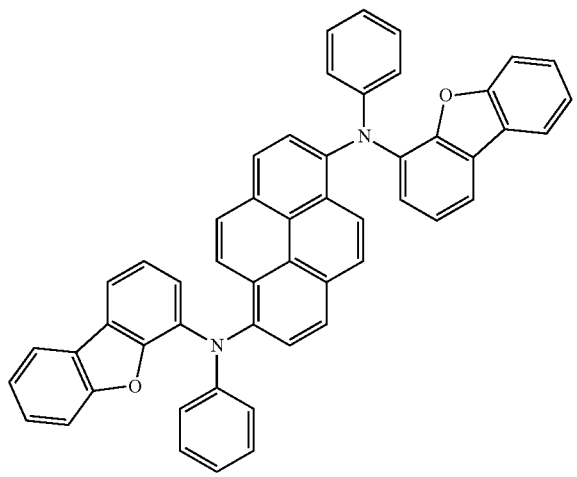
FD6
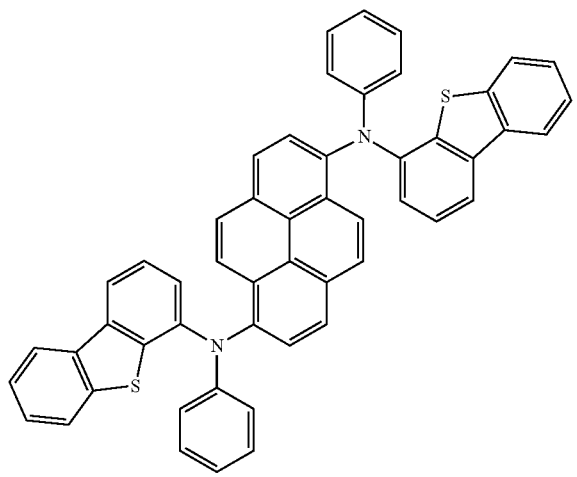
FD7
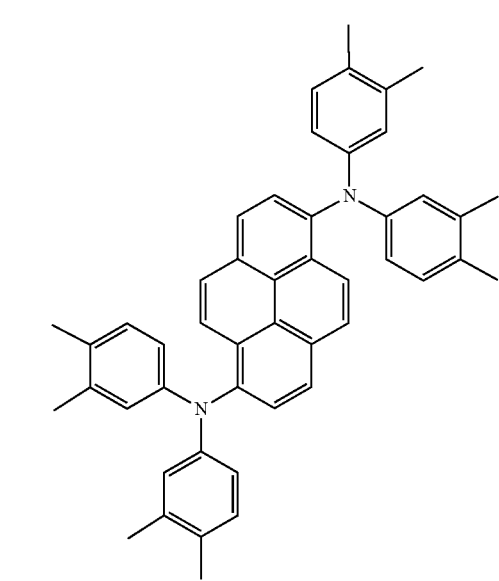
FD8
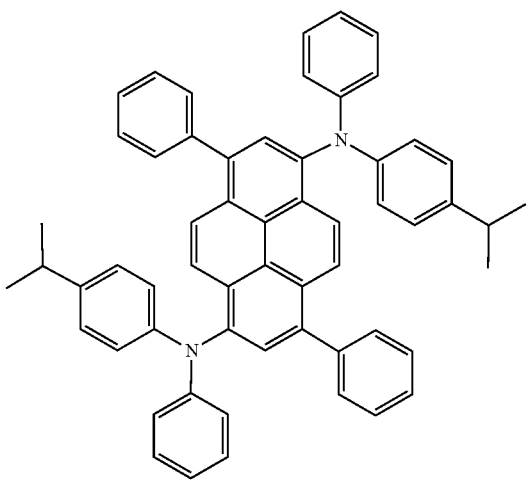
FD9
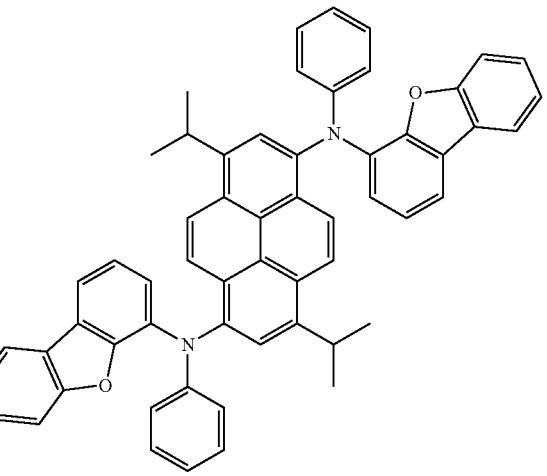
FD10
FD11
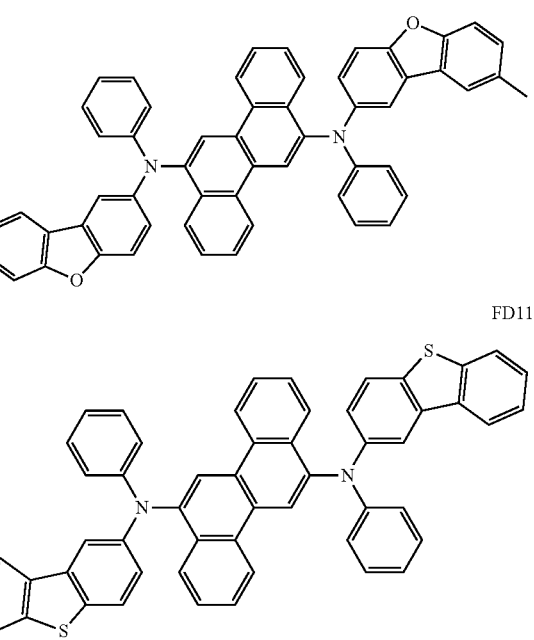

FD12
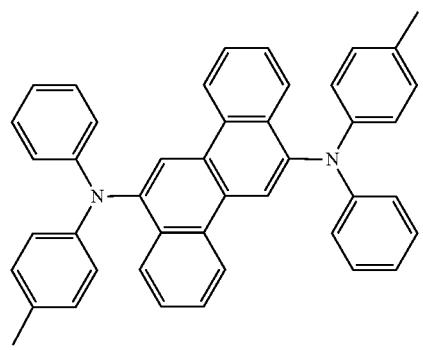
FD13
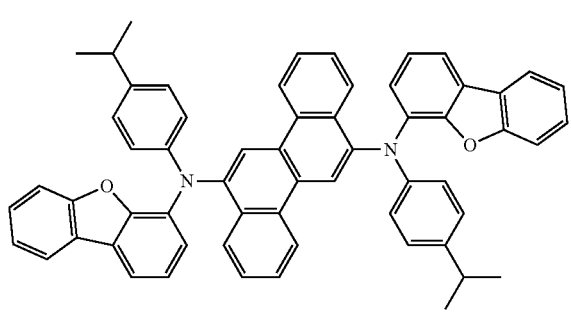
FD14
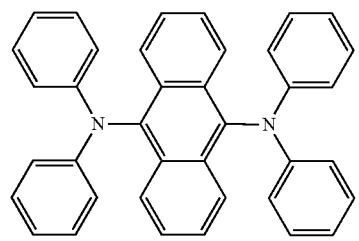
FD15
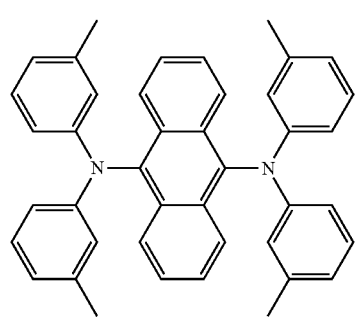
FD16
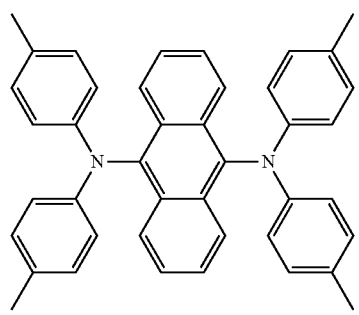
FD17
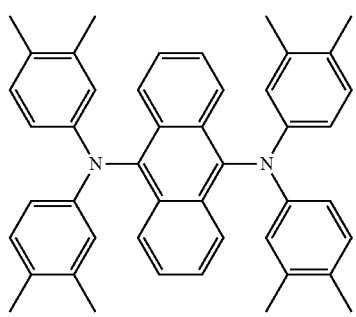
FD18
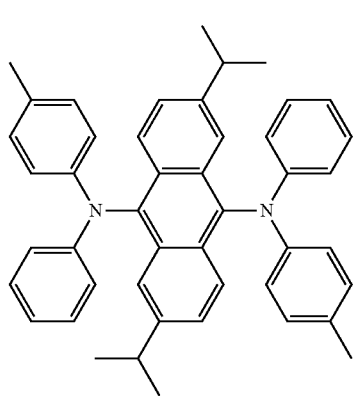
FD19
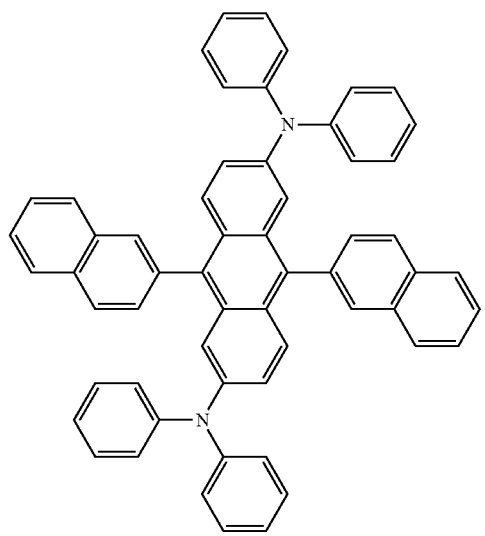
FD20
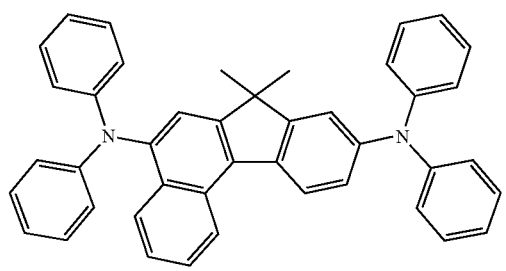

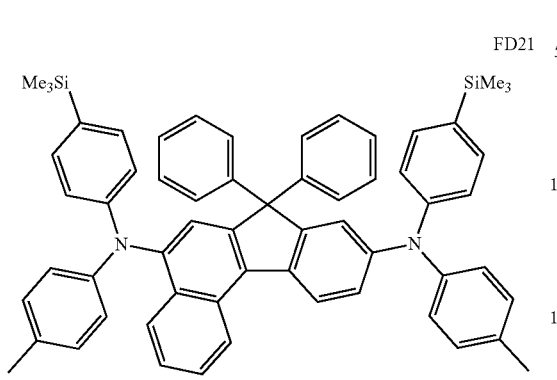
FD21
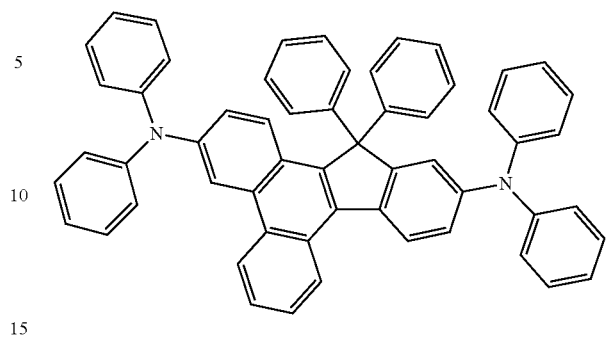
FD22
In some exemplary embodiments, the fluorescent dopant may be selected from the following compounds, but the exemplary embodiments are not limited thereto:
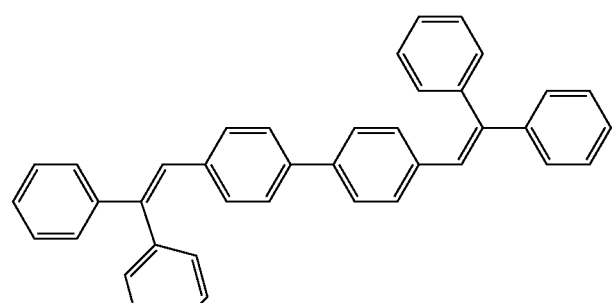
DPVBi
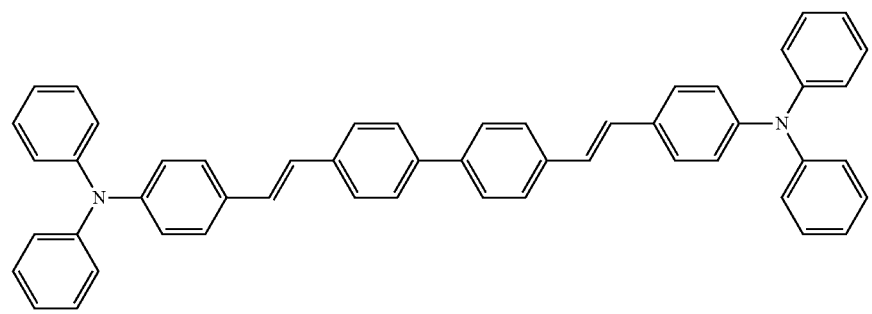
DPAVBi
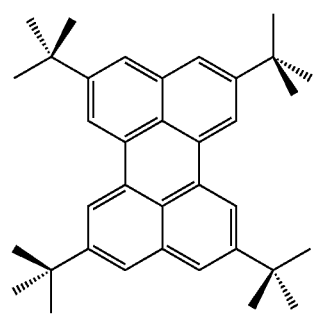
TBPe
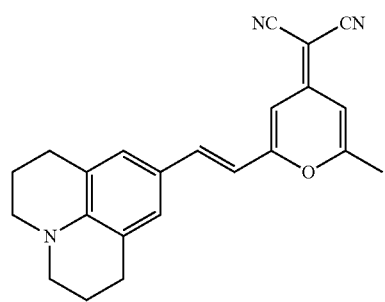
DCM

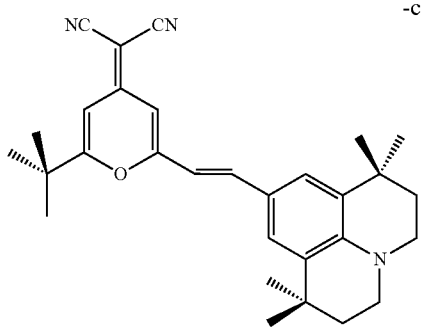

DCJTB

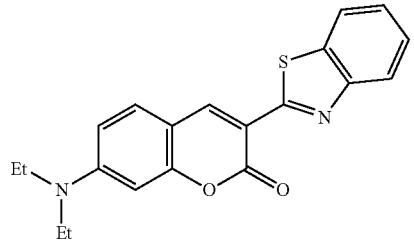

Coumarin 6

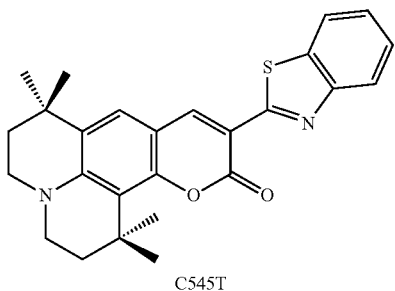

C545T

Quantum Dot

The emission layer included in the organic light-emitting device of some exemplary embodiments may include a quantum dot material. The quantum dot is a particle having a crystal structure of generally several to tens of nanometers in size. Generally, the quantum dot may include hundreds to thousands of atoms.

Since the quantum dot is very small in size, quantum confinement effect may occur. The quantum confinement is a phenomenon in which a band gap of an object becomes larger when the object becomes smaller than a nanometer size. Accordingly, when light of a wavelength having an energy larger than a band gap of the quantum dot is incident on the quantum dot, the quantum dot is excited by absorbing the light, emits light of a specific wavelength, and falls to the ground state. In this case, the wavelength of the emitted light may have a value corresponding to the band gap.

A core of the quantum dot may include a II-VI compound, a III-VI compound, a III-V compound, a IV-VI compound, a Group IV element or compound, a I-III-VI compound, or a combination thereof.

The II-VI compound may be selected from a binary compound selected from the group consisting of CdS, CdSe, CdTe, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of CdZnSeS, CdZnSeTe, CdZnSTe, CdHgSeS, CdHgSeTe, CdHgSTe, HgZnSeS, HgZnSeTe, HgZnSTe, and a mixture thereof.

The III-VI compound may include a binary compound such as $In_2S_3$ or $In_2Se_3$; a ternary compound such as $InGaS_3$ or $InGaSe_3$; or any combination thereof. The III-V compound may be selected from a binary compound selected from the group consisting of GaN, GaP, GaAs, GaSb, AlN, AlP, AlAs, AlSb, InN, InP, InAs, InSb and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, GaAlNP, and a mixture thereof. The III-V semiconductor compound may further include a Group II metal (e.g., InZnP).

The IV-VI compound may be selected from a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The IV compound may be a binary compound selected from the group consisting of SiC, SiGe, and a mixture thereof.

In some exemplary embodiments, the binary compound, the ternary compound, or the quaternary compound may be present in particles at a uniform concentration or in the same particle by being partially divided into different concentrations. In addition, one quantum dot may have a core-shell structure surrounding another quantum dot. An interface between a core and a shell may have a concentration gradient where a concentration of elements present in the shell decreases toward the center.

In some exemplary embodiments, the quantum dot may have a core-shell structure including a core including the nanocrystals described above and a shell surrounding the core. The shell of the quantum dot may serve as a protective layer for preventing chemical denaturation of the core to maintain semiconductor characteristics and/or as a charging layer for imparting electrophoretic characteristics to the quantum dot. The shell may be monolayer or multilayer. An interface between a core and a shell may have a concentration gradient where a concentration of elements present in the shell decreases toward the center. Examples of the shell of the quantum dot include metal or nonmetal oxide, a semiconductor compound, or a combination thereof.

In some exemplary embodiments, the metal or nonmetal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, or NiO or a ternary compound such as $MgAl_2O_4$, $CoFe_2O_4$, $NiFe_2O_4$, or $CoMn_2O_4$, but the exemplary embodiments are not limited thereto. In addition, the semiconductor compound may be CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, or AlSb, but the exemplary embodiments are not limited thereto.

The quantum dot may have a full width of half maximum (FWHM) of a spectrum of an emission wavelength of about 45 nm or less, about 40 nm or less, or about 30 nm or less. When the FWHM of the quantum dot is within this range, color purity or color reproducibility may be improved. In addition, because light emitted through the quantum dot is emitted in all directions, an optical viewing angle may be improved.

In addition, the form of the quantum dot may be a form generally used in the art and is not particularly limited. The quantum dot may be a generally spherical form, a generally pyramidal form, a generally multi-armed, or a generally cubic nanoparticle, or a generally nanotube-shaped, a generally nanowire-shaped, a generally nanofiber-shaped, a generally nano-plate-shaped particle, or the like. The quantum dot may control color of emitted light according to particle size. Accordingly, the quantum dot may have various emission colors such as blue, red, or green.

Electron Transport Region in Organic Layer 150

The electron transport region may have i) a single-layered structure consisting of a single layer consisting of a single material, ii) a single-layered structure consisting of a single layer including a plurality of different materials, or iii) a multi-layered structure each having a plurality of layers, each having a plurality of different materials. The electron transport region may include at least one selected from a buffer layer, a hole blocking layer, an electron control layer, an electron transport layer, and an electron injection layer, but the exemplary embodiments are not limited thereto.

In some exemplary embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure are sequentially stacked on the emission layer in each stated order, but the exemplary embodiments are not limited thereto.

The electron transport region (e.g., the buffer layer, the hole blocking layer, the electron control layer, the electron transport layer, and/or the electron injection layer in the electron transport region) may include a heterocyclic compound represented by Formula 1. In some exemplary embodiments, the electron transport region may include the heterocyclic compound represented by Formula 1 and may further include a metal-free compound containing at least one π electron-depleted nitrogen-containing ring.

For example, the "π electron-depleted nitrogen-containing ring" may be i) a 5-membered to 7-membered heteromonocyclic group having at least one *—N=*' moiety, ii) a heteropolycyclic group in which at least two 5-membered to 7-membered heteromonocyclic groups, each having at least one *—N=*' moiety, are condensed, or iii) a heteropolycyclic group in which at least one of a 5-membered to 7-membered heteromonocyclic group, each having at least one *—N=*' moiety, is condensed with at least one $C_5$-$C_{60}$ carbocyclic group.

Examples of the π electron-depleted nitrogen-containing ring may include imidazole, pyrazole, thiazole, isothiazole, oxazole, isoxazole, pyridine, pyrazine, pyrimidine, pyridazine, indazole, purine, quinoline, isoquinoline, benzoquinoline, phthalazine, naphthyridine, quinoxaline, quinazoline, cinnoline, phenanthridine, acridine, phenanthroline, phenazine, benzimidazole, isobenzothiazole, benzoxazole, isobenzoxazole, triazole, tetrazole, oxadiazole, triazine, thiadiazole, imidazopyridine, imidazopyrimidine, and azacarbazole, but the exemplary embodiments are not limited thereto.

In some exemplary embodiments, the electron transport region may include a compound represented by Formula 601:

$$[Ar_{601}]_{xe11}-[(L_{601})_{xe1}-R_{600}]_{xe21} \quad \text{Formula 601}$$

wherein, in Formula 601, $Ar_{601}$ may be selected from a substituted or unsubstituted $C_5$-$C_{60}$ carbocyclic group and a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some exemplary embodiments, at least one selected from $Ar_{601}$(s) in the number of xe11 and $R_{601}$(s) in the number of xe21 may include the π electron-depleted nitrogen-containing ring. In some exemplary embodiments, in Formula 601, $Ar_{601}$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(═O)$_2$($Q_{31}$), and —P(═O)($Q_{31}$)($Q_{32}$),
wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or greater, at least two Ar$_{601}$(s) may be bound via a single bond. In one or more exemplary embodiments, Ar$_{601}$ in Formula 601 may be an anthracene group.

In some exemplary embodiments, the compound represented by Formula 601 may be represented by Formula 601-1:

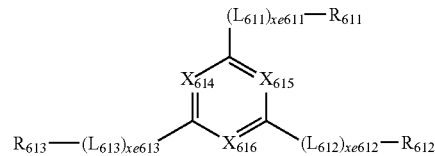

Formula 601-1 wherein, in Formula 601-1,
$X_{614}$ may be N or C($R_{614}$), $X_{615}$ may be N or C($R_{615}$), $X_{616}$ may be N or C($R_{616}$), at least one selected from $X_{614}$ to $X_{616}$ may be N,
$L_{611}$ to $L_{613}$ may each independently be understood by referring to the description of $L_{601}$ provided herein,
xe611 to xe613 may each independently be understood by referring to the description of xe1 provided herein,
$R_{611}$ to $R_{613}$ may each independently be understood by referring to the description of $R_{601}$ provided herein, and
$R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some exemplary embodiments, in Formulae 601 and 601-1, $L_{601}$ and $L_{611}$ to $L_{613}$ may each independently be selected from:
a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but the exemplary embodiments are not limited thereto.

In one or more exemplary embodiments, in Formulae 601 and 601-1, xe1 and xe611 to xe613 may each independently be 0, 1, or 2. In one or more exemplary embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S($=$O)$_2$(Q$_{601}$) and —P($=$O)(Q$_{601}$)(Q$_{602}$), wherein Q$_{601}$ and Q$_{602}$ may respectively be understood by referring to the descriptions of Q$_{601}$ and Q$_{602}$ provided herein.

The electron transport region may include at least one compound selected from Compounds ET1 to ET36, but the exemplary embodiments are not limited thereto:

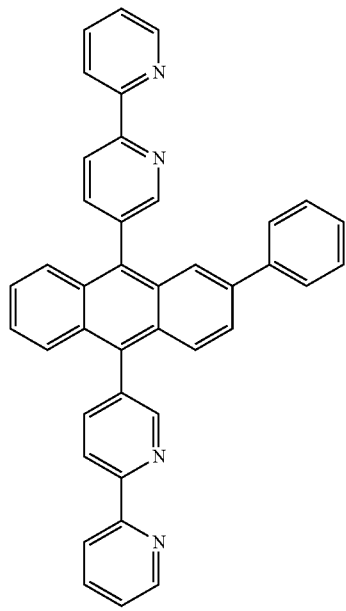

ET1

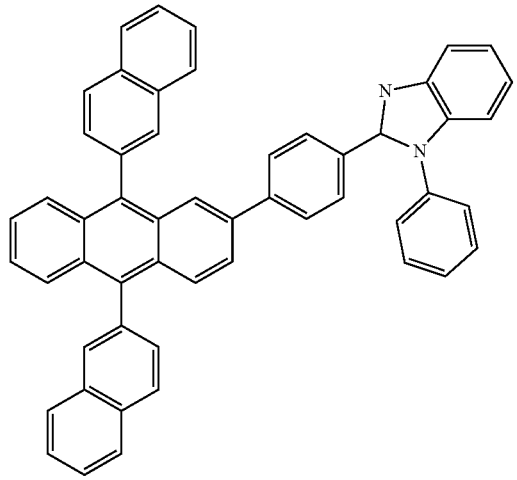

ET2

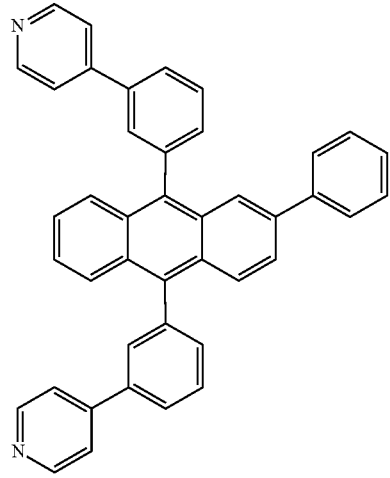

ET3

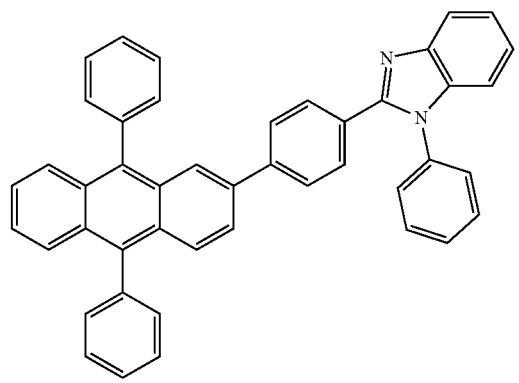

ET4

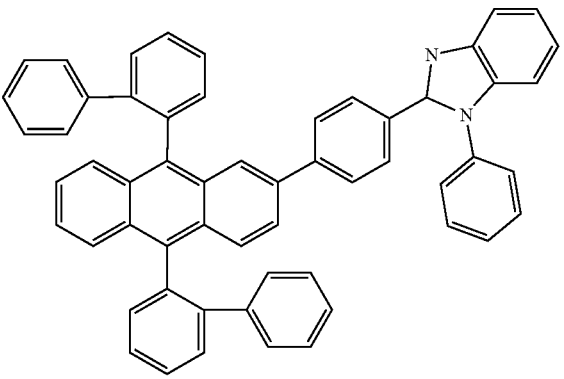

ET5

ET6
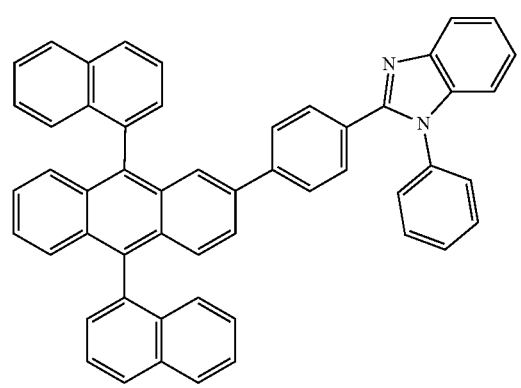
ET7
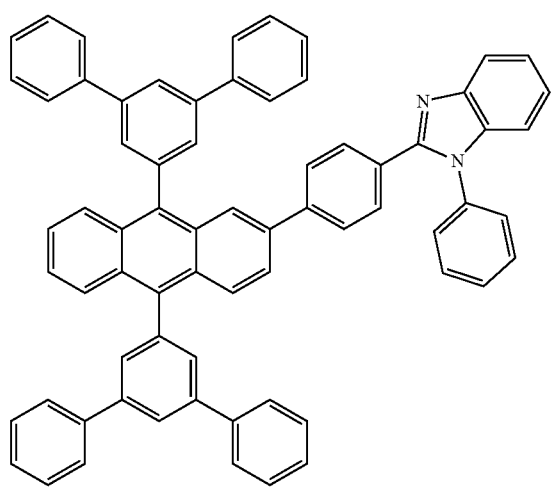
ET8
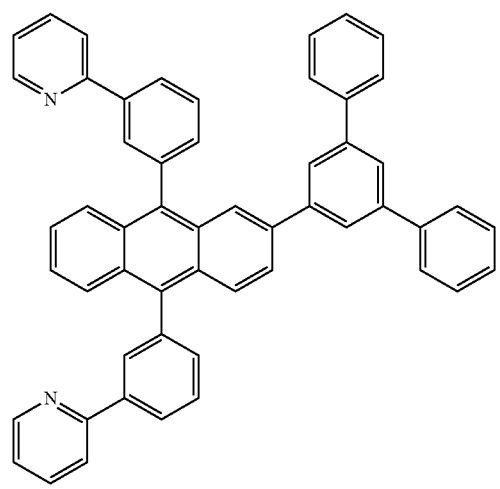
ET9
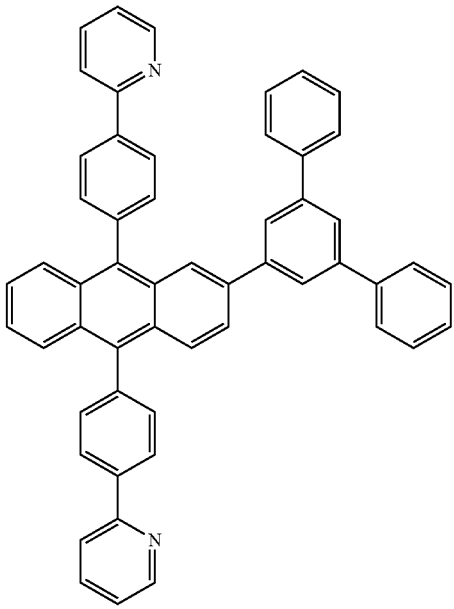
ET10
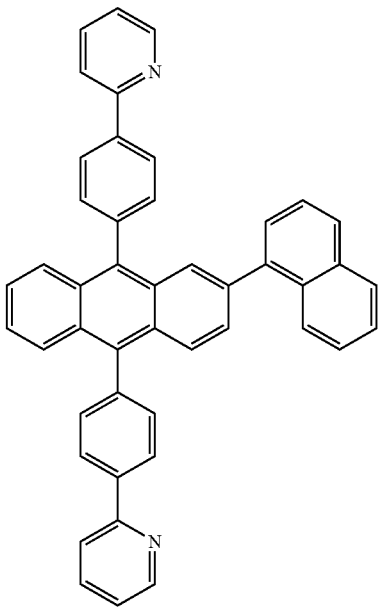

-continued
ET11
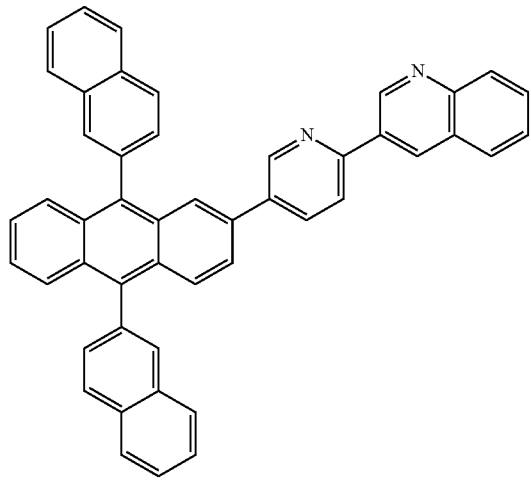
ET12
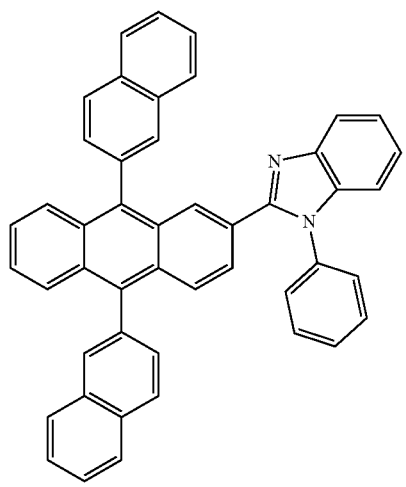
ET13
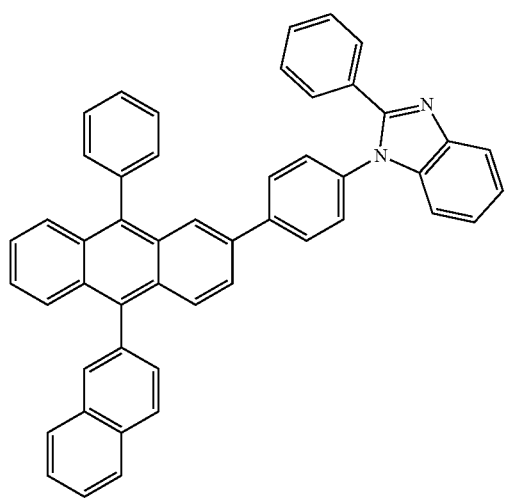
-continued
ET14
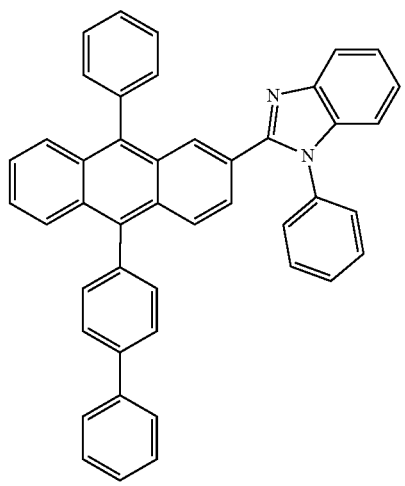
ET15
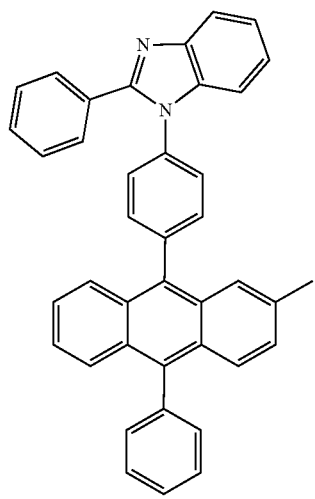
ET16
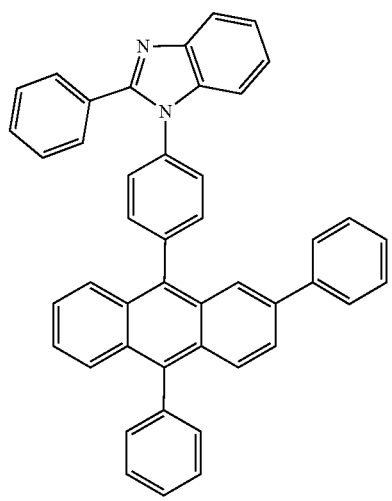

ET17
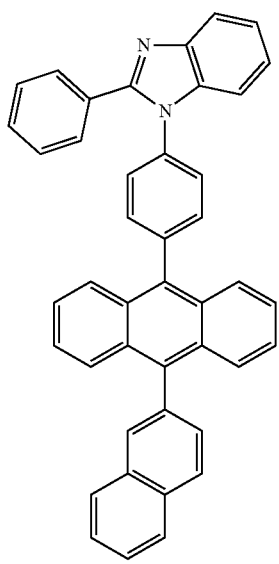
ET18
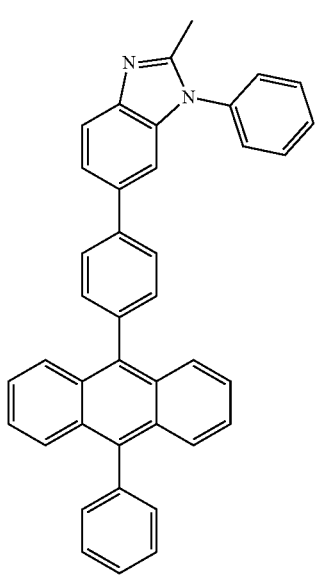
ET19
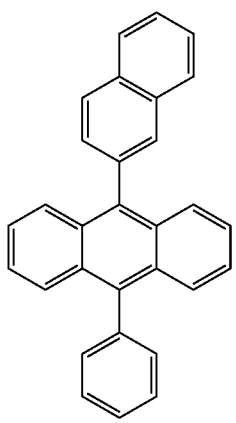
ET20
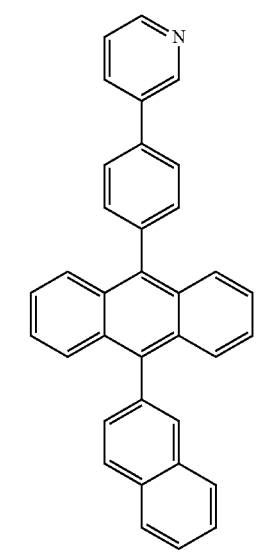
ET21
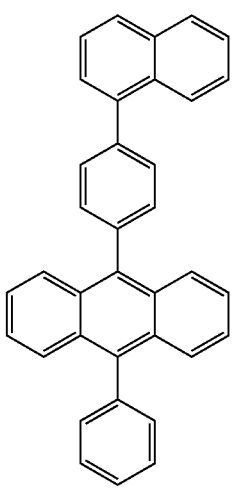
ET22
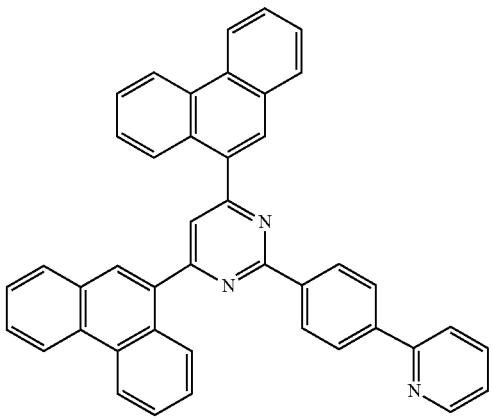

ET23
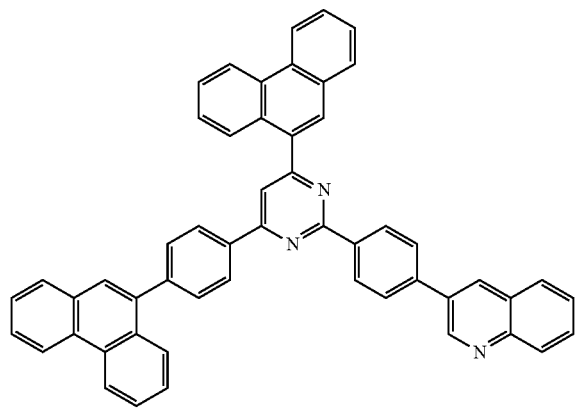
ET24
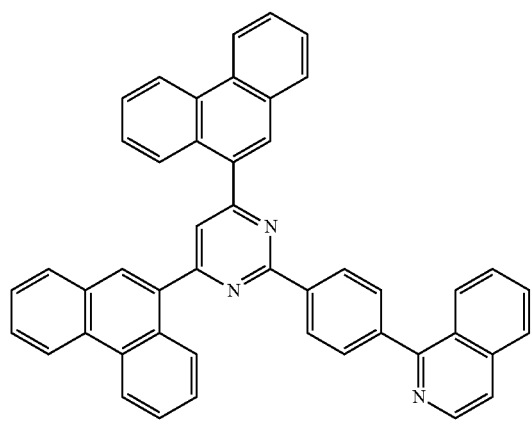
ET25
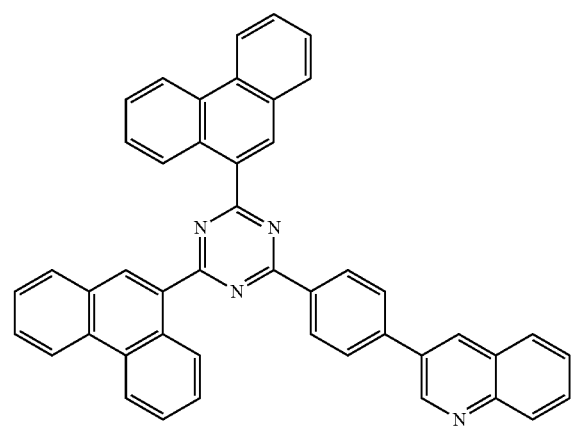
ET26
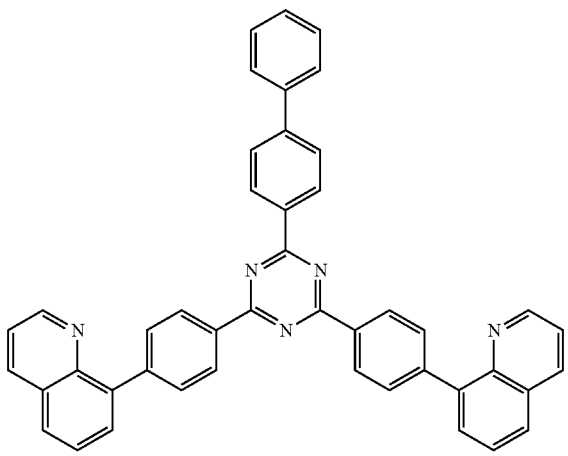
ET27
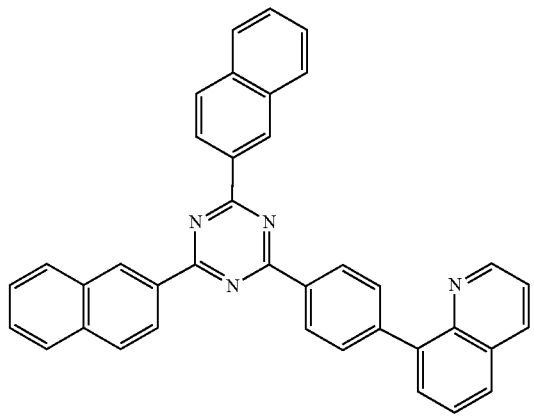
ET28
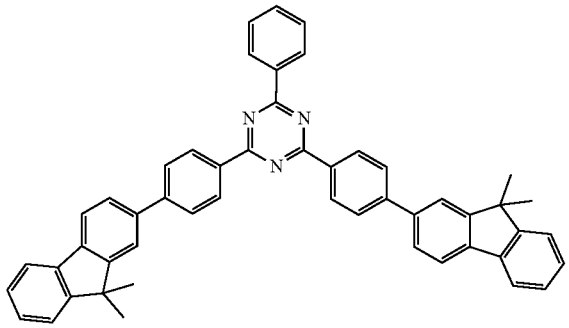

-continued
ET29
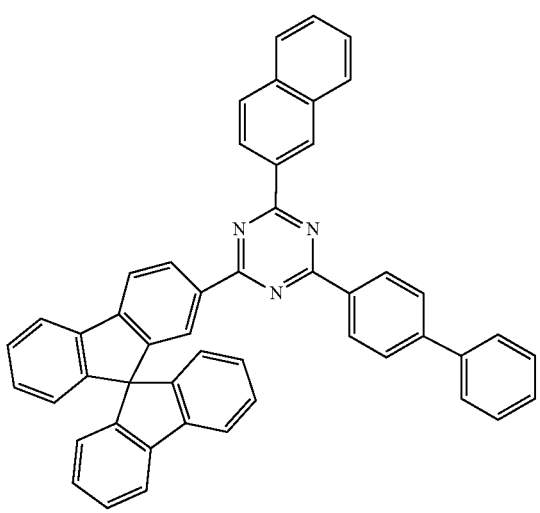
ET30
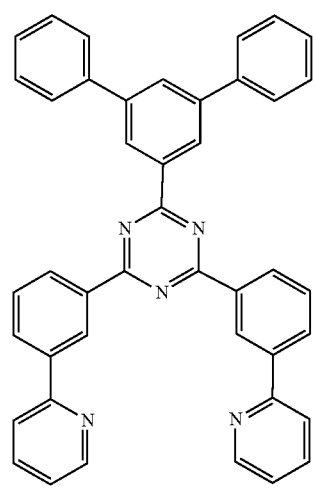
ET31
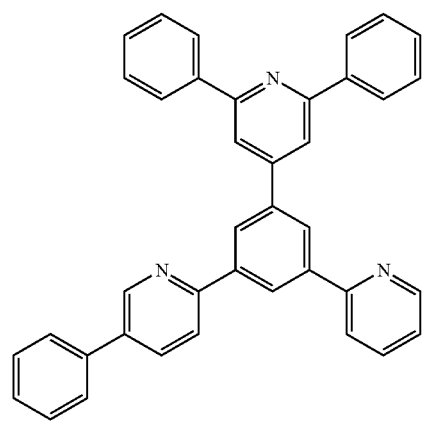
-continued
ET32
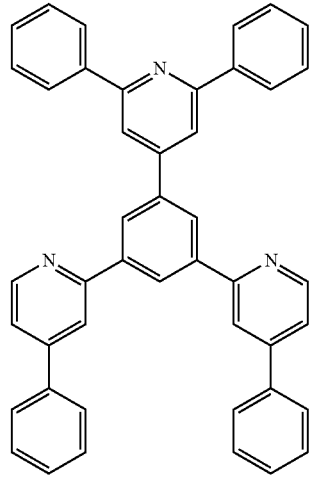
ET33
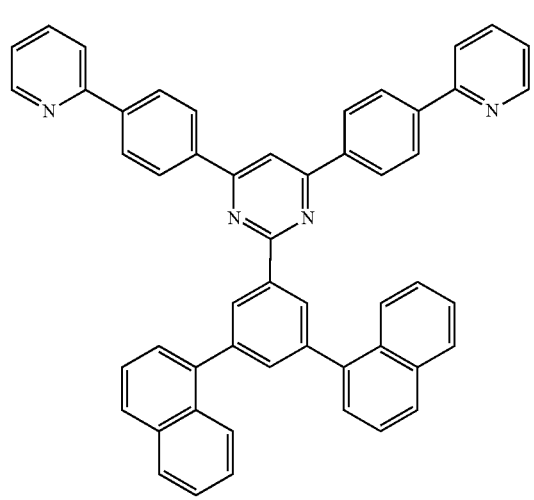
ET34
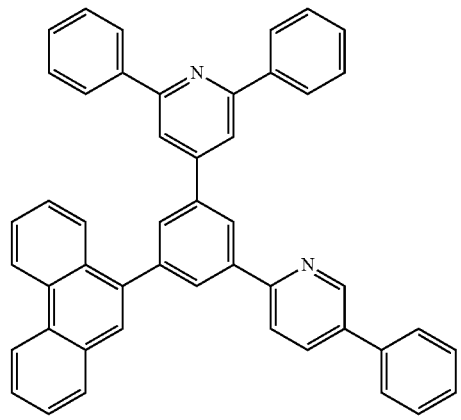

ET35

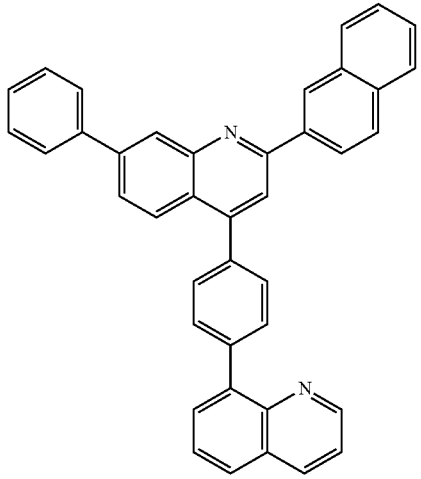

ET36

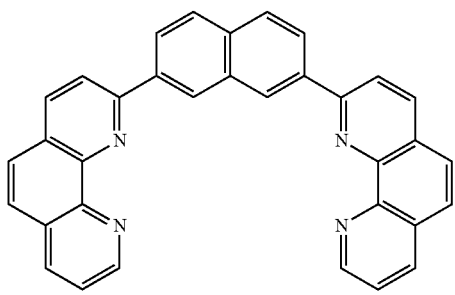

In some exemplary embodiments, the electron transport region may include at least one compound selected from 2,9-dimethyl-4,7-diphenyl-1,10-phenanthroline (BCP), 4,7-diphenyl-1,10-phenanthroline (Bphen), tris-(8-hydroxyquinoline)aluminum (Alq$_3$), bis(2-methyl-8-quinolinolato-N1, O8)-(1,1'-biphenyl-4-olato)aluminum (BAlq), 3-(biphenyl-4-yl)-5-(4-tert-butylphenyl)-4-phenyl-4H-1,2,4-triazole (TAZ), and 4-(naphthalen-1-yl)-3,5-diphenyl-4H-1,2,4-triazole (NTAZ):

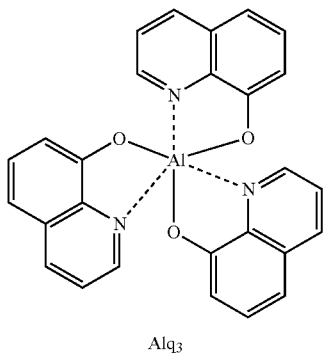

Alq$_3$

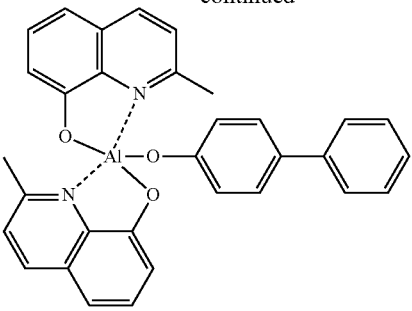

BAlq

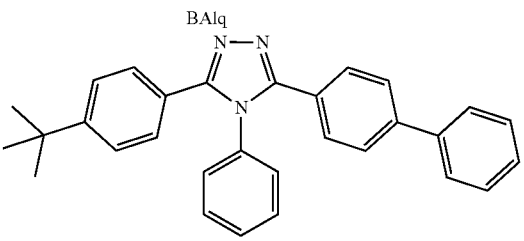

TAZ

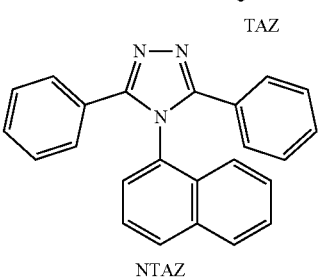

NTAZ

The thicknesses of the buffer layer, the hole blocking layer, or the electron control layer may each independently be in a range of about 20 Å to about 1,000 Å, and in some exemplary embodiments, about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, and in some exemplary embodiments, about 150 Å to about 500 Å. When the thickness of the electron transport layer is within any of these ranges, excellent electron transport characteristics may be obtained without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth metal complex. The alkali metal complex may include a metal ion selected from a lithium (Li) ion, a sodium (Na) ion, a potassium (K) ion, a rubidium (Rb) ion, and a cesium (Cs) ion. The alkaline earth metal complex may include a metal ion selected from a beryllium (Be) ion, a magnesium (Mg) ion, a calcium (Ca) ion, a strontium (Sr) ion, and a barium (Ba) ion. Each ligand coordinated with the metal ion of the alkali metal complex and the alkaline earth metal complex may independently be selected from hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, and cyclopentadiene, but the exemplary embodiments are not limited thereto.

For example, the metal-containing material may include a Li complex. The Li complex may include, e.g., Compound ET-D1 (lithium quinolate, LiQ) or Compound ET-D2:

ET-D1

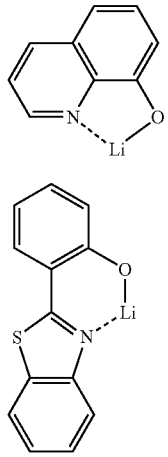

ET-D2

The electron transport region may include an electron injection layer that facilitates injection of electrons from the second electrode 190. The electron injection layer may be in direct contact with the second electrode 190. The electron injection layer may have i) a single-layered structure consisting of a single layer consisting of a single material, ii) a single-layered structure consisting of a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof. The alkali metal may be selected from Li, Na, K, Rb, and Cs. In some exemplary embodiments, the alkali metal may be Li, Na, or Cs. In one or more exemplary embodiments, the alkali metal may be Li or Cs, but the exemplary embodiments are not limited thereto. The alkaline earth metal may be selected from Mg, Ca, Sr, and Ba. The rare earth metal may be selected from Sc, Y, Ce, Tb, Yb, and Gd.

The alkali metal compound, the alkaline earth metal compound, and the rare earth metal compound may each independently be selected from oxides and halides (e.g., fluorides, chlorides, bromides, or iodines) of the alkali metal, the alkaline earth metal, and the rare earth metal, respectively. The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI.

In some exemplary embodiments, the alkali metal compound may be selected from LiF, $Li_2O$, NaF, LiI, NaI, CsI, and KI, but the exemplary embodiments are not limited thereto.

The alkaline earth-metal compound may be selected from alkaline earth-metal compounds, such as BaO, SrO, CaO, $Ba_xSr_{1-x}O$ (wherein $0<x<1$), and $Ba_xCa_{1-x}O$ (wherein $0<x<1$). In some exemplary embodiments, the alkaline earth metal compound may be selected from BaO, SrO, and CaO, but the exemplary embodiments are not limited thereto.

The rare earth metal compound may be selected from $YbF_3$, $ScF_3$, $Sc_2O_3$, $Y_2O_3$, $Ce_2O_3$, $GdF_3$, and $TbF_3$. In some exemplary embodiments, the rare earth metal compound may be selected from $YbF_3$, $ScF_3$, $TbF_3$, $YbI_3$, $ScI_3$, and $TbI_3$, but the exemplary embodiments are not limited thereto.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be selected from hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, and cyclopentadiene, but the exemplary embodiments are not limited thereto.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some exemplary embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, and in some exemplary embodiments, about 3 Å to about 90 Å. When the thickness of the electron injection layer is within any of these ranges, excellent electron injection characteristics may be obtained without a substantial increase in driving voltage.

Second Electrode 190

The second electrode 190 may be on the organic layer 150. In some exemplary embodiments, the second electrode 190 may be a cathode that is an electron injection electrode. In some exemplary embodiments, a material for forming the second electrode 190 may be a material having a low work function, for example, a metal, an alloy, an electrically conductive compound, or a combination thereof.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), silver-magnesium (Ag—Mg), ytterbium (Yb), silver-ytterbium (Ag—Yb), ITO, and IZO, but the exemplary embodiments are not limited thereto. The second electrode 190 may be a transmissive electrode, a semi-transmissive electrode, or a reflective electrode. The second electrode 190 may have a single-layered structure, or a multi-layered structure including two or more layers.

Figure 3:
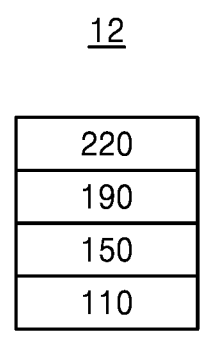
Figure 4:
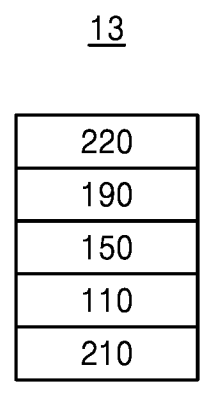

Description of FIGS. 2 to 4

Figure 2:
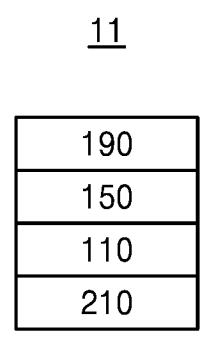

FIG. 2 is a schematic cross-sectional diagram of another exemplary embodiment of an organic light-emitting device constructed according to principles of the invention. FIG. 3 is a schematic cross-sectional diagram of a further exemplary embodiment of an organic light-emitting device constructed according to principles of the invention. FIG. 4 is a schematic cross-sectional diagram of yet another exemplary embodiment of an organic light-emitting device constructed according to principles of the invention.

Referring to FIG. 2, an organic light-emitting device 11 has a first capping layer 210, the first electrode 110, the organic layer 150, and the second electrode 190 structure, wherein the layers are sequentially stacked in this stated order. Referring to FIG. 3, an organic light-emitting device 12 has the first electrode 110, the organic layer 150, the second electrode 190, and a second capping layer 220 structure, wherein the layers are sequentially stacked in this stated order. Referring to FIG. 4, an organic light-emitting device 13 has the first capping layer 210, the first electrode 110, the organic layer 150, the second electrode 190, and the second capping layer 220 structure, wherein the layers are stacked in this stated order.

The first electrode 110, the organic layer 150, and the second electrode 190 illustrated in FIGS. 2 to 4 may be substantially the same as those illustrated in FIG. 1. In the organic light-emitting devices 11 and 13, light emitted from the emission layer in the organic layer 150 may pass through the first electrode 110 (which may be a semi-transmissive electrode or a transmissive electrode) and through the first capping layer 210 to the outside. In the organic light-emitting devices 12 and 13, light emitted from the emission layer in the organic layer 150 may pass through the second electrode 190 (which may be a semi-transmissive electrode or a transmissive electrode) and through the second capping layer 220 to the outside.

The first capping layer 210 and the second capping layer 220 may improve the external luminescence efficiency based on the principle of constructive interference. The first capping layer 210 and the second capping layer 220 may each independently be a capping layer including an organic material, an inorganic capping layer including an inorganic material, or a composite capping layer including an organic material and an inorganic material.

At least one of the first capping layer 210 and the second capping layer 220 may each independently include at least one material selected from carbocyclic compounds, heterocyclic compounds, amine-based compounds, porphine derivatives, phthalocyanine derivatives, naphthalocyanine derivatives, alkali metal complexes, and alkaline earth metal complexes. The carbocyclic compound, the heterocyclic compound, and the amine group-containing compound may optionally be substituted with a substituent containing at least one element selected from O, N, S, Se, Si, F, Cl, Br, and I. In some exemplary embodiments, at least one of the first capping layer 210 and the second capping layer 220 may each independently include an amine-based compound.

In one or more exemplary embodiments, at least one of the first capping layer 210 and the second capping layer 220 may each independently include a compound represented by Formula 201 or a compound represented by 202. In one or more exemplary embodiments, at least one of the first capping layer 210 and the second capping layer 220 may each independently include a compound selected from Compounds HT28 to HT33 and Compound CP1 to CP5, but the exemplary embodiments are not limited thereto:

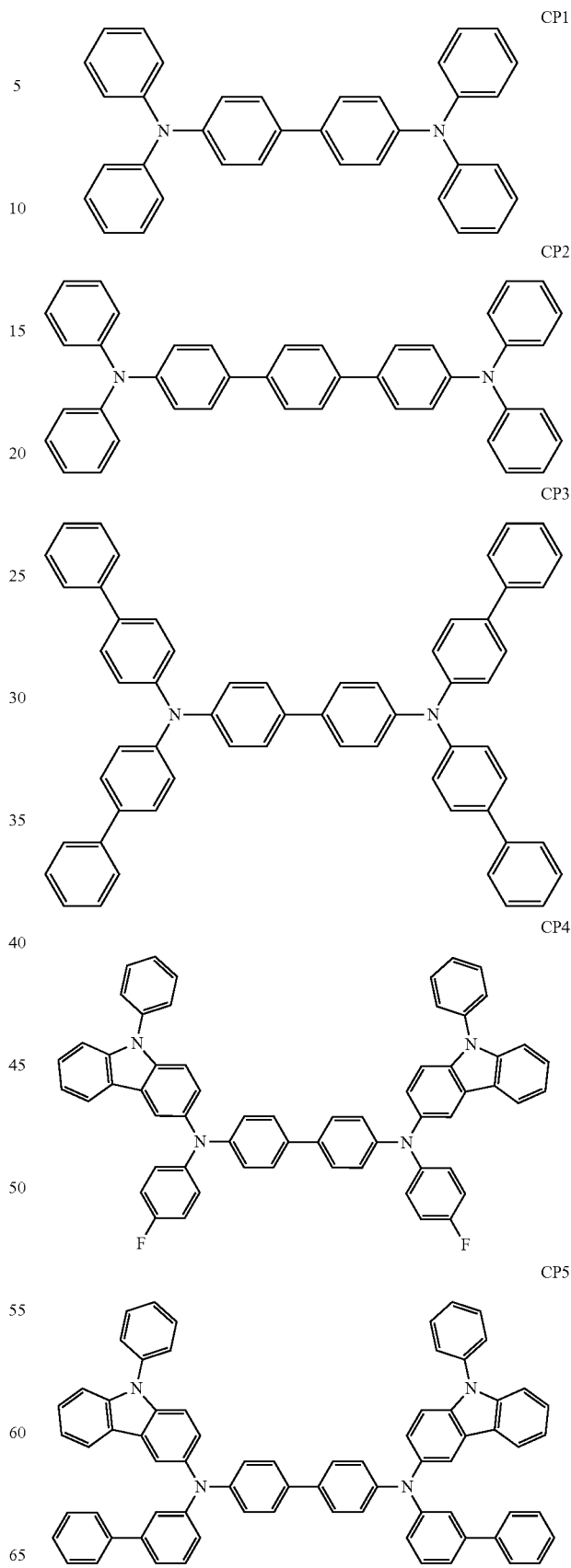

Hereinbefore, the organic light-emitting device has been described with reference to FIGS. 1 to 4, but the exemplary embodiments are not limited thereto. The layers constituting the hole transport region, the emission layer, and the layers constituting the electron transport region may be formed in a specific region by using one or more suitable methods such as vacuum deposition, spin coating, casting, Langmuir-Blodgett (LB) deposition, ink-jet printing, laser printing, and laser-induced thermal imaging.

When the layers constituting the hole transport region, the emission layer, and the layers constituting the electron transport region are each formed by vacuum deposition, the vacuum deposition may be performed at a deposition temperature in a range of about 100° C. to about 500° C. at a vacuum degree in a range of about $10^{-8}$ torr to about $10^{-3}$ torr, and at a deposition rate in a range of about 0.01 Angstroms per second (Å/sec) to about 100 Å/sec, depending on the material to be included in each layer and the structure of each layer to be formed. When the layers constituting the hole transport region, the emission layer, and the layers constituting the electron transport region are each formed by spin coating, the spin coating may be performed at a coating rate of about 2,000 revolutions per minute (rpm) to about 5,000 rpm and at a heat treatment temperature of about 80° C. to about 200° C., depending on the material to be included in each layer and the structure of each layer to be formed.

Figure 5:
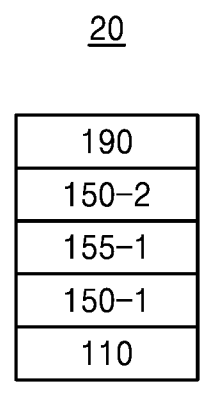
Figure 6:
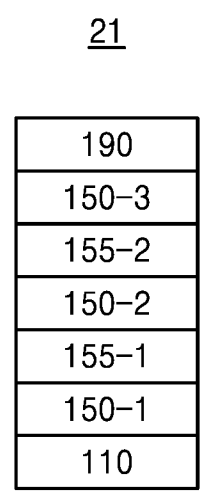

Description of FIGS. 5 and 6

FIG. 5 is a schematic cross-sectional diagram of still another exemplary embodiment of an organic light-emitting device constructed according to principles of the invention. FIG. 6 is a schematic cross-sectional diagram of a still further exemplary embodiment of an organic light-emitting device constructed according to principles of the invention. Specifically, FIG. 5 is a schematic cross-sectional view of an exemplary embodiment of an organic light-emitting device 20 when m is 2. FIG. 6 is a schematic cross-sectional view of an exemplary embodiment of an organic light-emitting device 21 when m is 3.

The organic light-emitting device 20 in FIG. 5 may include a structure in which the first electrode 110, a first emission unit 150-1, a first charge-generating layer 155-1, a second emission unit 150-2, and the second electrode 190 are sequentially layered in this stated order.

The organic light-emitting device 21 in FIG. 6 is an organic light-emitting device when m is 3. The organic light-emitting device 21 may include a structure in which the first electrode 110, a first emission unit 150-1, the first charge-generating layer 155-1, the second emission unit 150-2, a second charge-generating layer 155-2, a third emission unit 150-3, and the second electrode 190 are sequentially layered in this stated order.

The first electrode 110, the organic layer 150, and the second electrode 190 in FIGS. 5 and 6 may be understood by referring to the descriptions of the first electrode 110, the organic layer 150, and the second electrode 190 in FIG. 1 provided herein, and the first emission unit 150-1, the second emission unit 150-2, and the third emission unit 150-3 may be understood by referring to the description of the organic layer 150 in FIG. 1 provided herein.

The first charge-generating layer 155-1 and the second charge-generating layer 155-2 may each include at least one of the heterocyclic compounds of Formulae 1-1 to 1-3.

General Definitions Including Substituents

As used herein, the expression that the "(organic layer) includes at least one of the heterocyclic compounds" may be construed as meaning that the "(organic layer) may include one heterocyclic compound of Formulae 1-1 to 1-3 or two different heterocyclic compounds of Formulae 1-1 to 1-3".

The term "anthracene-based compound" as used herein refers to a compound including an anthracene ring in a molecule thereof. That is, the emission layer may include the anthracene ring described above.

The term "organic layer" as used herein refers to a single layer and/or a plurality of layers between the first electrode and the second electrode in an organic light-emitting device. A material included in the "organic layer" is not limited to an organic material.

The term "$C_1$-$C_{60}$ alkyl group" as used herein refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having a structure corresponding to the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having a structure corresponding to the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having a structure corresponding to the $C_2$-$C_{60}$ alkynyl group.

The term "$C_1$-$C_{60}$ alkoxy group" as used herein refers to a monovalent group represented by -$OA_{101}$ (wherein $A_{101}$ is a $C_1$-$C_1$ alkyl group). Examples thereof include a methoxy group, an ethoxy group, and an isopropyloxy group.

The term "$C_3$-$C_{10}$ cycloalkyl group" as used herein refers to a monovalent saturated hydrocarbon monocyclic group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having a structure corresponding to the $C_3$-$C_{10}$ cycloalkyl group.

The term "$C_1$-$C_{10}$ heterocycloalkyl group" as used herein refers to a monovalent monocyclic group including at least one heteroatom selected from N, O, Si, P, and S as a ring-forming atom and 1 to 10 carbon atoms. Examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having a structure corresponding to the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Examples thereof include a cyclopentenyl group, a cyclohexenyl group, and a cycloheptenyl group. The term "$C_3$-$C_{10}$ cycloalkenylene group" as used herein refers to a divalent group having a structure corresponding to the $C_3$-$C_{10}$ cycloalkenyl group.

The term "$C_1$-$C_{10}$ heterocycloalkenyl group" as used herein refers to a monovalent monocyclic group including at least one heteroatom selected from N, O, Si, P, and S as a ring-forming atom, 1 to 10 carbon atoms, and at least one double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein refers to a divalent group having a structure corresponding to the $C_1$-$C_{10}$ heterocycloalkyl group.

The term "$C_6$-$C_{60}$ aryl group" as used herein refers to a monovalent group having a carbocyclic aromatic system having 6 to 6 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein refers to a monovalent group having a heterocyclic aromatic system having at least one heteroatom selected from N, O, Si, P, and S as a ring-forming atom and 1 to 60 carbon atoms. The term "$C_1$-$C_{60}$ heteroarylene group" as used herein refers to a divalent group having a heterocyclic aromatic system having at least one heteroatom selected from N, O, Si, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused.

The term "$C_6$-$C_{60}$ aryloxy group" as used herein is represented by -$OA_{102}$ (wherein $A_{102}$ is the $C_6$-$C_{60}$ aryl group). The term "$C_6$-$C_{60}$ arylthio group" as used herein is represented by -$SA_{103}$ (wherein $A_{103}$ is the $C_6$-$C_{60}$ aryl group).

The term "monovalent non-aromatic fused polycyclic group" as used herein refers to a monovalent group that has two or more rings fused and only carbon atoms as ring forming atoms (e.g., 8 to 60 carbon atoms), wherein the entire molecular structure is non-aromatic. Examples of the monovalent non-aromatic fused polycyclic group may include a fluorenyl group. The term "divalent non-aromatic fused polycyclic group" as used herein refers to a divalent group having substantially a structure corresponding to the monovalent non-aromatic fused polycyclic group.

The term "monovalent non-aromatic fused heteropolycyclic group" as used herein refers to a monovalent group that has two or more fused rings and at least one heteroatom selected from N, O, Si, P, and S, in addition to carbon atoms (e.g., 1 to 60 carbon atoms), as a ring-forming atom, wherein the entire molecular structure is non-aromatic. Examples of the monovalent non-aromatic fused heteropolycyclic group may include a carbazolyl group. The term "divalent non-aromatic fused heteropolycyclic group" as used herein refers to a divalent group having substantially a structure corresponding to the monovalent non-aromatic fused heteropolycyclic group.

The term "$C_5$-$C_{60}$ carbocyclic group" as used herein refers to a monocyclic or polycyclic group having 5 to 60 carbon atoms only as ring-forming atoms. The $C_5$-$C_{60}$ carbocyclic group may be an aromatic carbocyclic group or a non-aromatic carbocyclic group. The term "$C_5$-$C_{60}$ carbocyclic group" as used herein refers to a ring (e.g., a benzene group), a monovalent group (e.g., a phenyl group), or a divalent group (e.g., a phenylene group). Also, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having substantially a structure corresponding to the $C_5$-$C_{60}$ carbocyclic group, except that at least one heteroatom selected from N, O, Si, P, and S is used as a ring-forming atom, in addition to carbon atoms (e.g., 1 to 60 carbon atoms).

The term "π electron-depleted nitrogen-containing ring" as used herein refers to a $C_1$-$C_{60}$ heterocyclic group having at least one *—N=*' moiety as a ring-forming moiety. The term "π electron-depleted nitrogen-containing $C_1$-$C_{30}$ cyclic group" as used herein refers to a $C_1$-$C_{30}$ heterocyclic group including at least one *—N=*' moiety.

For example, the π electron-depleted nitrogen-containing $C_1$-$C_{30}$ cyclic group may be a) a first ring, b) a fused ring in which at least two first rings are fused, or c) a fused ring in which at least one first ring and at least one second ring are fused, the first ring may be an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, a tetrazine group, a pentazine group, a hexazine group, or a thiadiazole group, and the second ring may be a benzene group, a cyclopentadiene group, a pyrrole group, a furan group, a thiophene group, or a silole group.

In some exemplary embodiments, the π electron-depleted nitrogen-containing $C_1$-$C_{30}$ cyclic group may be one of an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, an acridine group, a pyridopyrazine group, and groups represented by Formulae 2-1 to 2-17:

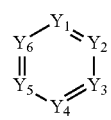

2-1

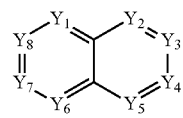

2-2

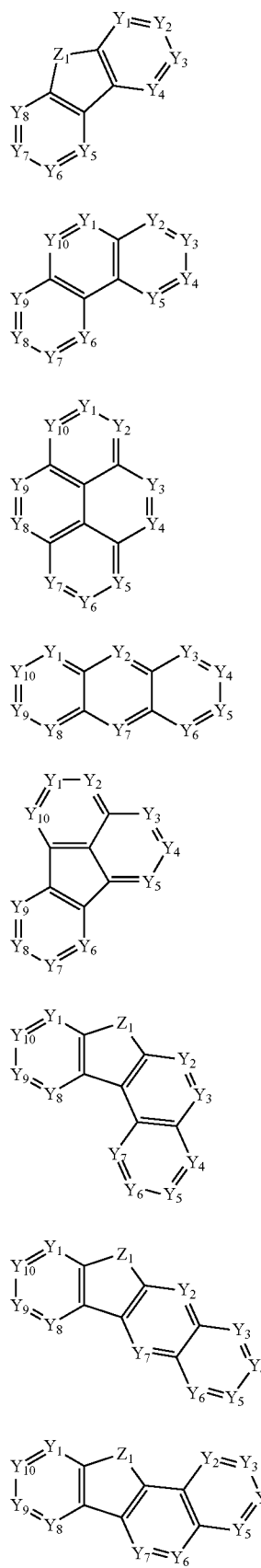
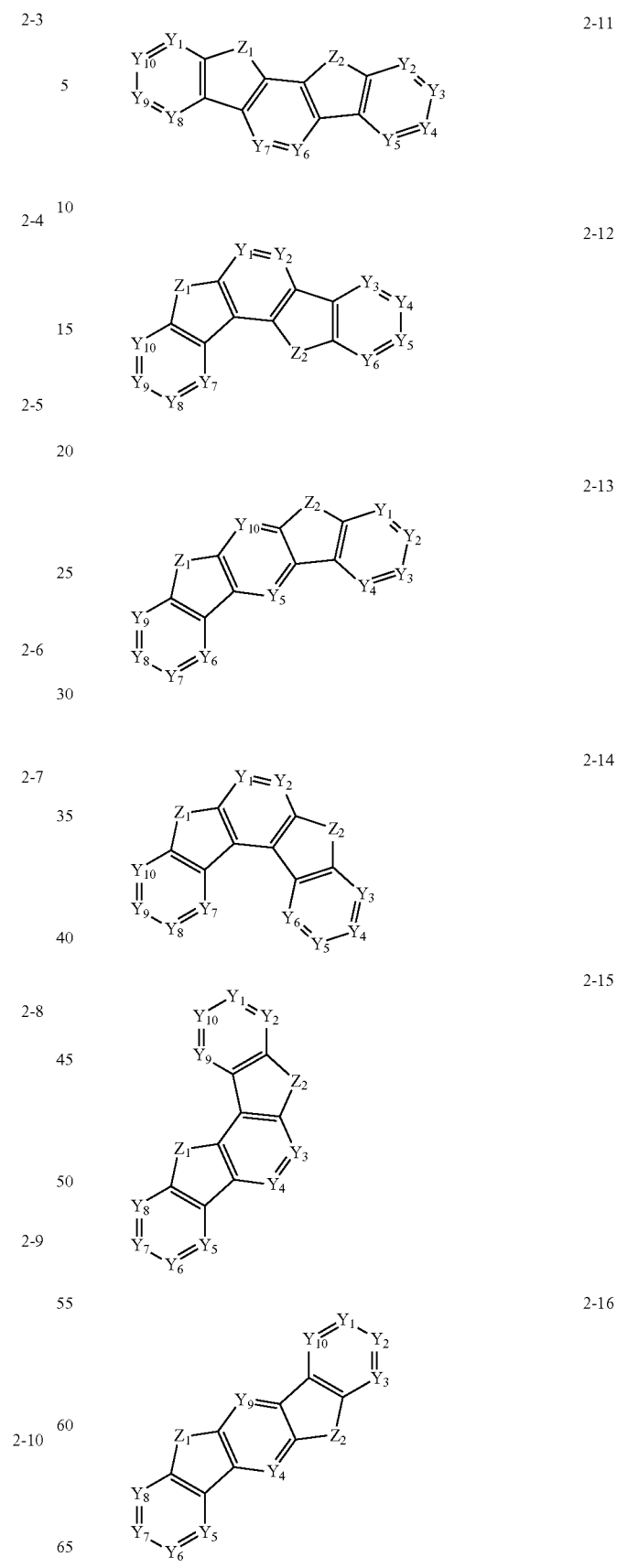

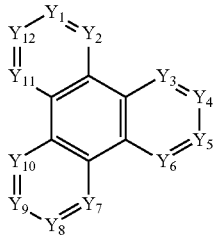

2-17 wherein, in Formulae 2-1 to 2-17, $Z_1$ may be O, S, $N(R_{1a})$, $C(R_{1a})(R_{1b})$, or $Si(R_{1a})(R_{1b})$,
$Z_2$ may be O, S, $N(R_{2a})$, $C(R_{2a})(R_{2b})$, or $Si(R_{2a})(R_{2b})$,
$Y_1$ may be $C(R_{31})$ or N,
$Y_2$ may be $C(R_{32})$ or N,
$Y_3$ may be $C(R_{33})$ or N,
$Y_4$ may be $C(R_{34})$ or N,
$Y_5$ may be $C(R_{35})$ or N,
$Y_6$ may be $C(R36)$ or N,
$Y_7$ may be $C(R_{37})$ or N,
$Y_8$ may be $C(R_{38})$ or N,
$Y_9$ may be $C(R_{39})$ or N,
$Y_{10}$ may be $C(R_{40})$ or N,
$Y_{11}$ may be $C(R41)$ or N,
$Y_{12}$ may be $C(R_{42})$ or N,
in Formula 2-1, at least one of $Y_1$ to $Y_6$ may be N,
in Formulae 2-2 and 2-3, at least one of $Y_1$ to $Y_8$ may be N,
in Formulae 2-4 and 2-16, at least one of $Y_1$ to $Y_{10}$ may be N, and
in Formula 2-17, at least one of $Y_1$ to $Y_{12}$ may be N.

$R_{1a}$, $R_{1b}$, $R_{2a}$, $R_{2b}$, and $R_{31}$ to $R_{42}$ may respectively be understood by referring to the descriptions of $R_{1a}$, $R_{1b}$, $R_{2a}$, $R_{2b}$, and $R_{31}$ to $R_{42}$ provided herein.

The term "π electron-rich nitrogen-containing $C_3$-$C_{60}$ cyclic group" as used herein refers to a $C_1$-$C_{60}$ heterocyclic group not including a *—N=*' moiety.

In some exemplary embodiments, the π electron-rich $C_3$-$C_{60}$ cyclic group may be a) second ring or b) a fused ring in which at least two second rings are fused, and
the second ring may be a benzene group, a cyclopentadiene group, a pyrrole group, a furan group, a thiophene group, or a silole group.

In one or more exemplary embodiments, the π electron-rich $C_3$-$C_{60}$ cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonapthothiophene group, (an indolo)phenanthrene group, a (benzofurano)phenanthrene group, or a (benzothieno)phenanthrene group.

As used herein, at least one of substituents of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic fused polycyclic group, the substituted divalent non-aromatic fused heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, and a monovalent non-aromatic fused heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, and a monovalent non-aromatic fused heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may each independently be selected from hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic fused polycyclic group; a monovalent non-aromatic fused heteropolycyclic group; a $C_1$-$C_{60}$ alkyl group substituted with at least one selected from deuterium, —F, and a cyano group; a $C_6$-$C_{60}$ aryl group substituted with at least one selected from deuterium, —F, and a cyano group; a biphenyl group; and a terphenyl group.

"Ph" used herein represents a phenyl group, "Me" used herein represents a methyl group, "Et" used herein represents an ethyl group, "ter-Bu" or "Bu$^t$" used herein represents a tert-butyl group, and "OMe" used herein represents a methoxy group.

The term "biphenyl group" as used herein refers to a phenyl group substituted with at least one phenyl group. The "biphenyl group" belongs to "a substituted phenyl group" having a "$C_6$-$C_{60}$ aryl group" as a substituent.

The term "terphenyl group" as used herein refers to a phenyl group substituted with at least one phenyl group. The "terphenyl group" belongs to "a substituted phenyl group" having a "$C_6$-$C_{60}$ aryl group substituted with a $C_6$-$C_{60}$ aryl group" as a substituent.

The symbols * and *' as used herein, unless defined otherwise, refer to a binding site to an adjacent atom in a corresponding formula.

As used herein, the term "atom" may mean an element or its corresponding radical bonded to one or more other atoms.

The terms "hydrogen" and "deuterium" refer to their respective atoms and corresponding radicals, and the terms "—F, —Cl, —Br, and —I" are radicals of, respectively, fluorine, chlorine, bromine, and iodine. The term "deuterium" as a radical may be abbreviated "-D"

As used herein, a substituent for a monovalent group, e.g., alkyl, may also be, independently, a substituent for a corresponding divalent group, e.g., alkylene."

Hereinafter, compounds and an organic light-emitting device according to one or more exemplary embodiments, will be described in more detail with reference to Synthesis Examples and Examples. The wording "B was used instead of A" used in describing Synthesis Examples means that an amount of B used was identical to an amount of A used in terms of molar equivalents.

EXAMPLES

Synthesis Example 1: Synthesis of Compound 1

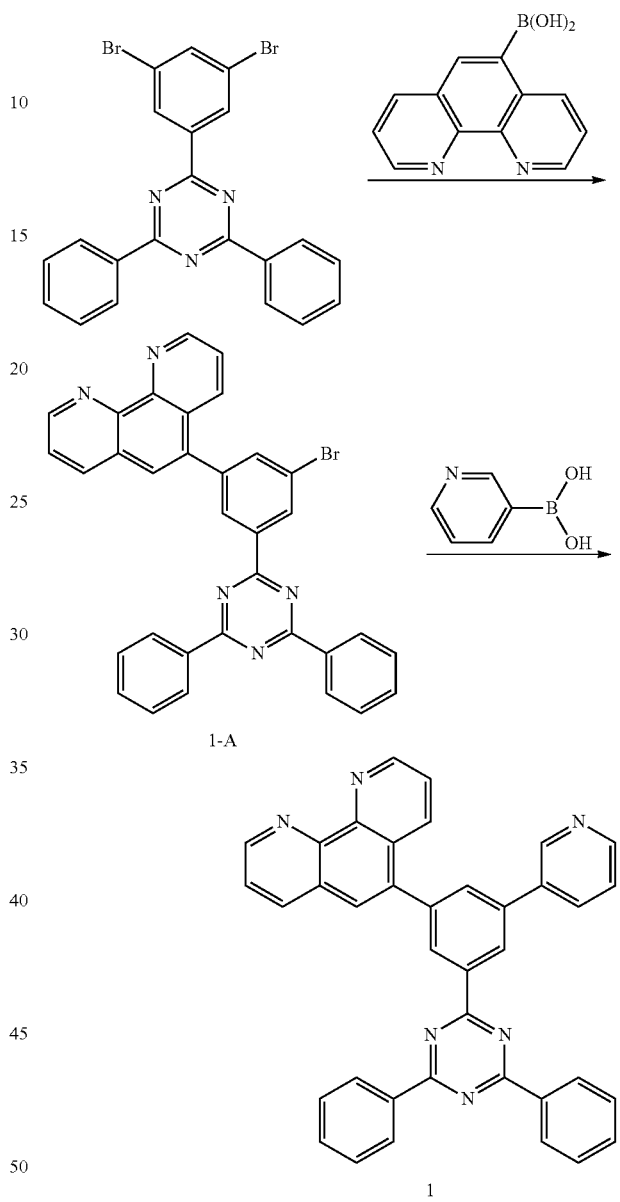

Synthesis of Intermediate 1-A 4.6 grams (g, 10 mmol) of 2-(3,5-dibromophenyl)-4,6-diphenyl-1,3,5-triazine, 2.4 g (11 mmol) of (1,10-phenanthrolin-5-yl)boronic acid, 2.2 g (20 mmol) of potassium carbonate, and 0.41 g (0.35 mmol) of tetrakis(triphenyl phosphine)palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (dichloromethane and hexane at a volume ratio of 10:1), thereby obtaining 3.7 g (6.5 mmol) of Intermediate 1-A. (yield: 65%)

Synthesis of Compound 1

5.7 g (10 mmol) of Intermediate 1-A, 1.4 g (12 mmol) of pyridine-3-ylboronic acid, 1.4 g (10 mmol) of potassium carbonate, and 0.41 g (0.35 mmol) of tetrakis(triphenyl phosphine)palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess chloroform and distilled water to obtain an organic layer. The obtained organic layer was dried using anhydrous magnesium sulfate and separated and purified through column chromatography (chloroform), thereby obtaining 4.0 g (7.1 mmol) of Compound 1. (yield: 71%)

Synthesis Example 2: Synthesis of Compound 2

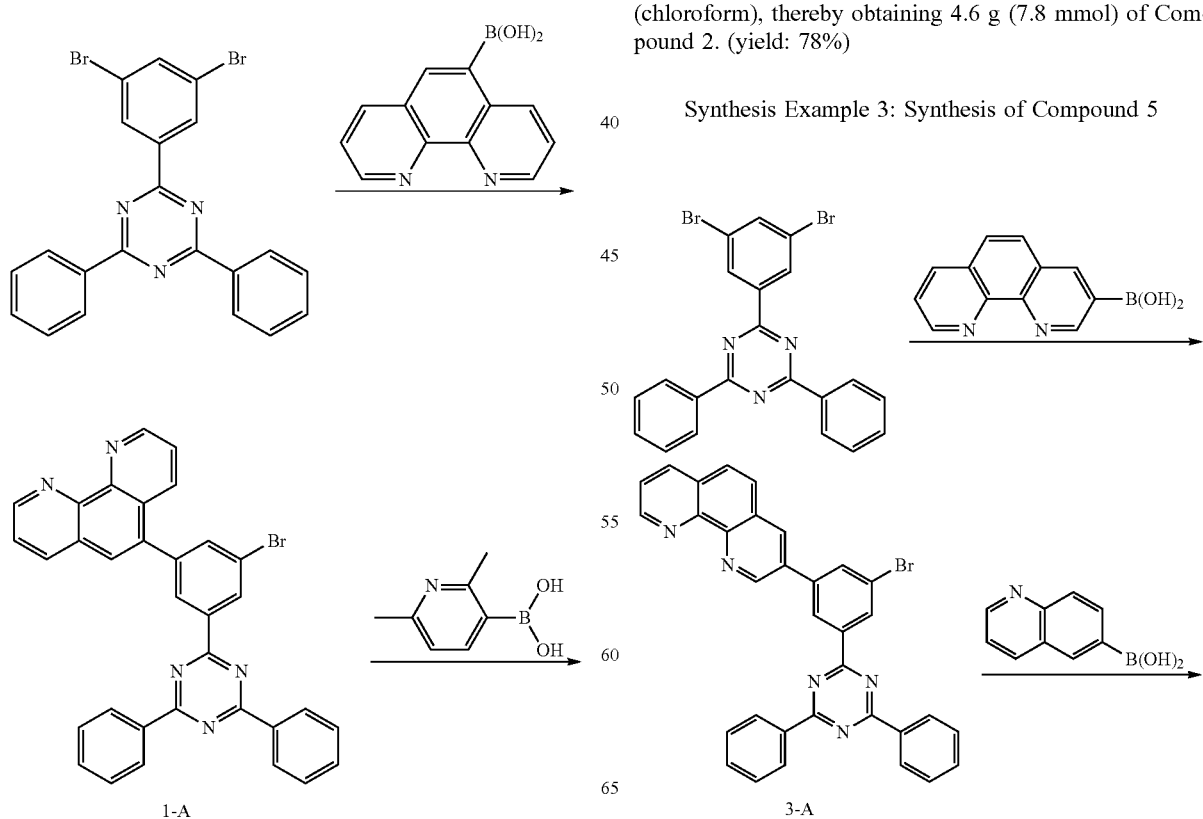

5.7 g (10 mmol) of Intermediate 1-A, 1.8 g (12 mmol) of 2,6-dimethylpyridin-3-ylboronic acid, 1.4 g (10 mmol) of potassium carbonate, and 0.41 g (0.35 mmol) of tetrakis (triphenyl phosphine)palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (chloroform), thereby obtaining 4.6 g (7.8 mmol) of Compound 2. (yield: 78%)

Synthesis Example 3: Synthesis of Compound 5

Synthesis Example 4: Synthesis of Compound 9

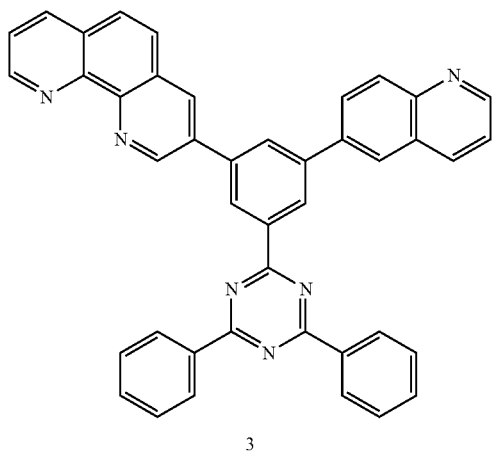 [SMILES: c1ccc(-c2nc(-c3ccccc3)nc(-c3cc(-c4ccc5ncccc5c4)cc(-c4cnc5c(ccc6cccnc65)c4)c3)n2)cc1]

3

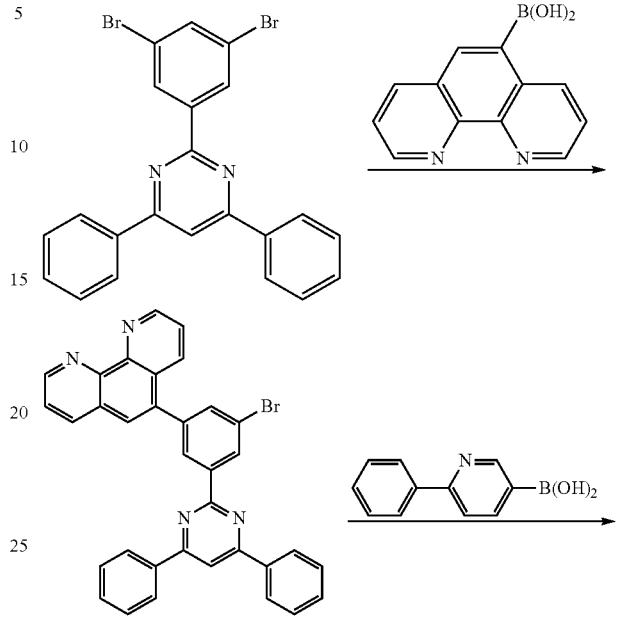

9-A

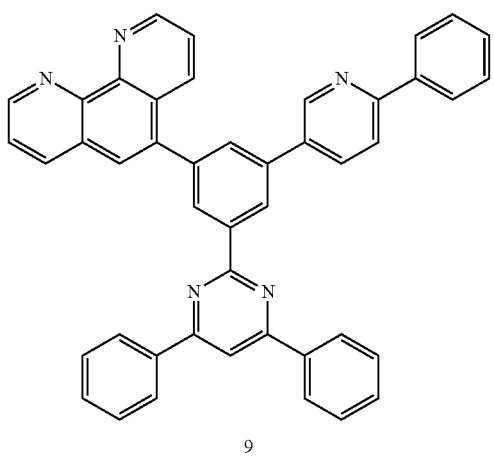 [SMILES: c1ccc(-c2ccc(-c3cc(-c4nc(-c5ccccc5)cc(-c5ccccc5)n4)cc(-c4cc5cccnc5c5ncccc45)c3)cn2)cc1]

9

Synthesis of Intermediate 3-A 4.6 g (10 mmol) of 2-(3,5-dibromophenyl)-4,6-diphenyl-1,3,5-triazine, 2.6 g (12 mmol) of (1,10-phenanthrolin-3-yl) boronic acid, 2.8 g (20 mmol) of potassium carbonate, and 0.41 g (0.35 mmol) of tetrakis(triphenyl phosphine)palladium (0) (Pd(PPh$_3$)$_4$) were added to a Schlenk tube in vacuum and dried for 2 hours, and the resultant was dissolved in 100 mL of dimethyl formamide (DMF). 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (dichloromethane), thereby obtaining 2.9 g (5.2 mmol) of Intermediate 3-A. (yield: 52%)

Synthesis of Compound 3

5.7 g (10 mmol) of Intermediate 3-A, 1.9 g (11 mmol) of quinolin-6-ylboronic acid, 2.8 g (20 mmol) of potassium carbonate, and 0.41 g (0.35 mmol) of tetrakis(triphenyl phosphine)palladium (0) (Pd(PPh$_3$)$_4$) were added to a Schlenk tube in vacuum and dried for 2 hours, and the resultant was dissolved in 100 mL of 1,4-dioxane. 20 mL of anhydrous ethanol was added thereto under nitrogen atmosphere, followed by stirring at a temperature of 120° C. for 48 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (dichloromethane), thereby obtaining 2.7 g (4.4 mmol) of Compound 3. (yield: 44%)

Synthesis of Intermediate 9-A 4.7 g (10 mmol) of 2-(3,5-dibromophenyl)-4,6-diphenylpyrimidine, 2.4 g (11 mmol) of (1,10-phenanthrolin-5-yl)boronic acid, 2.2 g (20 mmol) of potassium carbonate, and 0.41 g (0.35 mmol) of tetrakis(triphenyl phosphine) palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (dichloromethane and hexane at a volume ratio of 5:1), thereby obtaining 3.6 g (6.3 mmol) of Intermediate 9-A. (yield: 63%)

Synthesis of Compound 9

5.7 g (10 mmol) of Intermediate 9-A, 2.4 g (12 mmol) of (6-phenylpyridin-3-yl)boronic acid, 1.4 g (10 mmol) of potassium carbonate, and 0.41 g (0.35 mmol) of tetrakis (triphenyl phosphine)palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (dichloromethane), thereby obtaining 1.9 g (3.0 mmol) of Compound 9. (yield: 30%).

Synthesis Example 5: Synthesis of Compound 22 romethane and distilled water to obtain an organic layer. The obtained organic layer was dried using anhydrous magnesium sulfate and separated and purified through column chromatography (dichloromethane and hexane at a volume ratio of 2:1), thereby obtaining 3.6 g (8.8 mmol) of Intermediate 22-A. (yield: 88%)

Synthesis of Intermediate 22-B 4.1 g (10 mmol) of Intermediate 22-A was dissolved under nitrogen atmosphere in a mixture of toluene (50 mL) and tetrahydrofuran (THF, 10 mL), and n-butyl lithium (5 mL, 1.2 eq., in 2.5 M hexane solution) was slowly added thereto at a temperature of −78° C. The mixture was stirred at a temperature of −78° C. for 1 hour, and trimethyl borate (1.2 mmol) was added thereto. 12 mL (2 M solution) of hydrochloric acid was added thereto, and the temperature was raised to room temperature, and an organic layer separated therefrom was washed using distilled water and brine solution and dried using anhydrous magnesium sulfate, and a solvent was removed therefrom under reduced pressure. The resulting product was washed several times using hot n-hexane to thereby obtain 2.6 g (6.9 mmol) of Intermediate 22-B. (yield: 69%)

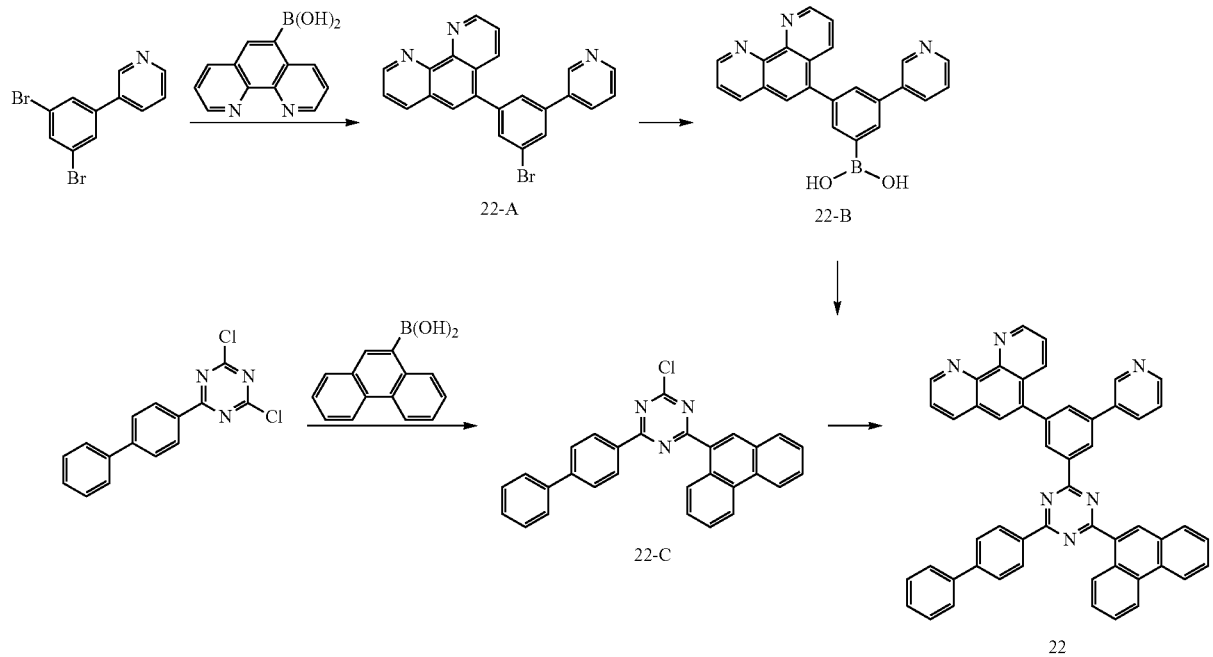

Synthesis of Intermediate 22-A 3.1 g (10 mmol) of 3-(3,5-dibromophenyl)pyridine, 2.4 g (11 mmol) of (1,10-phenanthrolin-5-yl)boronic acid, 2.8 g (20 mmol) of potassium carbonate, and 0.41 g (0.35 mmol) of tetrakis(triphenyl phosphine)palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 80° C. for 24 hours. Once the mixture was cooled to room temperature, the solvent was removed under reduced pressure, and the product was washed using excess dichlo- Synthesis of Intermediate 22-C 3.0 g (10 mmol) of [1,1'-biphenyl]-4-yl)-4,6-dichloro-1, 3,5-triazine, 2.6 g (12 mmol) of phenanthren-9-ylboronic acid, 1.4 g (10 mmol) of potassium carbonate, and 0.41 g (0.35 mmol) of tetrakis(triphenyl phosphine)palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and separated and purified through column chromatography (dichloromethane), thereby obtaining 2.4 g (5.5 mmol) of Intermediate 22-C. (yield: 55%)

Synthesis of Compound 22

3.8 g (10 mmol) of Intermediate 22-B, 4.4 g (10 mmol) of Intermediate 22-C, 2.2 g (20 mmol) of potassium carbonate, and 0.41 g (0.35 mmol) of tetrakis(triphenyl phosphine) palladium (0) (Pd(PPh$_3$)$_4$) were added to a Schlenk tube in vacuum and dried for 2 hours, and the resultant was dissolved in 100 mL of toluene. 20 mL of anhydrous ethanol was added thereto under nitrogen atmosphere, followed by stirring at a temperature of 100° C. for 24 hours. Once the mixture was cooled to room temperature, the solvent was removed therefrom under reduced pressure, and the product was washed using excess dichloromethane and distilled water to obtain an organic layer. The obtained organic layer was dried using anhydrous magnesium sulfate and purified through column chromatography (chloroform), thereby obtaining 1.8 g (2.5 mmol) of Compound 22. (yield: 25%)

The $^1$H NMR results of the synthesized compounds are shown in Table 1. Methods of synthesizing compounds other than compounds shown in Table 1 may be easily understood to those skilled in the art by referring to the synthesis pathways and raw materials described above.

TABLE 1

| Compound | H NMR (δ) |
|---|---|
| 1 | 9.24 (s, 1H), 8.80 (d, 1H), 8.70-8.67 (m, 2H), 8.50-8.36 (m, 7H), 8.04 (s, 3H), 7.62-7.50 (m, 9H), 7.32 (s, 1H) |
| 2 | 8.80 (d, 1H), 8.67 (d, 1H), 8.50 (d, 1H), 8.44 (d, 1H), 8.36 (dd, 4H), 8.13 (d, 1H), 8.01 (s, 3H), 7.67-7.55 (m, 8H), 7.33 (s, 1H), 7.18 (d, 1H) |
| 3 | 8.91 (d, 1H), 8.80 (d, 1H), 8.45-8.36 (m, 7H), 8.26 (s, 1H), 8.20 (s, 1H), 8.15-8.09 (m, 2H), 8.02 (s, 3H), 7.91-7.88 (m, 2H), 7.50-7.40 (m, 8H) |
| 9 | 9.01 (s, 1H), 8.88 (d, 1H), 8.71 (d, 1H), 8.50-8.44 (m, 2H), 8.33 (d, 2H), 8.23 (s, 1H), 8.07 (s, 3H), 8.00-7.94 (m, 5H), 7.81 (d, 1H), 7.59-7.55 (m, 11H), 7.29 (s, 1H) |
| 22 | 9.24 (s, 1H), 9.08 (d, 1H), 8.84 (d, 2H), 8.70-8.67 (dd, 2H), 8.51-8.45 (m, 3H), 8.17 (d, 1H), 8.01 (s, 3H), 7.96-7.90 (m, 4H), 7.75-7.41 (m, 12H), 7.32 (d, 1H), 7.25 (d, 2H) |

Comparative Example 1

A 15 Ω/cm$_2$ (1,200 Å) ITO glass substrate (available from Corning Co., Ltd, of Shanghai, China) was cut to a size of 50 millimeters (mm)×50 mm×0.5 mm, sonicated in isopropyl alcohol and pure water for 10 minutes in each solvent, and cleaned by exposure to ultraviolet rays with ozone for 10 minutes. Then, the glass substrate was mounted to a vacuum-deposition apparatus.

HAT-CN was vacuum-deposited on the ITO anode formed on the glass substrate to form a hole injection layer having a thickness of 100 Å. Then, HT1 was deposited on the hole injection layer to form a hole transport layer having a thickness of 300 Å.

HOST 1 (as a host) and DOPANT 1 (as a dopant) were deposited on the hole transport layer at a weight ratio of 97:3 to form an emission layer having a thickness of 300 Å.

Subsequently, the emission layer was deposited on 2,4,6-tris(biphenyl-3-yl)-1,3,5-triazine (T2T) to form a hole blocking layer having a thickness of 100 Å, and 2-[3,5-bis(1-phenylbenzimidazol-2-yl)phenyl]-1-phenylbenzimidazole (TPBi) was deposited on the hole blocking layer to form an electron transport layer having a thickness of 550 Å.

Lithium fluoride (LiF) was deposited on the electron transport layer to form an electron injection layer having a thickness of 8 Å, and Al was vacuum-deposited on the electron injection layer to form a LiF/Al electrode having a thickness of 1,000 Å, thereby completing the manufacture of an organic light-emitting device.

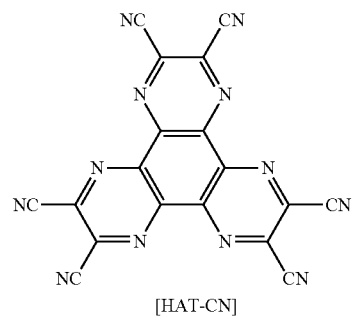

[HAT-CN]

-continued

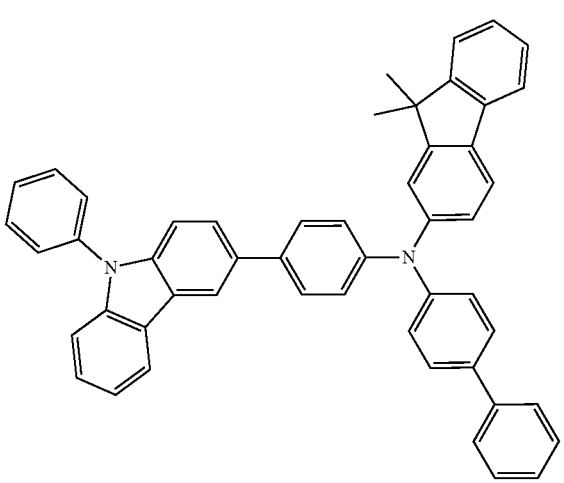

[HT1]

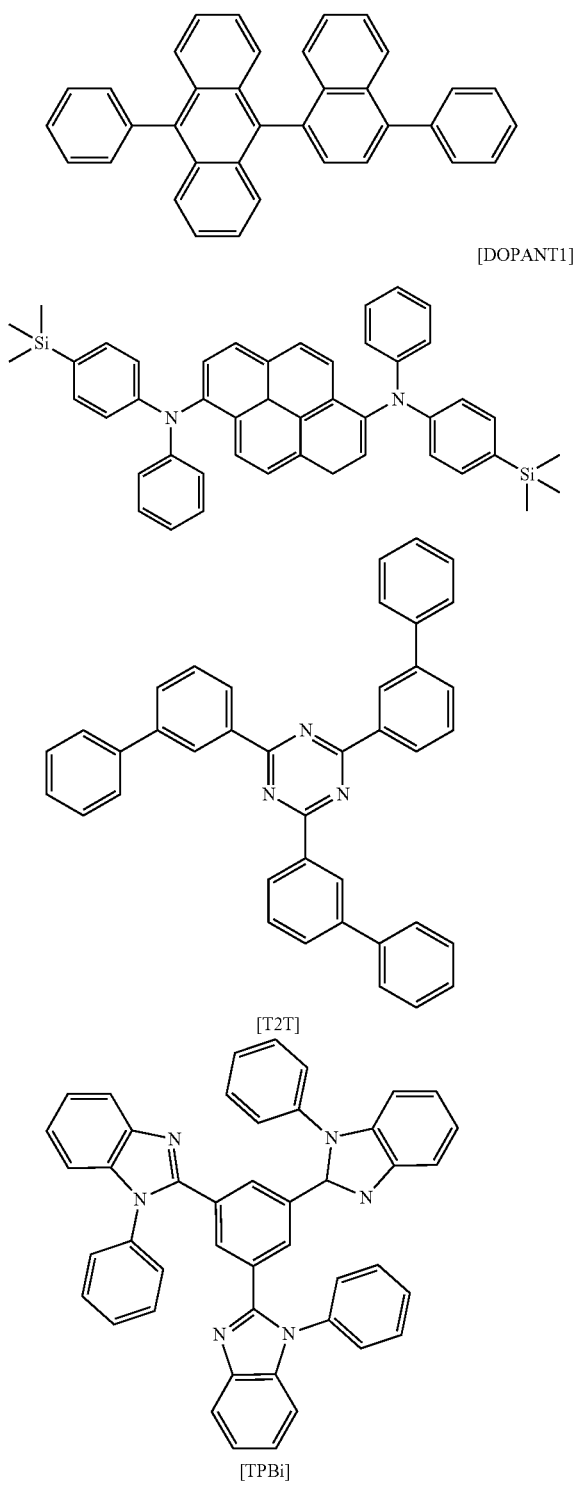

[HOST1]

[DOPANT1]

[T2T]

[TPBi]

Examples 1 to 5 and Comparative Examples 2 to 9

Organic light-emitting devices were manufactured in substantially the same manner as in Comparative Example 1, except that Compounds shown in Table 2 was used instead of TPBi when forming an electron transport layer.

Evaluation Example 1

The maximum external quantum efficiency (EQE), driving voltage, and current density were measured at a luminance of 1,000 nit to evaluate the characteristics of the organic light-emitting devices manufactured in Examples 1 to 5 and Comparative Examples 1 to 9. The device lifespan was compared by measuring time for the luminance to reduce by 95% using a current density at a luminance of 1,000 nit. The driving voltage of the organic light-emitting devices were measured using a source meter (Keithley Instrument, sold under the trade designation 2400 series by Tektronix, Inc., of Beaverton, Oregon). The maximum external quantum yield of the organic light-emitting devices were measured using Hammamastu Absolute PL Quantum Yield Measurement System sold under the trade designation C9920-2-12 by Hamamatsu Photonics Inc. of Hamamatsu-city, Japan. In evaluation of the maximum external quantum yield, luminance/current density was measured using a luminance meter with calibration of wavelength sensitivity, and the maximum external quantum yield was calculated on the assumption of the angular luminance distribution (Lambertian) assuming a complete diffusion reflecting surface. The evaluation results of the organic light-emitting devices are shown in Table 2.

TABLE 2

|  | Electron transport layer | External quantum efficiency (%) | Driving voltage (V) | Lifespan T95 (h) |
|---|---|---|---|---|
| Example 1 | Compound 1 | 7.2 | 3.8 | 48 |
| Example 2 | Compound 2 | 8.4 | 3.5 | 82 |
| Example 3 | Compound 5 | 7.7 | 3.7 | 69 |
| Example 4 | Compound 9 | 6.2 | 4.4 | 36 |
| Example 5 | Compound 22 | 7.6 | 4.0 | 64 |
| Comparative Example 1 | TPBi | 4.0 | 5.1 | 3 |
| Comparative Example 2 | Compound A | 6.4 | 4.2 | 30 |
| Comparative Example 3 | Compound B | 5.8 | 4.6 | 18 |
| Comparative Example 4 | Compound C | 6.2 | 4.3 | 21 |
| Comparative Example 5 | Compound D | 5.1 | 4.6 | 13 |
| Comparative Example 6 | Compound E | 6.2 | 4.4 | 32 |
| Comparative Example 7 | Compound F | 6.4 | 4.3 | 15 |
| Comparative Example 8 | Compound G | 3.8 | 5.0 | 8 |
| Comparative Example 9 | Compound H | 5.1 | 4.8 | 12 |

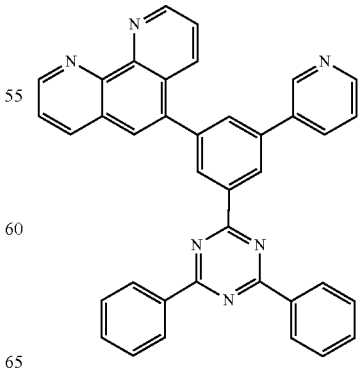

1

TABLE 2-continued
| Electron transport layer | External quantum efficiency (%) | Driving voltage (V) | Lifespan T95 (h) |
|---|---|---|---|
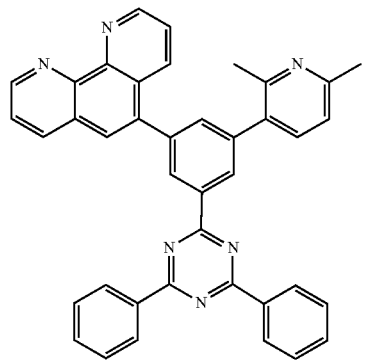
2
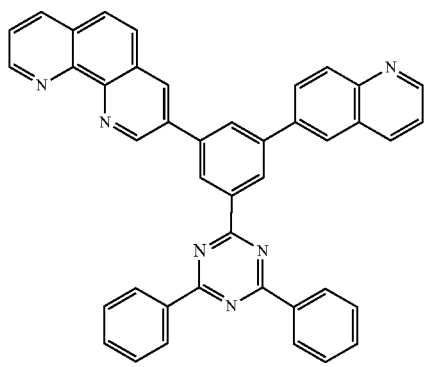
5
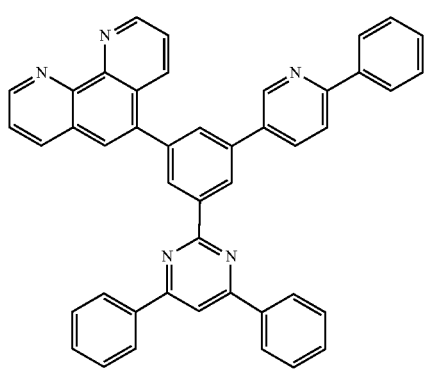
9
TABLE 2-continued
| Electron transport layer | External quantum efficiency (%) | Driving voltage (V) | Lifespan T95 (h) |
|---|---|---|---|
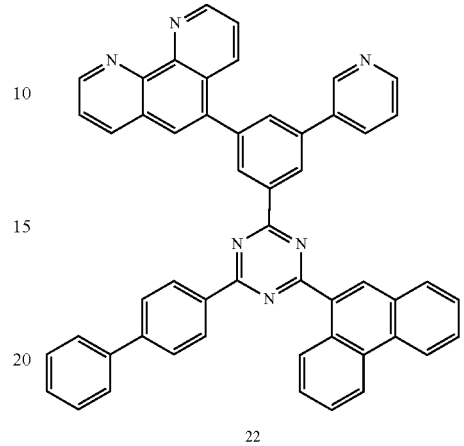
22
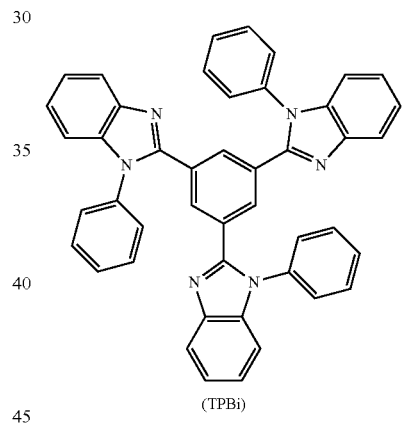
(TPBi)
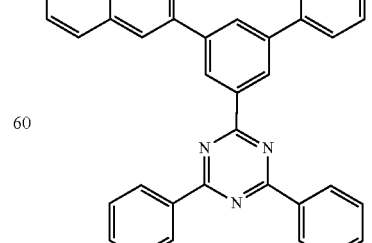
A TABLE 2-continued

| Electron transport layer | External quantum efficiency (%) | Driving voltage (V) | Lifespan T95 (h) |
|---|---|---|---|

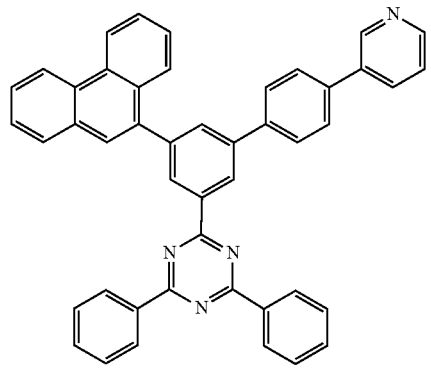
B

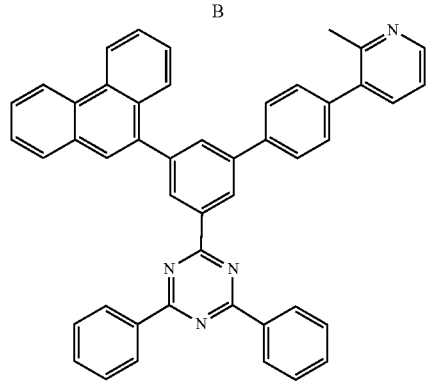
C

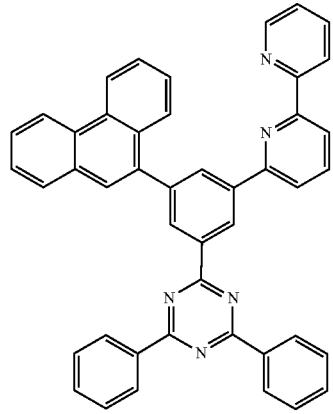
D

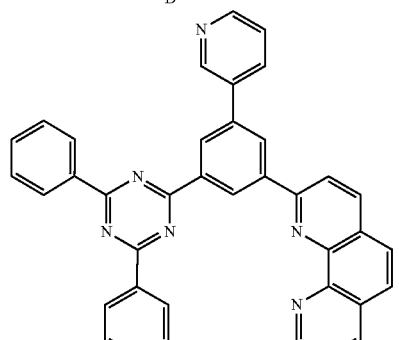
E

TABLE 2-continued

| Electron transport layer | External quantum efficiency (%) | Driving voltage (V) | Lifespan T95 (h) |
|---|---|---|---|

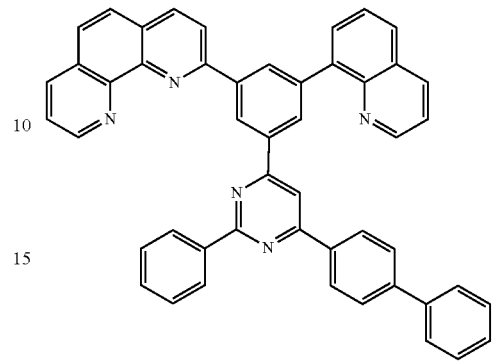

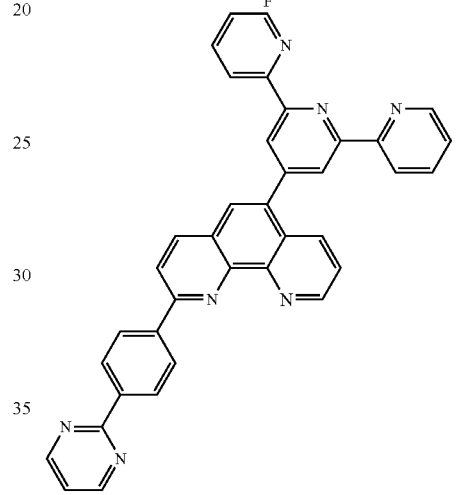
F

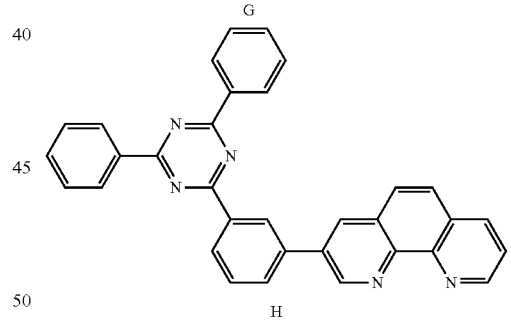
G

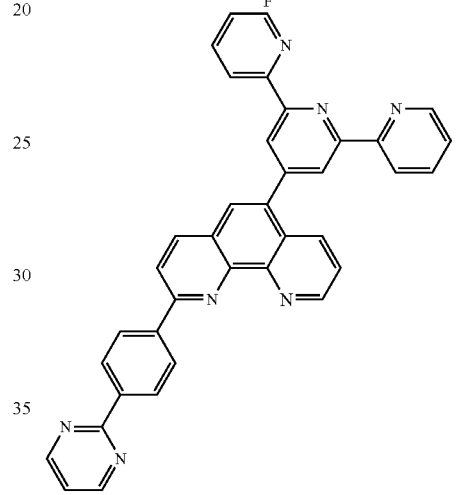
H

Referring to Table 2, the organic light-emitting devices of Examples 1 to 5 were found to have significant and unexpectedly excellent external quantum efficiency, low driving voltage, or long lifespan characteristics, as compared with the organic light-emitting devices of Comparative Examples 1 to 9.

As apparent from the foregoing description, an organic light-emitting device including the heterocyclic compound constructed according to the principles and exemplary embodiments of the invention have excellent driving voltage, external quantum efficiency, and long lifespan.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An organic light-emitting device comprising:
a first electrode;
a second electrode facing the first electrode;
an organic layer disposed between the first electrode and the second electrode and comprising an emission layer; and
at least one of heterocyclic compounds represented by Formulae 1-1 to 1-3:

Formula 1-1

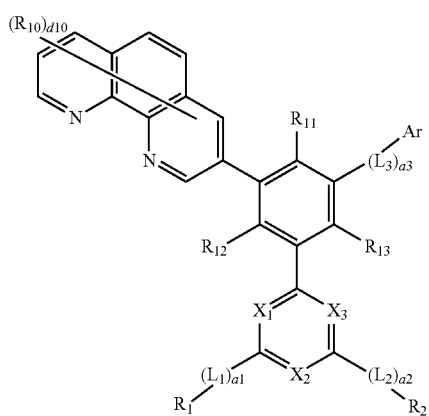

Formula 1-2

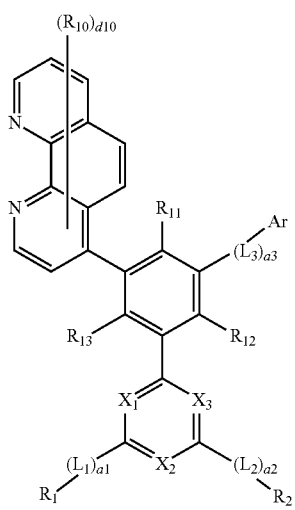

Formula 1-3

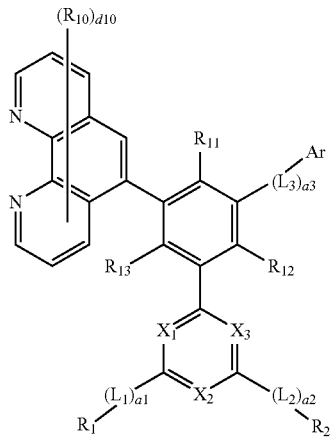

wherein, in Formulae 1-1 to 1-3,
ring Ar is a π electron-depleted nitrogen-containing C1-C60 cyclic group unsubstituted or substituted with at least one R10a;
X1 is C(R21) or N;
X2 is C(R22) or N;
X3 is C(R23) or N;
L1 to L3 are each, independently from one another, a single bond, a C5-C30 carbocyclic group unsubstituted or substituted with at least one R20a, or a C2-C30 heterocyclic group unsubstituted or substituted with at least one R20a;
a1 to a3 are each, independently from one another, an integer from 1 to 5;
R1 and R2 are each, independently from one another, hydrogen, deuterium, —F, —Cl, —Br, —I, a hydroxyl group, a cyano group, a nitro group, an amidino group, a hydrazine group, a hydrazone group, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C2-C10 heterocycloalkyl group, a substituted or unsubstituted C3-C10 cycloalkenyl group, a substituted or unsubstituted C2-C10 heterocycloalkenyl group, a substituted or unsubstituted C6-C60 aryl group, a substituted or unsubstituted C6-C60 aryloxy group, a substituted or unsubstituted C6-C60 arylthio group, a substituted or unsubstituted C1-C60 heteroaryl group, a substituted or unsubstituted monovalent non-aromatic fused polycyclic group, a substituted or unsubstituted monovalent non-aromatic fused heteropolycyclic group, a π electron-rich C3-C60 cyclic group unsubstituted or substituted with at least one R30a, —Si(Q1)(Q2)(Q3), —N(Q1)(Q2), —B(Q1)(Q2), —C(=O)(Q1), —S(=O)2(Q1), or —P(=O)(Q1)(Q2);
R10 to R13, R10a, R20a, R30a, and R21 to R23 are each, independently from one another, hydrogen, deuterium, —F, —Cl, —Br, —I, a hydroxyl group, a cyano group, a nitro group, an amidino group, a hydrazine group, a hydrazone group, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C2-C10 heterocycloalkyl group, a substituted or unsubstituted C3-C10 cycloalkenyl group, a substituted or unsubstituted C2-C10 heterocycloalkenyl group, a substituted or unsubstituted C6-C60 aryl group, a substituted or unsubstituted C6-C60 aryloxy group, a substituted or unsubstituted C6-C60 arylthio group, a substituted or unsubstituted C1-C60 heteroaryl group, a substituted or unsubstituted monovalent non-aromatic fused polycyclic group, a substituted or unsubstituted monovalent non-aromatic fused heteropolycyclic group, —Si(Q1)(Q2)(Q3), —N(Q1)(Q2), —B(Q1)(Q2), —C(=O)(Q1), —S(=O)2(Q1), or —P(=O)(Q1)(Q2);

d10 is an integer from 0 to 7; and a substituent of the substituted C1-C60 alkyl group, the substituted C2-C60 alkenyl group, the substituted C2-C60 alkynyl group, the substituted C1-C60 alkoxy group, the substituted C3-C10 cycloalkyl group, the substituted C1-C10 heterocycloalkyl group, the substituted C3-C10 cycloalkenyl group, the substituted C1-C10 heterocycloalkenyl group, the substituted C6-C60 aryl group, the substituted C6-C60 aryloxy group, the substituted C6-C60 arylthio group, the substituted C1-C60 heteroaryl group, the substituted monovalent non-aromatic fused polycyclic group, and the substituted monovalent non-aromatic fused heteropolycyclic group is:

deuterium, —F, —Cl, —Br, —I, a hydroxyl group, a cyano group, a nitro group, an amidino group, a hydrazine group, a hydrazone group, a C1-C60 alkyl group, a C2-C60 alkenyl group, a C2-C60 alkynyl group, or a C1-C60 alkoxy group;

a C1-C60 alkyl group, a C2-C60 alkenyl group, a C2-C60 alkynyl group, or a C1-C60 alkoxy group, each substituted with at least one of deuterium, —F, —Cl, —Br, —I, a hydroxyl group, a cyano group, a nitro group, an amidino group, a hydrazine group, a hydrazone group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic fused polycyclic group, a monovalent non-aromatic fused heteropolycyclic group, —Si(Q11)(Q12)(Q13), —N(Q11)(Q12), —B(Q11)(Q12), —C(=O)(Q11), —S(=O)2(Q11), and —P(=O)(Q11)(Q12);

a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a C1-C60 alkyl group, a C2-C60 alkenyl group, a C2-C60 alkynyl group, a C1-C60 alkoxy group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic fused polycyclic group, a monovalent non-aromatic fused heteropolycyclic group, —Si(Q21)(Q22)(Q23), —N(Q21)(Q22), —B(Q21)(Q22), —C(=O)(Q21), —S(=O)2(Q21), and —P(=O)(Q21)(Q22); or —Si(Q31)(Q32)(Q33), —N(Q31)(Q32), —B(Q31)(Q32), —C(=O)(Q31), —S(=O)2(Q31), or —P(=O)(Q31)(Q32), wherein Q1 to Q3, Q11 to Q13, Q21 to Q23, and Q31 to Q33 are each, independently from one another: hydrogen; deuterium; —F; —Cl; —Br; —I; a hydroxyl group; a cyano group; a nitro group; an amidino group; a hydrazine group; a hydrazone group; a C1-C60 alkyl group; a C2-C60 alkenyl group; a C2-C60 alkynyl group; a C1-C60 alkoxy group; a C3-C10 cycloalkyl group; a C1-C10 heterocycloalkyl group; a C3-C10 cycloalkenyl group; a C1-C10 heterocycloalkenyl group; a C6-C60 aryl group; a C1-C60 heteroaryl group; a monovalent non-aromatic fused polycyclic group; a monovalent non-aromatic fused heteropolycyclic group; a C1-C60 alkyl group substituted with at least one of deuterium, —F, and a cyano group; a C6-C60 aryl group substituted with at least one of deuterium, —F, and a cyano group; a biphenyl group; or a terphenyl group, wherein Formulae 1-1 to 1-3 each satisfy at least one of Conditions 1 to 3:

Condition 1 wherein R1 is a π electron-rich C3-C60 cyclic group unsubstituted or substituted with at least one R30a, Condition 2 wherein R2 is a π electron-rich C3-C60 cyclic group unsubstituted or substituted with at least one R30a, and Condition 3 wherein R1 and R2 are each independently a π electron-rich C3-C60 cyclic group unsubstituted or substituted with at least one R30a;

wherein the π electron-rich C3-C60 cyclic group is a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonapthothiophene group, (an indolo)phenanthrene group, a (benzofurano)phenanthrene group, or a (benzothieno)phenanthrene group, wherein the π electron-depleted nitrogen-containing C1-C60 cyclic group is a) a first ring, b) a fused ring in which at least two first rings are fused, or c) a fused ring in which at least one first ring and at least one second ring are fused;

the π electron-rich C3-C60 cyclic group is a) a second ring or b) a fused ring in which at least two second rings are fused;

the first ring is an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, a tetrazine group, a pentazine group, a hexazine group, or a thiadiazole group, and the second ring is a benzene group, a cyclopentadiene group, a pyrrole group, a furan group, a thiophene group, or a silole group.

2. The light-emitting device of claim 1, wherein:
the first electrode is an anode,
the second electrode is a cathode, and
the organic layer comprises the at least one of the heterocyclic compounds represented by Formulae 1-1 to 1-3, and
the organic layer further comprises a hole transport region disposed between the first electrode and the emission layer and an electron transport region disposed between the emission layer and the second electrode.

3. The light-emitting device of claim 1, wherein the hole transport region comprises a hole injection layer, a hole transport layer, an emission auxiliary layer, an electron blocking layer, or any combination thereof,
the electron transport region comprises a hole blocking layer, an electron transport layer, an electron injection layer, or any combination thereof, and
the electron transport region comprises the at least one of the heterocyclic compounds.

4. The organic light-emitting device of claim 3, wherein the hole transport region comprises a compound represented by Formula 201 or Formula 202:

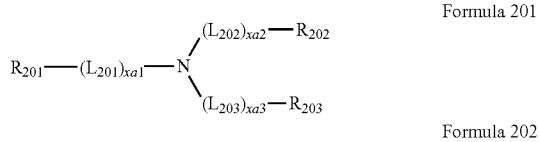

Formula 201

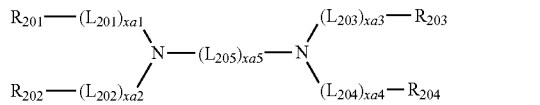

Formula 202 wherein, in Formulae 201 and 202, $L_{201}$ to $L_{204}$ are each, independently from one another, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic fused polycyclic group, or a substituted or unsubstituted divalent non-aromatic fused heteropolycyclic group;

$L_{205}$ is *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic fused polycyclic group, or a substituted or unsubstituted divalent non-aromatic fused heteropolycyclic group;

xa1 to xa4 are each, independently from one another, an integer from 0 to 3;

xa5 is an integer from 1 to 10; and $R_{201}$ to $R_{204}$ and $Q_{201}$ are each, independently from one another, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, or a substituted or unsubstituted monovalent non-aromatic fused heteropolycyclic group.

5. The organic light-emitting device of claim 3, wherein the electron transport region comprises the electron injection layer; and the electron injection layer comprises an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

6. The organic light-emitting device of claim 3, wherein the emission layer comprises an anthracene-based compound.

7. An organic light-emitting device comprising:
a first electrode;
a second electrode facing the first electrode;
m emission units disposed between the first electrode and the second electrode, each comprising at least one emission layer; and
m−1 charge generating layers, each between two adjacent emission units from among the m emission units,
wherein m is an integer of 2 or greater, and
at least one of the m−1 charge generating layers comprises at least one of the heterocyclic compounds represented by Formulae 1-1 to 1-3:

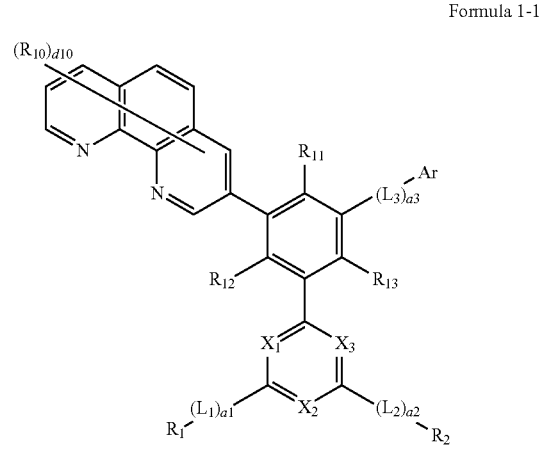

Formula 1-1

-continued

Formula 1-2

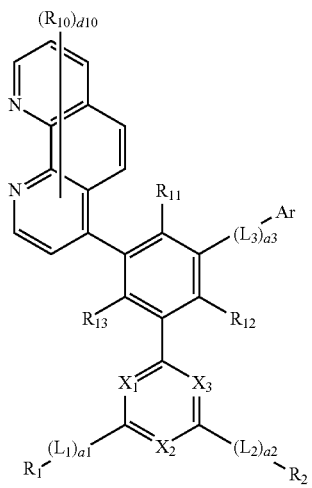

Formula 1-3

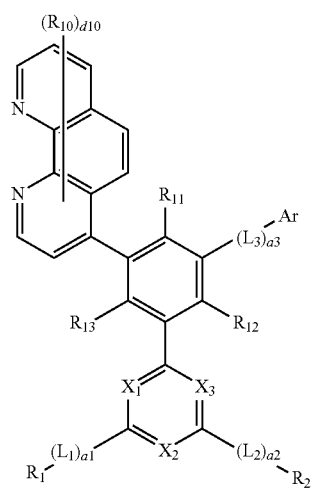

wherein, in Formulae 1-1 to 1-3,
ring Ar is a π electron-depleted nitrogen-comprising $C_1$-$C_{60}$ cyclic group unsubstituted or substituted with at least one $R_{10a}$;
$X_1$ is $C(R_{21})$ or N;
$X_2$ is $C(R_{22})$ or N;
$X_3$ is $C(R_{23})$ or N;
$L_1$ to $L_3$ are each, independently from one another, a single bond, a $C_5$-$C_{30}$ carbocyclic group unsubstituted or substituted with at least one $R_{20a}$, or a $C_2$-$C_{30}$ heterocyclic group unsubstituted or substituted with at least one $R_{20a}$;
a1 to a3 are each, independently from one another, an integer from 1 to 5;
$R_1$ and $R_2$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, a π electron-rich $C_3$-$C_{60}$ cyclic group unsubstituted or substituted with at least one $R_{30a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);
$R_{10}$ to $R_{13}$, $R_{10a}$, $R_{20a}$, $R_{30a}$, and $R_{21}$ to $R_{23}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);
d10 is an integer from 0 to 7; and
a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group is:
deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, a hydroxyl group, a cyano group, a nitro group, an amidino group, a hydrazine group, a hydrazone group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic fused polycyclic group; a monovalent non-aromatic fused heteropolycyclic group; a $C_1$-$C_{60}$ alkyl group substituted with at least one of deuterium, —F, and a cyano group; a $C_6$-$C_{60}$ aryl group substituted with at least one of deuterium, —F, and a cyano group; a biphenyl group; or a terphenyl group.

8. A heterocyclic compound represented by one of Formulae 1-1 to 1-3:

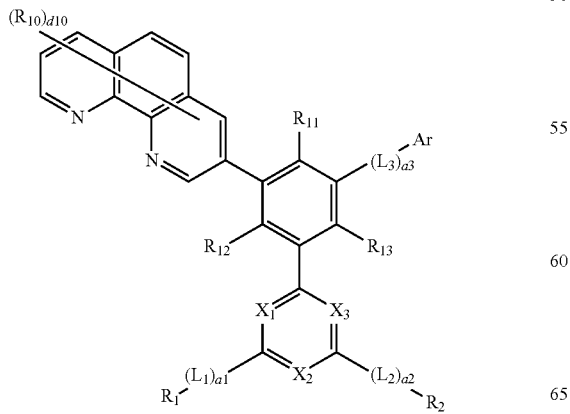

Formula 1-1

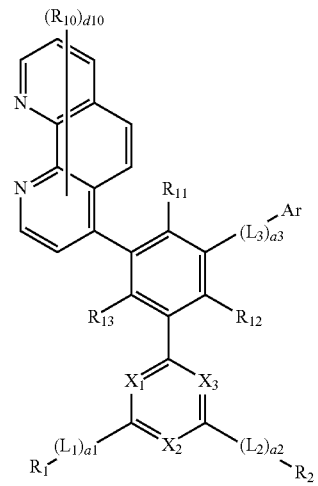

Formula 1-2

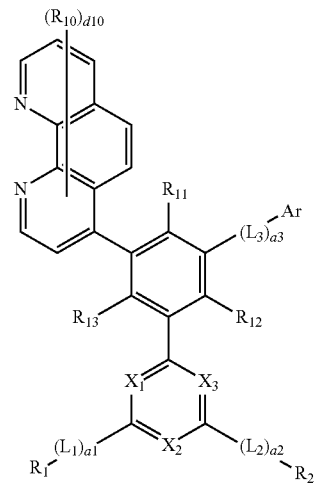

Formula 1-3 wherein, in Formulae 1-1 to 1-3, ring Ar is a π electron-depleted nitrogen-containing $C_1$-$C_{60}$ cyclic group unsubstituted or substituted with at least one $R_{10a}$;

$X_1$ is C($R_{21}$) or N;

$X_2$ is C($R_{22}$) or N;

$X_3$ is C($R_{23}$) or N;

$L_1$ to $L_3$ are each, independently from one another, a single bond, a $C_5$-$C_{30}$ carbocyclic group unsubstituted or substituted with at least one $R_{20a}$, or a $C_2$-$C_{30}$ heterocyclic group unsubstituted or substituted with at least one $R_{20a}$;

a1 to a3 are each, independently from one another, an integer from 1 to 5;

$R_1$ and $R_2$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, a π electron-rich $C_3$-$C_{60}$ cyclic group unsubstituted or substituted with at least one $R_{30a}$, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);

$R_{10}$ to $R_{13}$, $R_{10a}$, $R_{20a}$, $R_{30a}$, and $R_{21}$ to $R_{23}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$);

d10 is an integer from 0 to 7; and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group is:

deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of deuterium, —F, —Cl, —Br, —I, a hydroxyl group, a cyano group, a nitro group, an amidino group, a hydrazine group, a hydrazone group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each, independently from one another: hydrogen; deuterium; —F; —Cl; —Br; —I; a hydroxyl group; a cyano group; a nitro group; an amidino group; a hydrazine group; a hydrazone group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_1$-$C_{60}$ heteroaryl group; a monovalent non-aromatic fused polycyclic group; a monovalent non-aromatic fused heteropolycyclic group; a $C_1$-$C_{60}$ alkyl group substituted with at least one of deuterium, —F, and a cyano group; a $C_6$-$C_{60}$ aryl group substituted with at least one of deuterium, —F, and a cyano group; a biphenyl group; or a terphenyl group, wherein Formulae 1-1 to 1-3 each satisfy at least one of Conditions 1 to 3:

Condition 1 wherein $R_1$ is a π electron-rich $C_3$-$C_{60}$ cyclic group unsubstituted or substituted with at least one $R_{30a}$, Condition 2 wherein $R_2$ is a π electron-rich $C_3$-$C_{60}$ cyclic group unsubstituted or substituted with at least one $R_{30a}$, and Condition 3 wherein $R_1$ and $R_2$ are each independently a π electron-rich $C_3$-$C_{60}$ cyclic group unsubstituted or substituted with at least one $R_{30a}$;

wherein the π electron-rich $C_3$-$C_{60}$ cyclic group is a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonapthothiophene group, (an indolo)phenanthrene group, a (benzofurano)phenanthrene group, or a (benzothieno)phenanthrene group, wherein the π electron-depleted nitrogen-containing C1-C60 cyclic group is a) a first ring, b) a fused ring in which at least two first rings are fused, or c) a fused ring in which at least one first ring and at least one second ring are fused;

the π electron-rich C3-C60 cyclic group is a) a second ring or b) a fused ring in which at least two second rings are fused;

the first ring is an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, a tetrazine group, a pentazine group, a hexazine group, or a thiadiazole group, and the second ring is a benzene group, a cyclopentadiene group, a pyrrole group, a furan group, a thiophene group, or a silole group.

9. A heterocyclic compound represented by one of Formulae 1-1 to 1-3:

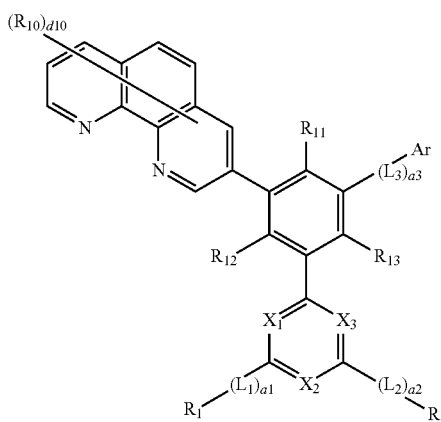

Formula 1-1

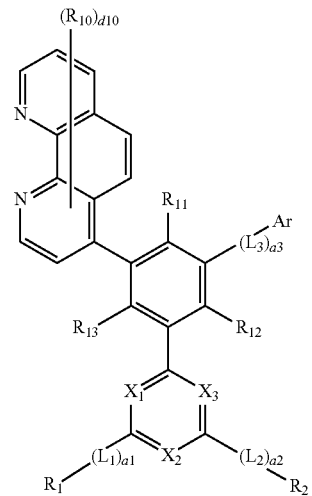

Formula 1-2

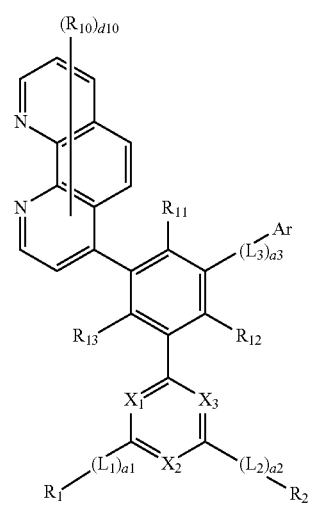

Formula 1-3 wherein, in Formulae 1-1 to 1-3, ring Ar is a π electron-depleted nitrogen-containing C1-C60 cyclic group unsubstituted or substituted with at least one R10a;

X1 is C(R21) or N;

X2 is C(R22) or N;

X3 is C(R23) or N;

L1 to L3 are each, independently from one another, a single bond, a C5-C30 carbocyclic group unsubstituted or substituted with at least one R20a, or a C2-C30 heterocyclic group unsubstituted or substituted with at least one R20a;

a1 to a3 are each, independently from one another, an integer from 1 to 5;

R1 and R2 are each, independently from one another, hydrogen, deuterium, —F, —Cl, —Br, —I, a hydroxyl group, a cyano group, a nitro group, an amidino group, a hydrazine group, a hydrazone group, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C2-C10 heterocycloalkyl group, a substituted or unsubstituted C3-C10 cycloalkenyl group, a substituted or unsubstituted C2-C10 heterocycloalkenyl group, a substituted or unsubstituted C6-C60 aryl group, a substituted or unsubstituted C6-C60 aryloxy group, a substituted or unsubstituted C6-C60 arylthio group, a substituted or unsubstituted C1-C60 heteroaryl group, a substituted or unsubstituted monovalent non-aromatic fused polycyclic group, a substituted or unsubstituted monovalent non-aromatic fused heteropolycyclic group, a π electron-rich C3-C60 cyclic group unsubstituted or substituted with at least one R30a, —Si(Q1)(Q2)(Q3), —N(Q1)(Q2), —B(Q1)(Q2), —C(=O)(Q1), —S(=O)2(Q1), or —P(=O)(Q1)(Q2);

R10 to R13, R10a, R20a, R30a, and R21 to R23 are each, independently from one another, hydrogen, deuterium, —F, —Cl, —Br, —I, a hydroxyl group, a cyano group, a nitro group, an amidino group, a hydrazine group, a hydrazone group, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C2-C10 heterocycloalkyl group, a substituted or unsubstituted C3-C10 cycloalkenyl group, a substituted or unsubstituted C2-C10 heterocycloalkenyl group, a substituted or unsubstituted C6-C60 aryl group, a substituted or unsubstituted C6-C60 aryloxy group, a substituted or unsubstituted C6-C60 arylthio group, a substituted or unsubstituted C1-C60 heteroaryl group, a substituted or unsubstituted monovalent non-aromatic fused polycyclic group, a substituted or unsubstituted monovalent non-aromatic fused heteropolycyclic group, —Si(Q1)(Q2)(Q3), —N(Q1)(Q2), —B(Q1)(Q2), —C(=O)(Q1), —S(=O)2(Q1), or —P(=O)(Q1)(Q2);

d10 is an integer from 0 to 7; and a substituent of the substituted C1-C60 alkyl group, the substituted C2-C60 alkenyl group, the substituted C2-C60 alkynyl group, the substituted C1-C60 alkoxy group, the substituted C3-C10 cycloalkyl group, the substituted C1-C10 heterocycloalkyl group, the substituted C3-C10 cycloalkenyl group, the substituted C1-C10 heterocycloalkenyl group, the substituted C6-C60 aryl group, the substituted C6-C60 aryloxy group, the substituted C6-C60 arylthio group, the substituted C1-C60 heteroaryl group, the substituted monovalent non-aromatic fused polycyclic group, and the substituted monovalent non-aromatic fused heteropolycyclic group is:

deuterium, —F, —Cl, —Br, —I, a hydroxyl group, a cyano group, a nitro group, an amidino group, a hydrazine group, a hydrazone group, a C1-C60 alkyl group, a C2-C60 alkenyl group, a C2-C60 alkynyl group, or a C1-C60 alkoxy group;

a C1-C60 alkyl group, a C2-C60 alkenyl group, a C2-C60 alkynyl group, or a C1-C60 alkoxy group, each substituted with at least one of deuterium, —F, —Cl, —Br, —I, a hydroxyl group, a cyano group, a nitro group, an amidino group, a hydrazine group, a hydrazone group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic fused polycyclic group, a monovalent non-aromatic fused heteropolycyclic group, —Si(Q11)(Q12)(Q13), —N(Q11)(Q12), —B(Q11)(Q12), —C(=O)(Q11), —S(=O)2(Q11), and —P(=O)(Q11)(Q12);

a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic fused polycyclic group, or a monovalent non-aromatic fused heteropolycyclic group, each unsubstituted or substituted with at least one of deuterium, —F, —Cl, —Br, —I, a hydroxyl group, a cyano group, a nitro group, an amidino group, a hydrazine group, a hydrazone group, a C1-C60 alkyl group, a C2-C60 alkenyl group, a C2-C60 alkynyl group, a C1-C60 alkoxy group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic fused polycyclic group, a monovalent non-aromatic fused heteropolycyclic group, —Si(Q21)(Q22)(Q23), —N(Q21)(Q22), —B(Q21)(Q22), —C(=O)(Q21), —S(=O)2(Q21), and —P(=O)(Q21)(Q22); or —Si(Q31)(Q32)(Q33), —N(Q31)(Q32), —B(Q31)(Q32), —C(=O)(Q31), —S(=O)2(Q31), or —P(=O)(Q31)(Q32), wherein Q1 to Q3, Q11 to Q13, Q21 to Q23, and Q31 to Q33 are each, independently from one another: hydrogen; deuterium; —F; —Cl; —Br; —I; a hydroxyl group; a cyano group; a nitro group; an amidino group; a hydrazine group; a hydrazone group; a C1-C60 alkyl group; a C2-C60 alkenyl group; a C2-C60 alkynyl group; a C1-C60 alkoxy group; a C3-C10 cycloalkyl group; a C1-C10 heterocycloalkyl group; a C3-C10 cycloalkenyl group; a C1-C10 heterocycloalkenyl group; a C6-C60 aryl group; a C1-C60 heteroaryl group; a monovalent non-aromatic fused polycyclic group; a monovalent non-aromatic fused heteropolycyclic group; a C1-C60 alkyl group substituted with at least one of deuterium, —F, and a cyano group; a C6-C60 aryl group substituted with at least one of deuterium, —F, and a cyano group; a biphenyl group; or a terphenyl group, wherein Formulae 1-1 to 1-3 each satisfy at least one of Conditions 1 to 3:

Condition 1 wherein R1 is a π electron-rich C3-C60 cyclic group unsubstituted or substituted with at least one R30a, Condition 2 wherein R2 is a π electron-rich C3-C60 cyclic group unsubstituted or substituted with at least one R30a, and Condition 3 wherein R1 and R2 are each independently a π electron-rich C3-C60 cyclic group unsubstituted or substituted with at least one R30a;

wherein the π electron-rich C3-C60 cyclic group is a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonapthothiophene group, (an indolo)phenanthrene group, a (benzofurano)phenanthrene group, or a (benzothieno)phenanthrene group, wherein the π electron-depleted nitrogen-containing $C_1$-$C_{60}$ cyclic group is one of an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, an acridine group, a pyridopyrazine group, or one of the groups represented by Formulae 2-1 to 2-17:

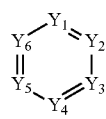

2-1

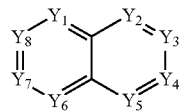

2-2

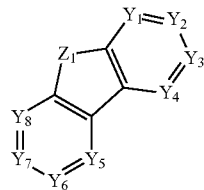

2-3

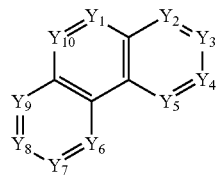

2-4

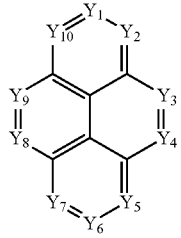

2-5

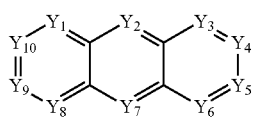

2-6

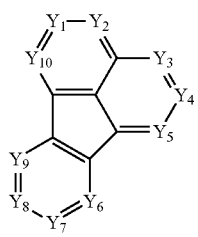

2-7

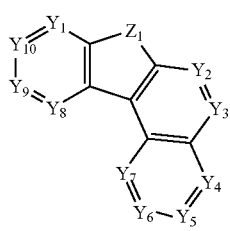

2-8

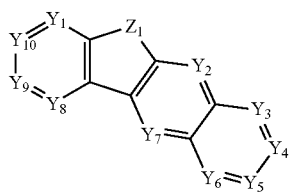

2-9

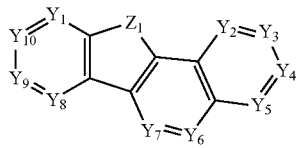

2-10

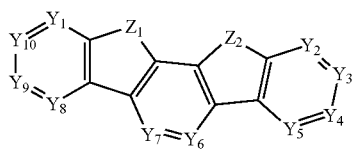

2-11

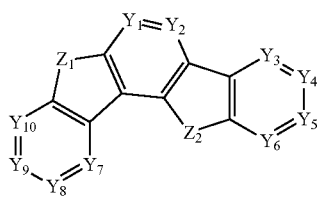

2-12

-continued 2-13
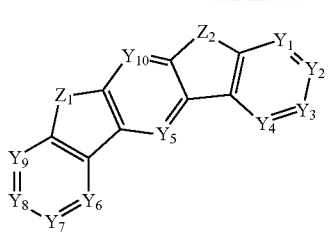

2-14
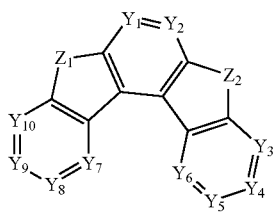

2-15
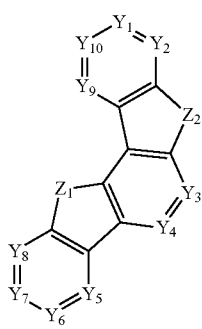

2-16
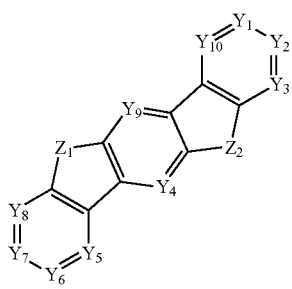

2-17
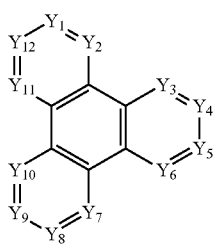

wherein, in Formulae 2-1 to 2-17,
$Z_1$ is O, S, $N(R_{1a})$, $C(R_{1a})(R_{1b})$, or $Si(R_{1a})(R_{1b})$,
$Z_2$ is O, S, $N(R_{2a})$, $C(R_{2a})(R_{2b})$, or $Si(R_{2a})(R_{2b})$,
$Y_1$ is $C(R_{31})$ or N,
$Y_2$ is $C(R_{32})$ or N;
$Y_3$ is $C(R_{33})$ or N,
$Y_4$ is $C(R_{34})$ or N,
$Y_5$ is $C(R_{35})$ or N,
$Y_6$ is $C(R_{36})$ or N,
$Y_7$ is $C(R_{37})$ or N,
$Y_8$ is $C(R_{38})$ or N,
$Y_9$ is $C(R_{39})$ or N,
$Y_{10}$ is $C(R_{40})$ or N,
$Y_{11}$ is $C(R_{41})$ or N,
$Y_{12}$ is $C(R_{42})$ or N,
in Formula 2-1, at least one of $Y_1$ to $Y_6$ is N,
in Formulae 2-2 and 2-3, at least one of $Y_1$ to $Y_8$ is N,
in Formulae 2-4 and 2-16, at least one of $Y_1$ to $Y_{10}$ is N,
in Formula 2-17, at least one of $Y_1$ to $Y_{12}$ is N, and
$R_{1a}$, $R_{1b}$, $R_{2a}$, $R_{2b}$, and $R_{31}$ to $R_{42}$ are each, independently from one another, have the same meaning as $R_{10a}$ in claim 8.

10. The heterocyclic compound of claim 8, wherein:
$X_1$ is $C(R_{21})$, $X_2$ is $C(R_{22})$, and $X_3$ is N;
$X_1$ is $C(R_{21})$, $X_3$ is $C(R_{23})$, and $X_2$ is N;
$X_2$ is $C(R_{22})$, $X_3$ is $C(R_{23})$, and $X_1$ is N;
$X_1$ and $X_2$ are each N, and $X_3$ is $C(R_{23})$;
$X_1$ and $X_3$ are each N, and $X_2$ is $C(R_{22})$;
$X_2$ and $X_3$ are each N, and $X_1$ is $C(R_{21})$; or
$X_1$, $X_2$, and $X_3$ are each N;
wherein $R_{21}$ to $R_{23}$ are each, independently from one another, have the same meaning as in claim 8.

11. The heterocyclic compound of claim 8, wherein $L_1$ to $L_3$ are each, independently from one another:
a single bond; or
a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, or a 5,6,7,8-tetrahydroquinoline group, each unsubstituted or substituted with at least one $R_{20a}$ wherein $R_{20a}$ has the same meaning as in claim 8.

12. The heterocyclic compound of claim 8, wherein $L_1$ to $L_3$ are each, independently from one another:
a single bond; or
a benzene group, a naphthalene group, a carbazole group, an anthracene group, a phenanthrene group, a triphenylene group, a pyrene group, a fluorene group, a dibenzothiophene group, or a dibenzofuran group, each unsubstituted or substituted with at least one $R_{20a}$ wherein $R_{20a}$ has the same meaning as in claim 8.

13. The heterocyclic compound of claim 8, wherein $R_{10}$ to $R_{13}$, $R_{10a}$, $R_{20a}$, $R_{30a}$, and $R_{21}$ to $R_{23}$ are each, independently from one another:
 hydrogen, deuterium, —F, —Cl, —Br, —I, a hydroxyl group, a cyano group, a nitro group, an amidino group, a hydrazine group, a hydrazone group, a $C_1$-$C_{10}$ alkyl group, a $C_2$-$C_{10}$ alkenyl group, a $C_2$-$C_{10}$ alkynyl group, or a $C_1$-$C_{10}$ alkoxy group;
 a $C_1$-$C_{10}$ alkyl group, a $C_2$-$C_{10}$ alkenyl group, a $C_2$-$C_{10}$ alkynyl group, or a $C_1$-$C_{10}$ alkoxy group, each optionally substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a naphthyl group, a pyridinyl group, and a pyrimidinyl group;
 a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, an azafluorenyl group, or an azadibenzosilolyl group, each optionally substituted with at least one of deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a $C_1$-$C_{10}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —$Si(Q_{31})(Q_{32})(Q_{33})$, —$N(Q_{31})(Q_{32})$, —$B(Q_{31})(Q_{32})$, —$P(Q_{31})(Q_{32})$, —$C(=O)(Q_{31})$, —$S(=O)_2(Q_{31})$, and —$P(=O)(Q_{31})(Q_{32})$; or
 —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$,
 wherein $Q_1$ to $Q_3$ and $Q_{31}$ to $Q_{33}$ are each, independently from one another:
 —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or
 an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, a pyridinyl group, a pyrimidinyl group, a pyridazinyl group, a pyrazinyl group, or a triazinyl group, each unsubstituted or substituted with at least one of deuterium, a $C_1$-$C_{10}$ alkyl group, a phenyl group, a biphenyl group, a pyridinyl group, a pyrimidinyl group, a pyridazinyl group, a pyrazinyl group, and a triazinyl group.

14. The heterocyclic compound of claim 8, wherein $R_{10}$ to $R_{13}$ are each, independently from one another:
 hydrogen, deuterium, —F, —Cl, —Br, —I, a hydroxyl group, a cyano group, a nitro group, an amidino group, a hydrazine group, a hydrazone group, a $C_1$-$C_{10}$ alkyl group, a $C_2$-$C_{10}$ alkenyl group, a $C_2$-$C_{10}$ alkynyl group, or a $C_1$-$C_{10}$ alkoxy group;
 a $C_1$-$C_{10}$ alkyl group, a $C_2$-$C_{10}$ alkenyl group, a $C_2$-$C_{10}$ alkynyl group, or a $C_1$-$C_{10}$ alkoxy group, each substituted with at least one of deuterium, —F, —Cl, —Br, —I, —$CD_3$, —$CD_2H$, —$CDH_2$, a hydroxyl group, a cyano group, a nitro group, an amidino group, a hydrazine group, a hydrazone group, a $C_1$-$C_{10}$ alkyl group, a phenyl group, a biphenyl group, and a naphthyl group; or
 —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$,
 wherein $Q_1$ to $Q_3$ are each, independently from one another:
 hydrogen; deuterium; —F; —Cl; —Br; —I; a hydroxyl group; a cyano group; a nitro group; an amidino group; a hydrazine group; a hydrazone group; a $C_1$-$C_{20}$ alkyl group; a $C_2$-$C_{20}$ alkenyl group; a $C_2$-$C_{20}$ alkynyl group; a $C_1$-$C_{20}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{30}$ aryl group; a $C_1$-$C_{30}$ heteroaryl group; a monovalent non-aromatic fused polycyclic group; a monovalent non-aromatic fused heteropolycyclic group; a $C_1$-$C_{20}$ alkyl group substituted with at least one of deuterium, —F, and a cyano group; a $C_6$-$C_{30}$ aryl group substituted with at least one of deuterium, —F, and a cyano group; a biphenyl group; or a terphenyl group.

15. The heterocyclic compound of claim 8, wherein $R_1$ and $R_2$ are each, independently from one another, hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a π electron-rich $C_3$-$C_{60}$ cyclic group unsubstituted or substituted with at least one $R_{30a}$ wherein $R_{30a}$ has the same meaning as in claim 8.

16. The heterocyclic compound of claim 8, wherein, in Formulae 1-1 to 1-3, a group represented by *-$(L_1)_{a1}$-$R_1$ and a group represented by *-$(L_2)_{a2}$-$R_2$ satisfy at least one of Conditions 1a to 3a:

Condition 1a wherein the group represented by *-$(L_1)_{a1}$-$R_1$ is: a π electron-rich $C_3$-$C_{60}$ cyclic group unsubstituted or substituted with at least one of $R_{30a}$ or one of the groups represented by Formulae 3-1 to 3-10, Condition 2a wherein the group represented by *-$(L_2)_{a2}$-$R_2$ is: a π electron-rich $C_3$-$C_{60}$ cyclic group unsubstituted or substituted with at least one $R_{30a}$ or one of the groups represented by Formulae 3-1 to 3-10, and Condition 3a wherein the group represented by *-$(L_1)_{a1}$-$R_1$ and the group represented by *-$(L_2)_{a2}$-$R_2$ are each, independently from one another: a π electron-rich $C_3$-$C_{60}$ cyclic group unsubstituted or substituted with at least one $R_{30a}$ or one of the groups represented by Formulae 3-1 to 3-10, 3-1

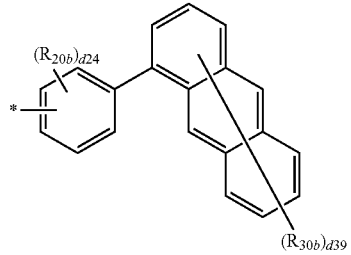

3-2

3-3

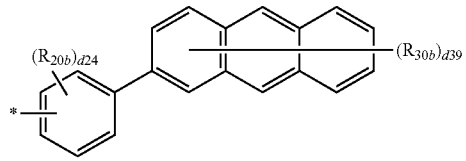

3-4

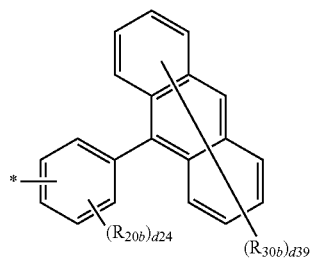

3-5

3-6

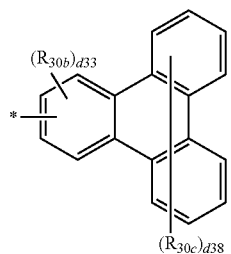

3-7

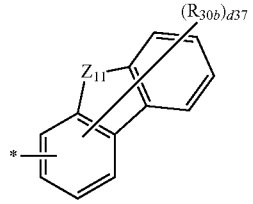

3-8

3-9

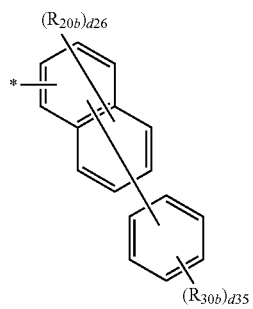

-continued 3-10

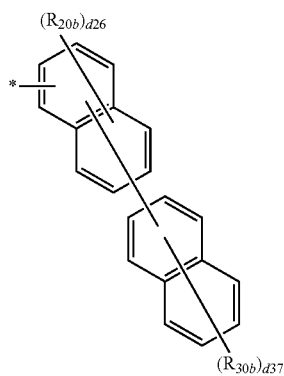

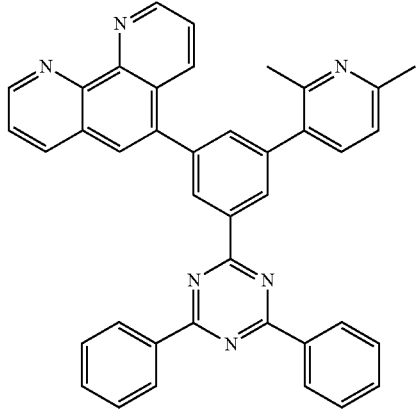
2 wherein, in Formulae 3-1 to 3-10, $Z_{11}$ is O, S, $N(R_{11a})$, $C(R_{11a})(R_{11b})$, or $Si(R_{11a})(R_{11b})$, $R_{20b}$ has the same meaning of $R_{20a}$ in claim 8, $R_{30b}$ and $R_{30c}$ are each, independently from one another, have the same meaning of $R_{30a}$ in claim 8, d24 is an integer from 0 to 4, d26 is an integer from 0 to 6, d33 is an integer from 0 to 3, d35 is an integer from 0 to 5, d37 is an integer from 0 to 7, d38 is an integer from 0 to 8,

*indicates a binding site to an adjacent atom, and $R_{11a}$ and $R_{11b}$ are each, independently from one another, have the meaning of $R_{30a}$ in claim 8.

17. The heterocyclic compound of claim 8, wherein the heterocyclic compound is one of Compounds 1 to 32:

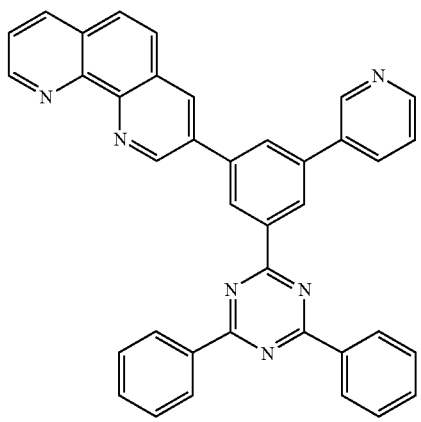
3

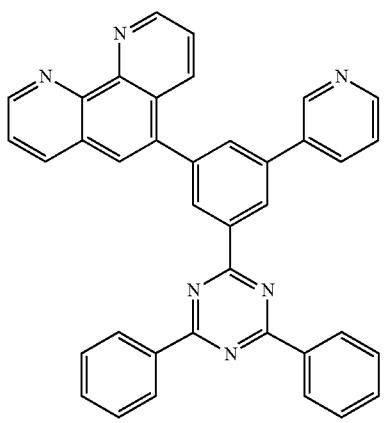
1

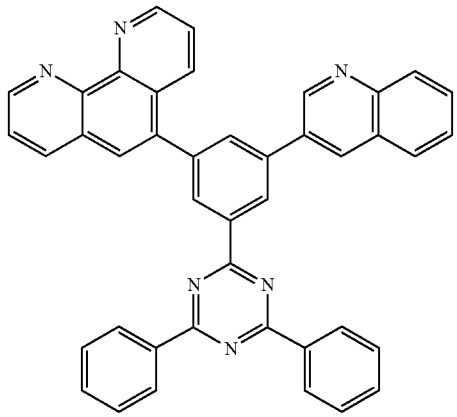
4

-continued
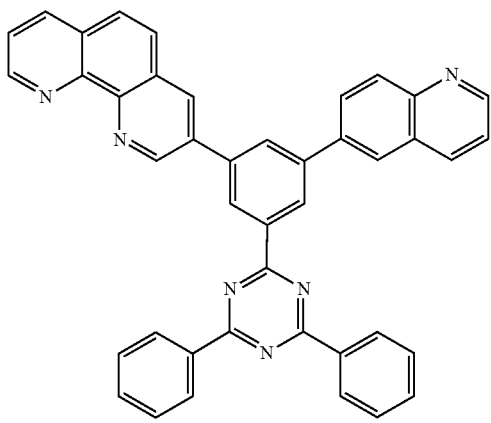
5
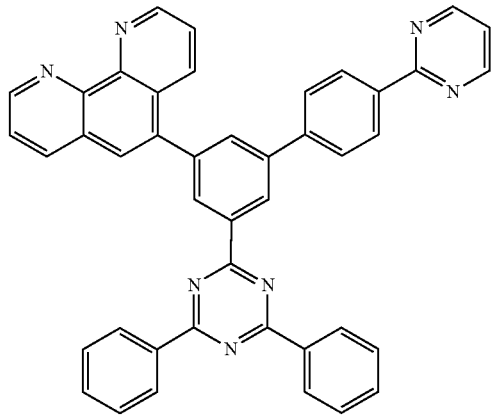
8
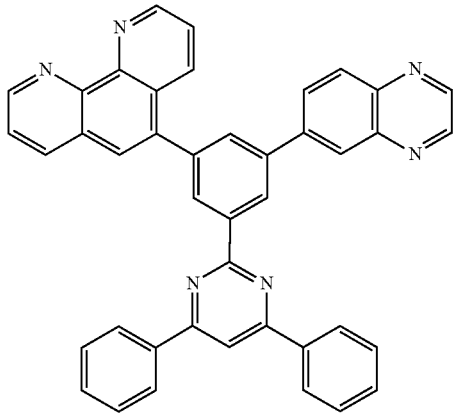
6
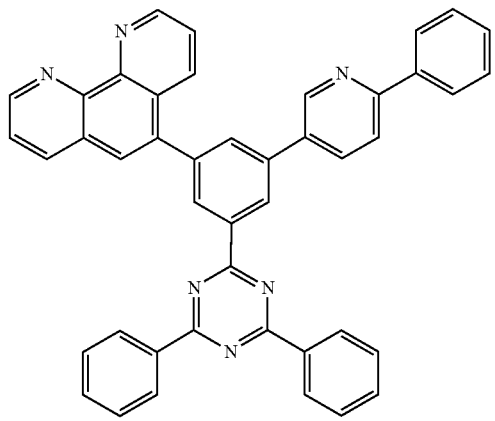
9
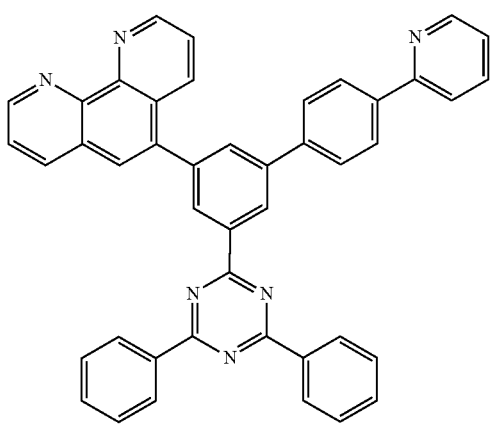
7
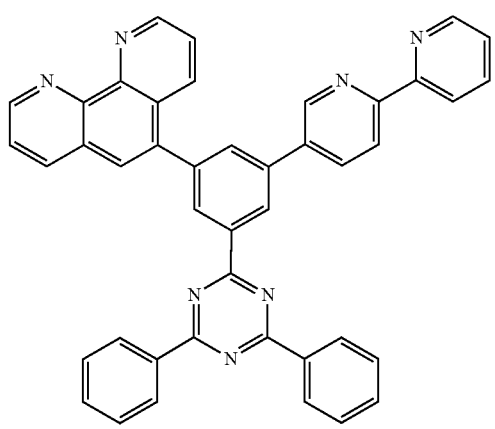
10

187
-continued
11
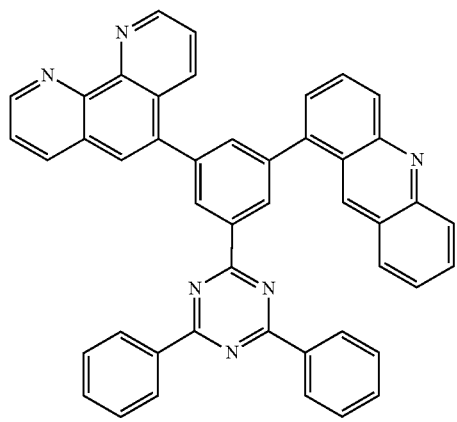
12
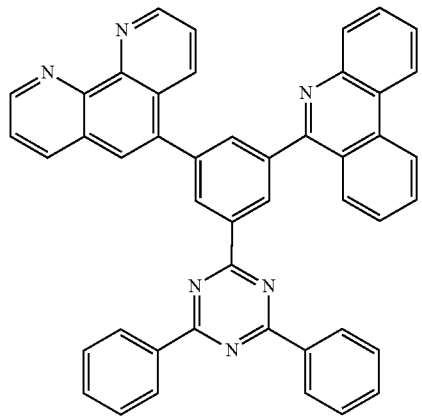
13
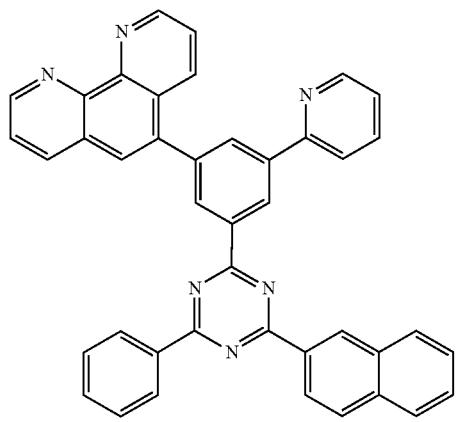
188
-continued
14
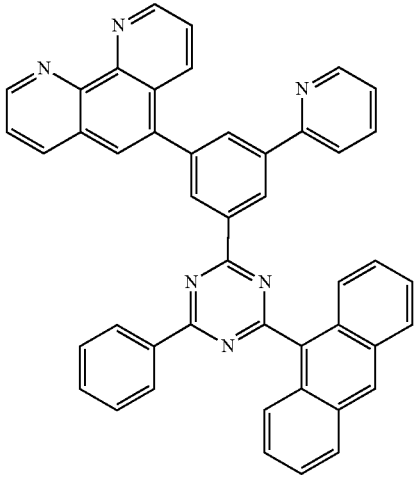
15
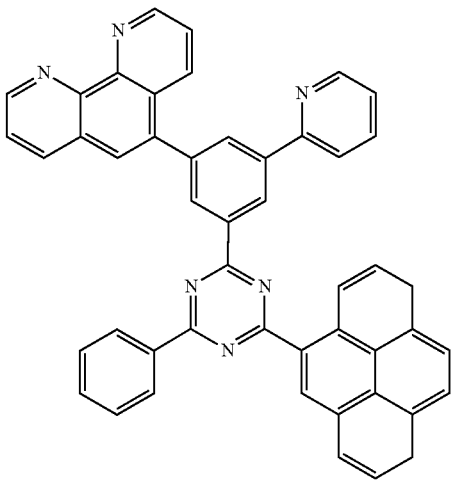
16
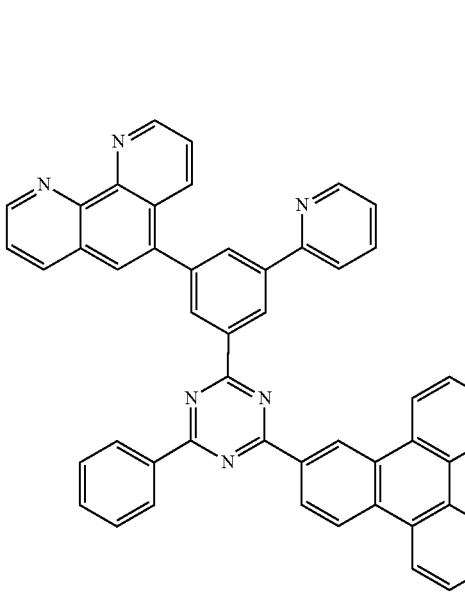

17
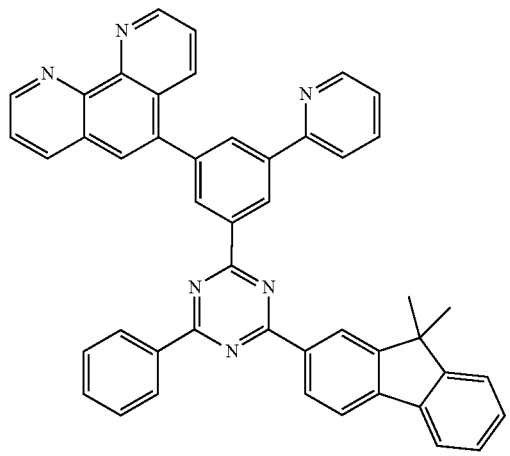
18
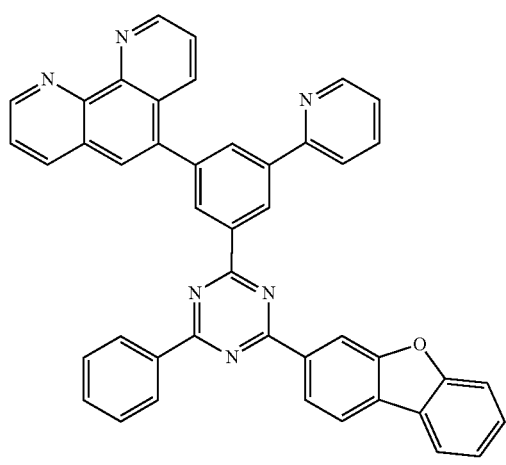
19
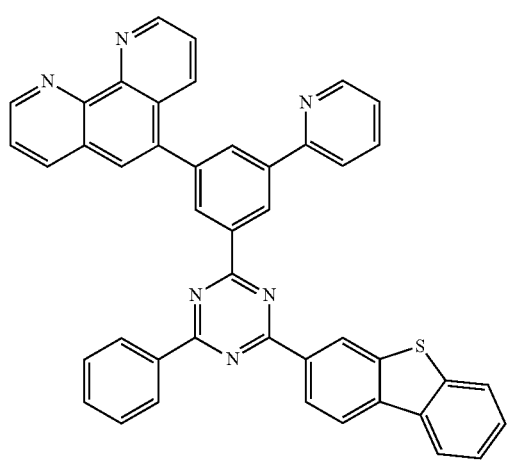
20
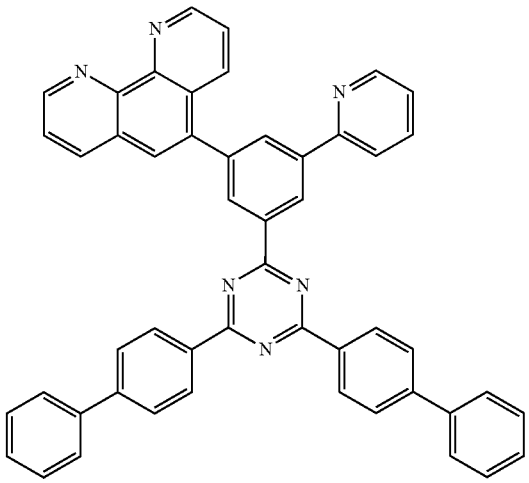
21
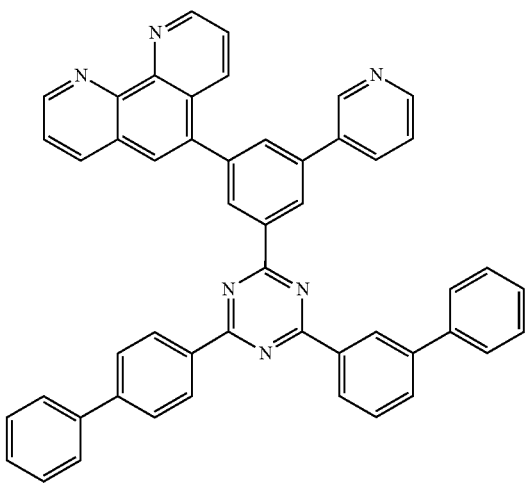
22
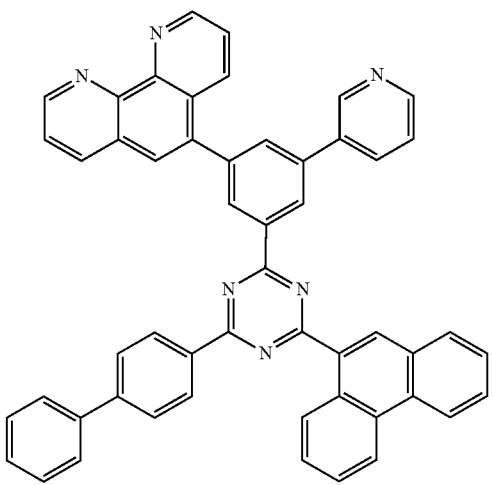

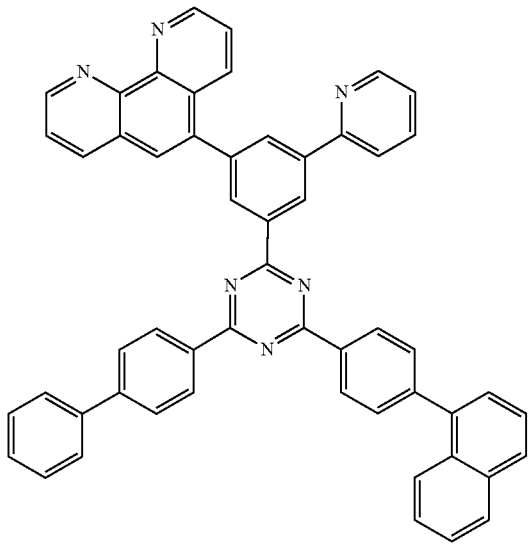
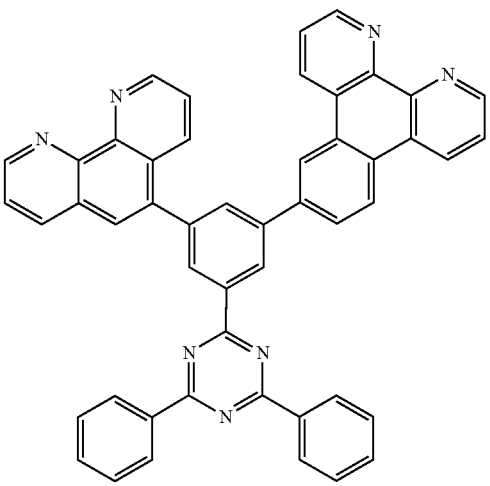
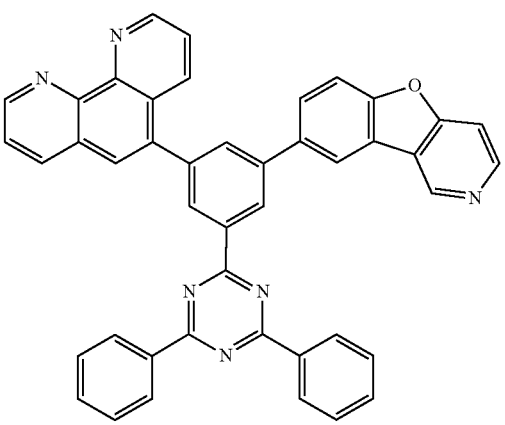
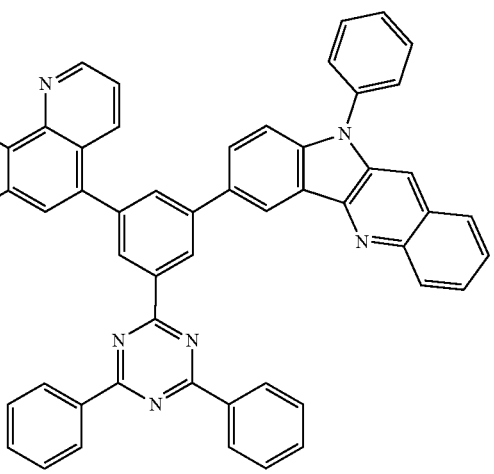

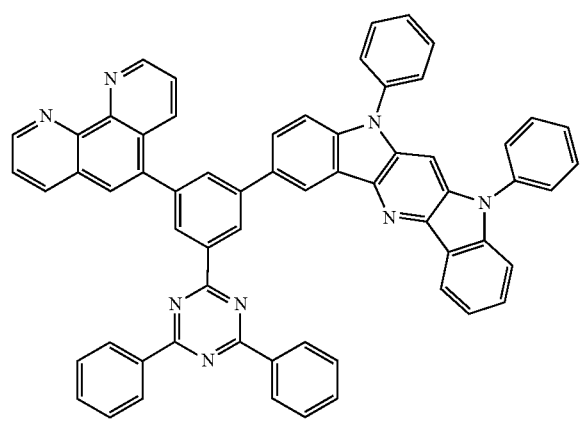
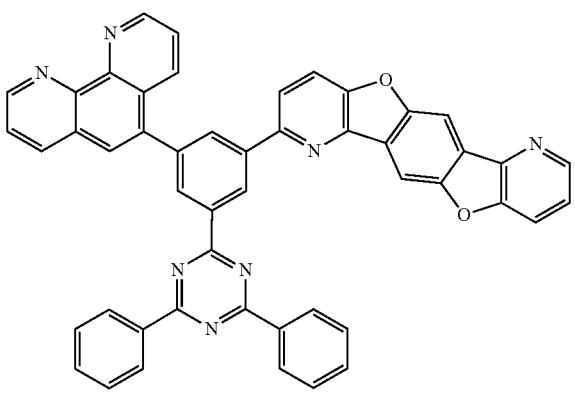
* * * * *